US009549923B2

(12) United States Patent
Mickle et al.

(10) Patent No.: US 9,549,923 B2
(45) Date of Patent: *Jan. 24, 2017

(54) BENZOIC ACID, BENZOIC ACID DERIVATIVES AND HETEROARYL CARBOXYLIC ACID CONJUGATES OF HYDROCODONE, PRODRUGS, METHODS OF MAKING AND USES THEREOF

(71) Applicant: KemPharm, Inc., Coralville, IA (US)

(72) Inventors: Travis Mickle, Celebration, FL (US); Sven Guenther, Coralville, IA (US); Christal Mickle, Celebration, FL (US); Guochen Chi, Coralville, IA (US); Jaroslaw Kanski, Blacksburg, VA (US); Andrea K. Martin, Fincastle, VA (US); Bindu Bera, Blacksburg, VA (US)

(73) Assignee: KemPharm, Inc., Celebration, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/817,581

(22) Filed: Aug. 4, 2015

(65) Prior Publication Data

US 2016/0193204 A1    Jul. 7, 2016

Related U.S. Application Data

(63) Continuation of application No. 14/534,852, filed on Nov. 6, 2014, now abandoned, which is a continuation-in-part of application No. 13/888,587, filed on May 7, 2013, now Pat. No. 8,927,716, which is a continuation-in-part of application No. 12/828,381, filed on Jul. 1, 2010, now Pat. No. 8,461,137.

(60) Provisional application No. 61/222,718, filed on Jul. 2, 2009.

(51) Int. Cl.
| | | |
|---|---|---|
| A61K 31/485 | (2006.01) | |
| A61K 31/167 | (2006.01) | |
| A61K 45/06 | (2006.01) | |
| A61K 47/48 | (2006.01) | |
| C07D 491/08 | (2006.01) | |
| C07D 489/04 | (2006.01) | |
| A61K 9/00 | (2006.01) | |

(52) U.S. Cl.
CPC ........... *A61K 31/485* (2013.01); *A61K 9/0043* (2013.01); *A61K 9/0053* (2013.01); *A61K 31/167* (2013.01); *A61K 45/06* (2013.01); *A61K 47/48038* (2013.01); *A61K 47/48138* (2013.01); *C07D 489/04* (2013.01); *C07D 491/08* (2013.01)

(58) Field of Classification Search
CPC . A61K 45/06; A61K 31/485; A61K 47/48038
USPC ................. 514/160, 161, 282, 557
See application file for complete search history.

(56) References Cited

U.S. PATENT DOCUMENTS

| | | | |
|---|---|---|---|
| 1,731,152 | A | 10/1929 | Schopf |
| 4,668,685 | A | 5/1987 | Shami |
| 7,375,082 | B2 | 5/2008 | Mickle et al. |
| 7,375,083 | B2 | 5/2008 | Mickle et al. |
| 8,461,137 | B2 | 6/2013 | Mickle et al. |
| 8,748,413 | B2 | 6/2014 | Mickle et al. |
| 8,759,368 | B2 | 6/2014 | Mickle et al. |
| 8,828,978 | B2 | 9/2014 | Mickle et al. |
| 8,871,780 | B2 | 10/2014 | Mickle et al. |
| 8,927,716 | B2 | 1/2015 | Mickle et al. |
| 9,125,947 | B2 | 9/2015 | Mickle et al. |
| 9,132,125 | B2 | 9/2015 | Mickle et al. |
| 2004/0058946 | A1 | 3/2004 | Buchwald et al. |
| 2004/0180036 | A1 | 9/2004 | Ashton |
| 2004/0204434 | A1 | 10/2004 | Shafer |
| 2004/0254182 | A1 | 12/2004 | Mulvihill |
| 2005/0074493 | A1 | 4/2005 | Mehta et al. |
| 2005/0080012 | A1 | 4/2005 | Mickle et al. |
| 2005/0176646 | A1 | 8/2005 | Mickle et al. |
| 2006/0167258 | A1 | 7/2006 | Likhotvorik et al. |
| 2008/0090771 | A1 | 4/2008 | Moncrief |
| 2008/0132570 | A1 | 6/2008 | Xiang |
| 2009/0156820 | A1 | 6/2009 | Wang et al. |
| 2011/0002990 | A1 | 1/2011 | Mickle et al. |
| 2011/0002991 | A1 | 1/2011 | Mickle et al. |
| 2012/0142719 | A1 | 6/2012 | Mickle et al. |
| 2012/0142720 | A1 | 6/2012 | Mickle et al. |

(Continued)

FOREIGN PATENT DOCUMENTS

| | | |
|---|---|---|
| AT | 229 496 B | 9/1963 |
| EA | 8864 B1 | 8/2007 |

(Continued)

OTHER PUBLICATIONS

McLaughlin, et al., "Nitrocinnamoyl and Chlorocinnamoyl Derivatives of Dihydrocodeinone: In Vivo and In Vitro Characterization of μ-Selective Agonist and Antagonist Activity," J. of Pharmacology and Experimental Therapeutics, vol. 289, No. 1, 304-311, 1999.
Nieland et al., "Structural Determinants of Opioid Activity in Derivatives of 14-Aminomorphinones: Effect of Substitution in the Aromatic Ring of Cinnamoylaminomorphinones and Codeinones," J. of Medicinal Chemistry, vol. 19, No. 17, 5333-5338, 2006.
Rennison et al., "Cinnamoyl derivatives of 7α-Aminomethyl-6,14-endo-ethanotetrahydrothebaine and 7α-Aminomethyl-6,14-endo-ethanotetrahydrooripavine and Related Opiod Ligands," J. Med. Chem, 5176-5182, 2007.

(Continued)

*Primary Examiner* — Jennifer M Kim
(74) *Attorney, Agent, or Firm* — McAndrews, Held & Malloy, Ltd.; Robert Hoag

(57) ABSTRACT

The presently described technology provides compositions comprising aryl carboxylic acids chemically conjugated to hydrocodone (morphinan-6-one, 4,5-alpha-epoxy-3-methoxy-17-methyl) to form novel prodrugs/compositions of hydrocodone, including benzoates and heteroaryl carboxylic acids, which have a decreased potential for abuse of hydrocodone. The present technology also provides methods of treating patients, pharmaceutical kits and methods of synthesizing conjugates of the present technology.

75 Claims, 35 Drawing Sheets

(56) References Cited

U.S. PATENT DOCUMENTS

| | | | |
|---|---|---|---|
| 2013/0245265 | A1 | 9/2013 | Mickle et al. |
| 2013/0252994 | A1 | 9/2013 | Mickle et al. |
| 2013/0259909 | A1 | 10/2013 | Mickle et al. |
| 2014/0330021 | A1 | 11/2014 | Mickle et al. |
| 2015/0065536 | A1 | 3/2015 | Mickle |

FOREIGN PATENT DOCUMENTS

| | | |
|---|---|---|
| EP | 1782834 | 5/2007 |
| GB | 320749 | 10/1920 |
| WO | 92/08459 | 5/1992 |
| WO | 96/16063 | 5/1996 |
| WO | 99/02529 | 1/1999 |
| WO | 02098427 | 12/2002 |
| WO | 2005/032474 | 4/2005 |
| WO | 2007/140272 A2 | 12/2007 |
| WO | 2011/008636 A1 | 1/2011 |
| WO | 2011002991 | 6/2011 |
| WO | 2011002995 | 6/2011 |

OTHER PUBLICATIONS

Notice of Allowance in U.S. Appl. No. 14/557,570, dated May 4, 2015.

Notice of Allowance in U.S. Appl. No. 14/493,611, dated Jul. 30, 2015.

Corrected Notice of Allowance in U.S. Appl. No. 14/493,611, dated Jul. 30, 2015.

EP Search Report for Appl. No. 10 794 765.7 dated May 6, 2015.

EP Search Report for Appl. No. 10 794 762.4, dated May 6, 2015.

International Search Report for Intl. App. No. PCT/US15/62637, dated Feb. 1, 2016, 14 pages.

Bertram, F. and W. Stoltenberg, "Kinische Erfahrungen Mit Acedicon," Klinische Wochenschrift, 8, Jahrgang, Nr. 19, 1929, pp. 883-886.

Bradford, L.W. and J.W. Brackett, "Systematic Procedure for the Identification of Dangerous Drugs, Poisons, and Narcotics by Ultraviolet Spectrophotometry," Laboratory of Criminalistics, 1956, pp. 353-382.

Catlin, D.H., "Analytical Chemistry and the Games of the XXIIIrd Olympiad in Los Angelos, 1984," Clin. Chem., 1987, pp. 319-327.

Fischer, R. and M.S. Karawia, "Zum Nachweis von Analgeticis und Alkaloiden Mittels Tetraphenylbornatrium (Kalignost) und Nitrokorpern," Aus dem Pharmakognostischen Institut der Universitat Graz, 1953, pp. 366-374.

Hosztafi, S., Köhegyi, I., Simon, C., Fürst, Z., "Synthesis and Analgetic Activity of Nicotinic Esters of Morphine Derivatives" Arzneimittel-Forschung [1993, 43(11):1200-1203].

Hydrocodone chemical structure (ChemSpider, last visit Sep. 18, 2013).

Jane, I., A. McKinnon, and R.J. Flanagan, "High-Performance Liquid Chromatographic Analysis of Basic Drugs on Silica Columns Using Non-Aqueous Ionic Eluents. II. Application of UV, Flourescence and Electrochemical Oxidation detection," Journal of Chromotography, 1985, pp. 191-225.

Leland, D.L., J.O. Polazzi and M.P. Kotick, "Preparation of 7-beta-Methyldihydrothebaine," J. Org . Chem., 1980, pp. 4026-4028.

Micheel, F. and W. Leifels, "Papierchromatographische Trennungen von Alkaloidgemischen an Succinylzellulose-Papieren," Aus dem Organisch-chemischen Institute der Universitate Munster, 1960.

Perrigo et al., "Use of Dual-Column Fused-Silica Capillary Gas Chromatography in Combination with Detector Response Factors for Analytical Toxicology," Journal of Chromatography, 1985 pp. 81-88.

Persson-Stubberud, Karin and Astrom, Ove, "Separation of ibuprofen, codeine phosphate, their degradation products and impurities by capillary electrophoresis I. Method development and optimization with fractional factorial design," J. of Chromatogrphy A, 798 (1998) pp. 307-314.

Small, L., H.M. Fitch and W.E. Smith, "The Addition of Organomagnesium Halides to Pseudocodeine Types. II. Preparation of Nuclear Alkylated Morphine Derivatives," Preparation of Nuclear Alkylated Morphine Derivatives, J. Am. Chem. Soc., 1936, pp. 1457-1463.

Small, L., S. G. Turnbull, and H.M. Fitch, "The Addition of Organomagnesium Halides to Pseudocodiene Types. IV. Nuclear-Substituted Morphine Derivatives," J. Org . Chem., 1938, pp. 204-232.

Thebacon—List of Thebacon suppliers; SciFinder Scholar, Report for CAS RN 466-90-0, 2011.

Von Ernst Vidic, "Eine neue Schnellmethode zur Untersuchung von Urin auf Opiate und deren Derivate," Aus den institut fur gerichtliche und soziale Medizin der Freien Universitat Berlin, 1951.

International Search Report in PCT/US2010/040775, dated Aug. 16, 2010.

International Search Report in PCT/US2010/040785, dated Aug. 20, 2010.

Office Action in U.S. Appl. No. 12/828,381, dated Aug. 1, 2012.

Office Action in U.S. Appl. No. 12/828,456, dated Aug. 21, 2012.

Office Action in U.S. Appl. No. 12/828,381, dated Nov. 8, 2012.

Office Action in U.S. Appl. No. 12/828,456, dated Dec. 19, 2012.

Office Action in U.S. Appl. No. 12/828,456, dated Feb. 6, 2013.

Office Action in U.S. Appl. No. 13/378,857, dated Feb. 22, 2013.

Notice of Allowance in U.S. Appl. No. 12/828,381, dated Mar. 25, 2013.

Office Action in U.S. Appl. No. 13/378,857, dated May 23, 2013.

Office Action in U.S. Appl. No. 13/888,578, dated Jul. 2, 2013.

Notice of Allowance in U.S. Appl. No. 12/828,456, dated Jul. 24, 2013.

Office Action in U.S. Appl. No. 13/888,583, dated Aug. 2, 2013.

Notice of Allowance in U.S. Appl. No. 13/888,578, dated Sep. 4, 2013.

Office Action in U.S. Appl. No. 13/788,800, dated Sep. 19, 2013.

Office Action in U.S. Appl. No. 13/378,857, dated Sep. 25, 2013.

Notice of Allowance in U.S. Appl. No. 13/888,578, dated Feb. 10, 2014.

Notice of Allowance in U.S. Appl. No. 13/378,800, dated Mar. 6, 2014.

Notice of Allowance in U.S. Appl. No. 13/888,583, dated May 2, 2014.

Notice of Allowance in U.S. Appl. No. 12/828,456, dated Jul. 22, 2014.

Notice of Allowance in U.S. Appl. No. 13/888,587, dated Sep. 12, 2014.

Office Action in U.S. Appl. No. 14/493,611, dated Dec. 16, 2014.

Office Action in U.S. Appl. No. 14/557,570, dated Jan. 30, 2015.

Notice of Allowance in U.S. Appl. No. 14/493,611, dated Mar. 24, 2015.

Notice of Allowance in U.S. Appl. No. 14/557,570, dated Apr. 14, 2015.

European Patent Office, Communication with Extended European Search Report in application No. 10794752.4, dated May 6, 2015 (12 pages).

FIGURE 4

4A. Common hydrocodone products and dosage ranges

| Second API | | Hydrocodone Bitartrate |
|---|---|---|
| Name | Strength | Strength[a] |
| acetaminophen | 300 mg | 5 mg |
| | | 7.5 mg |
| | | 10 mg |
| | 325 mg | 5 mg |
| | | 7.5 mg |
| | | 10 mg |
| | 400 mg | 5 mg |
| | | 7.5 mg |
| | | 10 mg |
| | 500 mg | 2.5 mg |
| | | 5 mg |
| | | 7.5 mg |
| | | 10 mg |
| | 650 mg | 7.5 mg |
| | | 10 mg |
| | 660 mg | 10 mg |
| | 750 mg | 7.5 mg |
| | | 10 mg |
| ibuprofen | 200 mg | 2.5 mg |
| | | 7.5 mg |
| | | 10 mg |
| aspirin | 500 mg | 2.5 mg |
| | | 5 mg |
| | | 7.5 mg |
| chlorpheniramine maleate | 2 mg | 5 mg |
| | 4 mg | |
| | 8 mg | 10 mg |
| phenylpropanolamine hydrochloride | 12.5 mg | 2.5 mg |
| | 25 mg | 5 mg |
| phenylephrine hydrochloride | 5 mg | 1.66 mg |
| | 10 mg | 3.75 mg |
| pseudoephedrine hydrochloride | 60 mg | 5 mg |
| phenylephrine hydrochloride | 5 mg | 1.66 mg |
| | | 3.75 mg |
| guaifenesin | 100 mg | 5 mg |
| | 300 mg | |

FIGURE 4 (continued)

4B. Common hydrocodone products and dosage ranges (continued)

| Hydrocodone Bitartrate | Second API | | Third API | |
|---|---|---|---|---|
| Strength[a] | Name | Strength | Name | Strength |
| 5 mg | homatropine methylbromide | 1.5 mg | na | |
| 2.5-10 mg | acetaminophen | 300-750 mg | na | |
| 2.5-10 mg | ibuprofen | 200 mg | na | |
| 5-10 mg | chlorpheniramine maleate | 4-8 mg | na | |
| 2.5-7.5 mg | aspirin | 500 mg | na | |
| 2.5-5 mg | phenylpropanolamine hydrochloride | 12.5-25 mg | na | |
| 1.66-3.75 mg | phenylephrine hydrochloride | 5-10 mg | na | |
| 5 mg | pseudoephedrine hydrochloride | 60 mg | na | |
| 5 mg | guaifenesin | 100-300 mg | na | |
| 1.66-3.75 mg | phenylephrine hydrochloride | 5 mg | pyrilamine maleate | 8.33 mg |
| 5 mg | chlorpheniramine maleate | 2 mg | pseudoephedrine hydrochloride | 30 mg |

[a]Doses of hydrocodone prodrugs of this invention can be calculated from hydrocodone bitartrate (conversion formula was listed in previous invention disclosure document).

Oral PK Profiles (HC)
Bz-HC vs. YYFFI-HC vs. Diglycolate-HC

Oral PK Profiles (HM)
Bz-HC vs. YYFFI-HC vs. Diglycolate-HC

Intranasal PK Profiles (HC)
Bz-HC vs. Adipate-HC

Intranasal PK Profiles (HM)
Bz-HC vs. Adipate-HC

Oral PK Profiles (HC)
Bz-HC vs. Nicotinate-HC vs. Hydrocodone·BT

Oral PK Profiles (HM)
Bz-HC vs. Nicotinate-HC vs. Hydrocodone·BT

FIGURE 13
13A. Synthesis of Benzoate-Hydrocodone
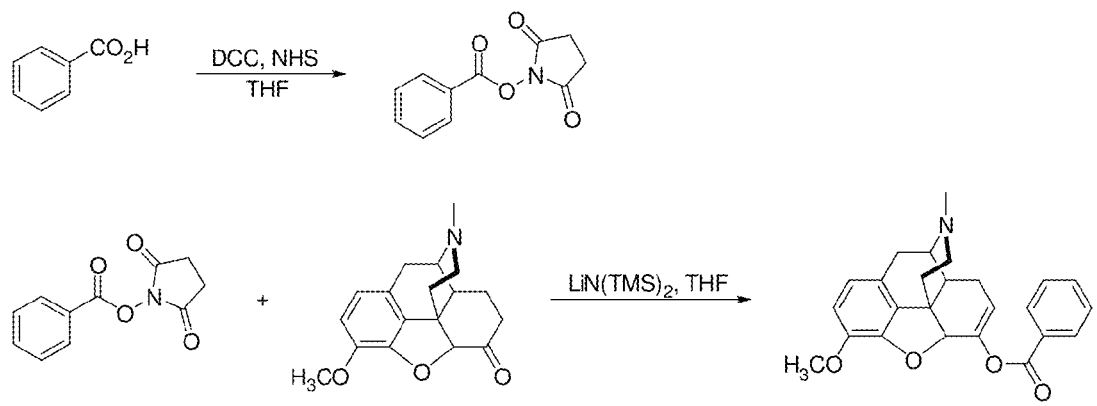
13B. Synthesis of Nicotinate-Hydrocodone
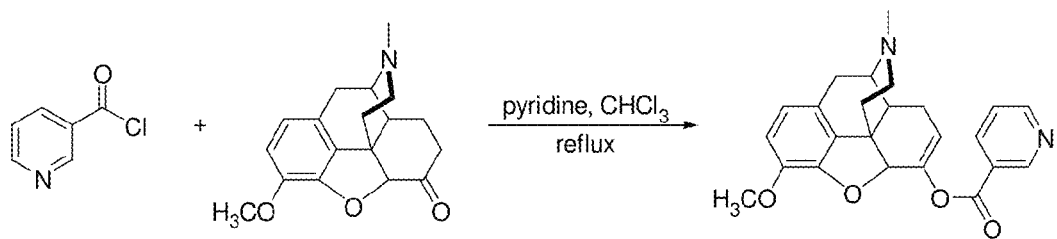

FIGURE 13 (Continued)
13C. Synthesis of 2-Aminobenzoate-Hydrocodone
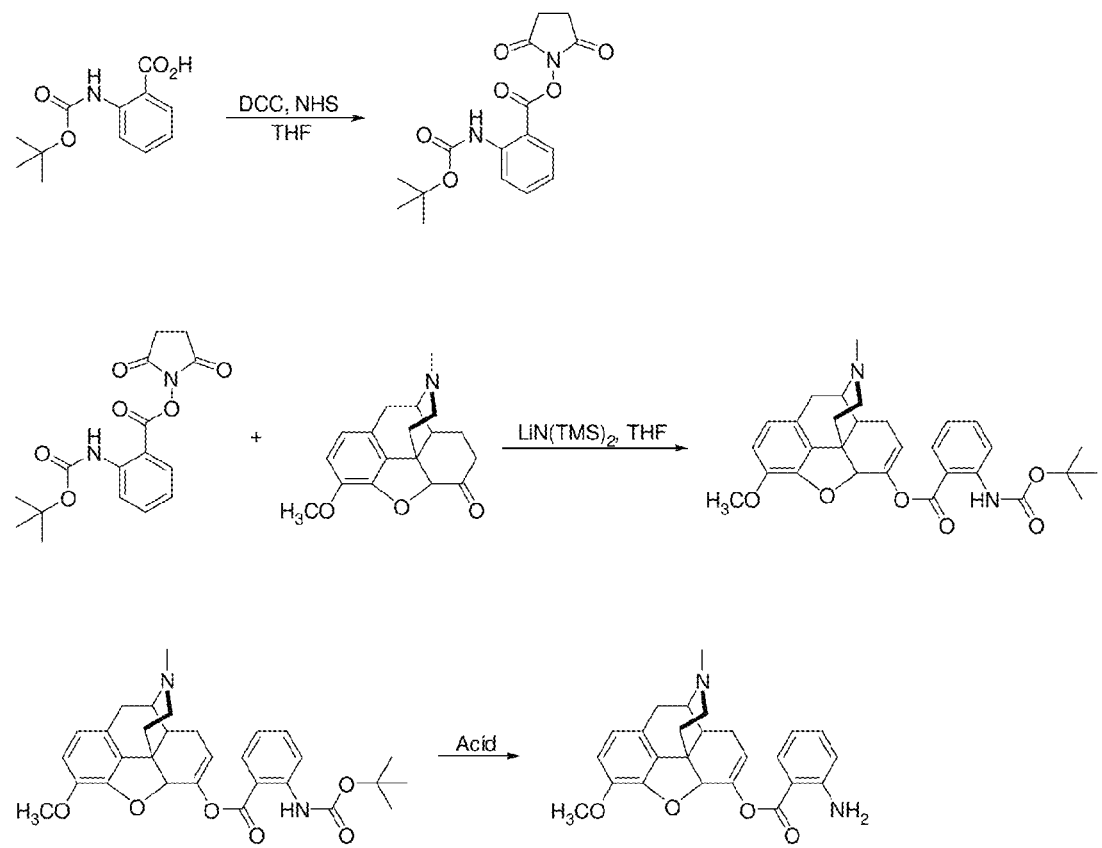
13D. Synthesis of Salicylate-Hydrocodone
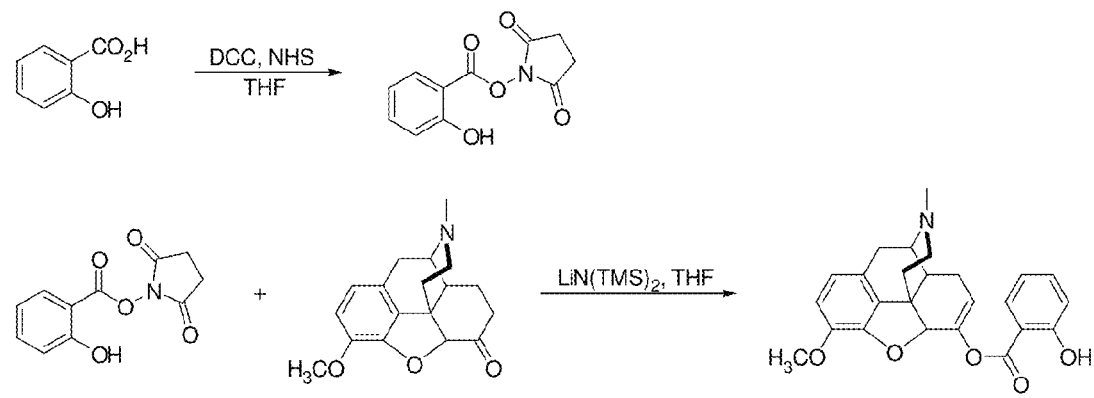

Oral PK Profiles
Bz-HC (HC, HM, intact prodrug)

Oral PK Profiles (HC) in Dogs
Bz-HC vs. Hydrocodone-BT

Oral PK Profiles (HM) in Dogs
Bz-HC vs. Hydrocodone-BT

Oral PK Profiles in Dogs
Bz-HC (HC, intact prodrug)

Intravenous PK Profiles
Bz-HC (HC, HM, intact prodrug)

Oral Dose Range Study (HC)
Bz-HC

Oral Dose Range Study (HM)
Bz-HC (Example 13)

Post-dose prevalence of soft/loose feces after oral administration in dogs.

(Example 15)

(Example 15)

(Example 15)

(Example 16)

(Example 16)

(Example 16)

(Example 16)

Comparison of $T_{max}$ for hydrocodone, hydromorphone and APAP between Day 1 and Day 4.

(Example 16)

Day 1 to Day 4 Accumulation

- HC bars represent hydrocodone
- HM bars represent hydromorphone
- APAP bars represent acetaminophen

Accumulation ratios for $C_{max}$, $AUC_{0-4h}$ and $AUC_{inf}$ from Day 1 to Day 4.

(Example 17)

(Example 17)

(Example 17)

(Example 17)

90% confidence intervals (CI) for the least squares mean ratios (GMR) of the log-transformed PK parameters comparing Bz-HC-HCl/APAP under fed and fasted conditions.

(Example 18)

(Example 18)

(Example 19)

(Example 19)

(Example 19)

BENZOIC ACID, BENZOIC ACID DERIVATIVES AND HETEROARYL CARBOXYLIC ACID CONJUGATES OF HYDROCODONE, PRODRUGS, METHODS OF MAKING AND USES THEREOF

RELATED APPLICATIONS

This application is a continuation of U.S. application Ser. No. 14/534,852, filed Nov. 6, 2014, which is a continuation-in-part of U.S. application Ser. No. 13/888,587, filed May 7, 2013, which is a continuation of U.S. application Ser. No. 12/828,381, filed Jul. 1, 2010, now U.S. Pat. No. 8,461,137, which claims priority to and benefit of U.S. provisional patent application Ser. No. 61/222,718, filed Jul. 2, 2009, both of which are herein incorporated by reference in their entireties.

FEDERALLY SPONSORED RESEARCH OR DEVELOPMENT

[Not Applicable]

BACKGROUND OF THE INVENTION

Opioids are highly effective as analgesics and are commonly prescribed for the treatment of acute and chronic pain. For example, they are also commonly used as antitussives. Opioids, however, also produce euphoria and are highly addictive. As a result, they are often abused with potentially far reaching social and health related consequences.

Because of the inherent potential for abuse, it is desirable that any pharmaceutical composition containing an opioid agonist be made as abuse-resistant or abuse-deterrent as practical. Illicit users often will attempt to circumvent the extended release properties of opioids by injecting or otherwise misusing the pharmaceutical composition in order to achieve an immediate release of the opioid agonist.

Despite their addictive properties and the potential for abuse, morphine-like drugs, particularly, codeine and hydrocodone have been routinely prescribed as treatment for severe acute and chronic pain in recent decades. This is, in part, because there are no alternatives to relieve severe pain (that is resistant to other less potent analgesics such as non-steroidal anti-inflammatory drugs (NSAIDS)). In this regard, there is a need to decrease the abuse potential while still achieving pain relief. Thus far, conventional approaches taken, unfortunately, have not provided a solution.

Hydrocodone is an opioid analgesic and antitussive and occurs as fine, white crystals or as crystalline powder. Hydrocodone is a semisynthetic narcotic analgesic prepared from codeine with multiple actions qualitatively similar to those of codeine. It is mainly used for relief of moderate to moderately severe pain. Additionally, it is used as an antitussive in cough syrups and tablets in sub-analgesic doses (e.g., 2.5-5 mg).

Patients taking opioid analgesics such as hydrocodone for pain relief can become unintentionally addicted. As tolerance to the opioids develops, more drug is needed to alleviate the pain and generate the sense of well-being initially achieved with the originally prescribed dose. This leads to dose escalation, which if left unchecked can rapidly lead addiction. In some cases patients have become very addicted in as little as thirty days.

BRIEF SUMMARY OF THE INVENTION

The present technology utilizes covalent conjugation of the opioid hydrocodone with certain aryl carboxylic acids to decrease its potential for causing overdose or abuse by requiring the active hydrocodone to be released through enzymatic or metabolic breakdown of the conjugate in vivo. The present technology also provides methods of delivering hydrocodone as conjugates that release the hydrocodone following oral administration while being resistant to abuse by circuitous routes such as intravenous ("shooting") injection and intranasal administration ("snorting").

The presently described technology in at least one aspect provides a slow/sustained/controlled/extended release composition of conjugated hydrocodone that allows slow/sustained/controlled/extended delivery of the hydrocodone and/or its active metabolite, hydromorphone, into the blood system of a human or animal within a therapeutic window upon, for example, oral administration. At least some compositions/formulations of the current technology can lessen addiction/abuse potential and/or other common side effects associated with hydrocodone and similar opioid compounds, among others.

In one aspect, the present technology provides a composition comprising at least one conjugate of hydrocodone and at least one benzoic acid, a derivative thereof, or a combination thereof.

In another aspect, the present technology provides a composition comprising at least one conjugate of hydrocodone and at least one ligand wherein the ligand is a benzoic acid or derivative thereof, a salt thereof, or a combination thereof, the benzoic acid or derivative thereof having the following formula I:

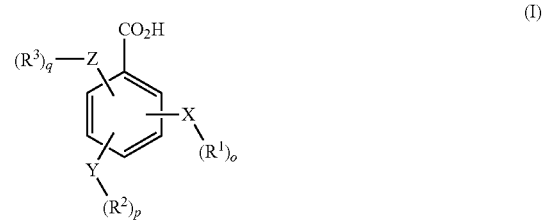

where X, Y and Z are independently selected from the group consisting of H, O, S, NH and $-(CH_2)_x-$; $R^1$, $R^2$ and $R^3$ are independently selected from the group consisting of H, alkyl, alkoxy, aryl, alkenyl, alkynyl, halo, haloalkyl, alkylaryl, arylalkyl, heterocycle, arylalkoxy, cycloalkyl, cycloalkenyl and cycloalkynyl; o, p, q are independently selected from 0 or 1; and x is an integer between 1 and 10. In some embodiments of this aspect, the benzoic acid or derivative thereof is an aminobenzoate, a hydroxybenzoate, an aminohydroxybenzoate, a derivative thereof, or combination thereof.

In yet another aspect, the present technology provides one or more compositions or conjugates of hydrocodone for use to treat pain, preferably moderate to severe pain, or for use to reduce or prevent oral, intranasal or intravenous drug abuse. In some aspects, the conjugates provide oral, intranasal or parenteral drug abuse resistance.

In a still further aspect, the present technology provides at least one conjugate or composition of hydrocodone that exhibits a slower rate of release over time and a greater or equal AUC when compared to an equivalent molar amount of unconjugated hydrocodone over the same time period. In other aspects, the conjugate or composition of hydrocodone exhibits less variability in an oral PK profile when compared to unconjugated hydrocodone. In yet another aspect, at least one conjugate or composition of this aspect of the present technology can exhibit reduced side effects when compared with unconjugated hydrocodone or prevents drug tampering by either physical (e.g., crushing) or chemical (e.g., extraction) manipulation.

In an additional aspect, at least one conjugate is provided in an amount sufficient to provide a therapeutically bioequivalent AUC when compared to an equivalent molar amount of unconjugated hydrocodone. In further aspects, at least one conjugate is provided in an amount sufficient to provide a therapeutically bioequivalent AUC when compared to an equivalent molar amount of unconjugated hydrocodone, but does not provide a $C_{max}$ spike or has a lower $C_{max}$ than a therapeutically equivalent amount of unconjugated hydrocodone. In yet a further aspect, at least one conjugate is provided in an amount sufficient to provide a therapeutically bioequivalent AUC when compared to an equivalent molar amount of unconjugated hydrocodone, but does not provide an equivalent $C_{max}$ spike. In some aspects, at least one conjugate provides an equivalent $C_{max}$ spike when compared to unconjugated hydrocodone.

In another aspect, the present technology provides at least one method for treating a patient having a disease, disorder or condition involving, requiring or mediated by binding of an opioid to one or more opioid receptors of the patient, comprising orally administering to the patient a pharmaceutically effective amount of at least one conjugate of hydrocodone and at least one benzoic acid or derivative thereof, a salt thereof, or a combination thereof, the benzoic acid or derivative thereof having formula I:

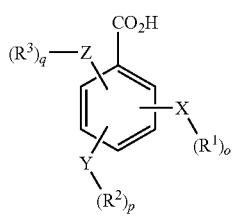

where X, Y and Z are independently selected from the group consisting of H, O, S, NH and —$(CH_2)_x$—; $R^1$, $R^2$ and $R^3$ are independently selected from the group consisting of H, alkyl, alkoxy, aryl, alkenyl, alkynyl, halo, haloalkyl, alkylaryl, arylalkyl, heterocycle, arylalkoxy, cycloalkyl, cycloalkenyl and cycloalkynyl; o, p, q are independently selected from 0 or 1; and x is an integer between 1 and 10.

In a further aspect, at least one conjugate binds irreversibly to one or more opioid receptors of the patient.

In an additional aspect, the present technology provides at least one method for treating a patient having a disease, disorder or condition involving, requiring or mediated by inhibiting the binding of an opioid to the opioid receptors of the patient, comprising orally administering to the patient a pharmaceutically effective amount of at least one conjugate of hydrocodone and at least one benzoic acid or derivative thereof, a salt thereof, or a combination thereof, the benzoic acid or derivative thereof having formula I:

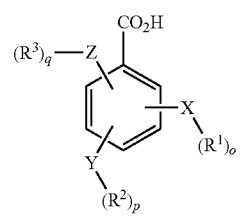

wherein X, Y and Z are independently selected from the group consisting of H, O, S, NH and —$(CH_2)_x$—; $R^1$, $R^2$ and $R^3$ are independently selected from the group consisting of H, alkyl, alkoxy, aryl, alkenyl, alkynyl, halo, haloalkyl, alkylaryl, arylalkyl, heterocycle, arylalkoxy, cycloalkyl, cycloalkenyl and cycloalkynyl; o, p, q are independently selected from 0 or 1; and x is an integer between 1 and 10.

In some aspects, the present technology provides at least one conjugate that reversibly inhibits binding of an opioid to an opioid receptor of the patient.

In another aspect, the present technology provides at least one method for treating a patient having a disease, disorder or condition (such as pain) which can be treated by the binding of an opioid to one or more opioid receptors of a patient, the method comprising orally administering to the patient a pharmaceutically effective amount of at least one conjugate of hydrocodone and at least one benzoic acid, a salt thereof, a derivative thereof or a combination thereof.

In yet another aspect, the present technology provides at least one method for treating a patient having a disease, disorder or condition (such as addiction) which can be treated by inhibiting the binding of an opioid to the opioid receptors of the patient, comprising orally administering to the patient a pharmaceutically effective amount of at least one conjugate of hydrocodone and at least one benzoic acid, a salt thereof, a derivative thereof or a combination thereof.

In yet another aspect, the present technology provides at least one method for rehabilitation, such as a step down therapy, of an opioid addicted patient, comprising orally administering to the patient a pharmaceutically effective amount of at least one conjugate of hydrocodone and at least one benzoic acid, a salt thereof, a derivative thereof or a combination thereof.

In a still further aspect, the present technology provides at least one pharmaceutical kit including a specified amount of individual doses in a package containing a pharmaceutically effective amount of at least one conjugate of hydrocodone and at least one benzoate, a salt thereof, a derivative thereof or a combination thereof, the benzoate having the formula I:

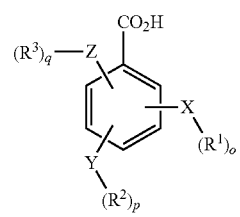

wherein X, Y and Z are independently selected from the group consisting of H, O, S, NH and —$(CH_2)_x$—; $R^1$, $R^2$ and $R^3$ are independently selected from the group consisting of H, alkyl, alkoxy, aryl, alkenyl, alkynyl, halo, haloalkyl, alkylaryl, arylalkyl, heterocycle, arylalkoxy, cycloalkyl, cycloalkenyl and cycloalkynyl; o, p, q can be independently selected from 0 or 1; and x is an integer between 1 and 10. In some aspects, the kit further comprises instructions for use of the kit in at least one method for treating or preventing drug withdrawal symptoms or pain in a human or animal patient.

In another aspect, the present technology provides a pharmaceutical kit including a specified amount of individual doses in a package containing a pharmaceutically effective amount of at least one conjugate of hydrocodone and at least one benzoic acid, a salt thereof, a derivative thereof or a combination thereof. In some aspects, the kit further includes instructions for use of the kit in at least one method for treating or preventing drug withdrawal symptoms or pain in a human or animal patient.

In yet another aspect, the present technology provides a composition comprising at least one conjugate of hydrocodone and at least one heteroaryl carboxylic acid, a derivative thereof, or a combination thereof.

In yet another aspect, the present technology provides at least one conjugate of hydrocodone and at least one heteroaryl carboxylic acid, a derivative thereof, or a combination thereof where at least one heteroaryl carboxylic acid is selected from formula II, formula III or formula IV, wherein formula II, formula III and formula IV are:

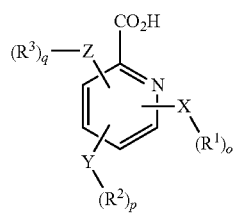

(II)

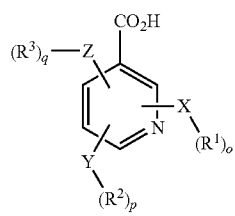

(III)

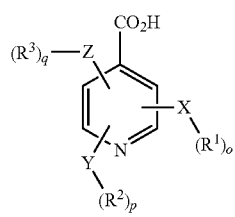

(IV)

wherein X, Y and Z are independently selected from the group consisting of H, O, S, NH and —(CH$_2$)$_x$—; $R^1$, $R^2$ and $R^3$ are independently selected from the group consisting of H, alkyl, alkoxy, aryl, alkenyl, alkynyl, halo, haloalkyl, alkylaryl, arylalkyl, heterocycle, arylalkoxy, cycloalkyl, cycloalkenyl and cycloalkynyl; o, p, q are independently selected from 0 or 1; and x is an integer from 1 to 10. In some aspects, at least one heteroaryl carboxylic acid is a pyridine derivative.

In some aspects, the present technology provides at least one conjugate that prevents drug tampering by either physical or chemical manipulation.

In another aspect, the present technology provides at least one method for treating a patient having a disease, disorder or condition requiring or mediated by binding of an opioid to the opioid receptors of the patient, comprising orally administering to the patient a pharmaceutically effective amount of at least one conjugate of hydrocodone and at least one heteroaryl carboxylic acid.

In a further aspect, the present technology provides at least one method for treating a patient having a disease, disorder or condition requiring or mediated by binding of an opioid to the opioid receptors of the patient, comprising orally administering to the patient a pharmaceutically effective amount of at least one conjugate of hydrocodone and at least one heteroaryl carboxylic acid, where the heteroaryl carboxylic acid is selected from formula II, formula III or formula IV, wherein formula II, formula III and formula IV are:

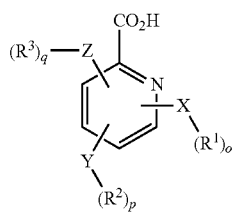

(II)

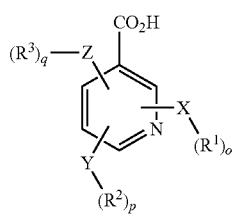

(III)

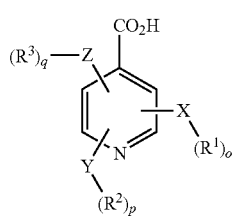

(IV)

where X, Y and Z are independently selected from the group consisting of H, O, S, NH and —(CH$_2$)$_x$—; $R^1$, $R^2$ and $R^3$ are independently selected from the group consisting of H, alkyl, alkoxy, aryl, alkenyl, alkynyl, halo, haloalkyl, alkylaryl, arylalkyl, heterocycle, arylalkoxy, cycloalkyl, cycloalkenyl and cycloalkynyl; o, p, q are independently selected from 0 or 1; and x is an integer from 1 to 10.

In another aspect, the present technology provides at least one method for treating a patient having a disease, disorder or condition requiring or mediated by binding of an opioid to the opioid receptors of the patient, comprising orally administering to the patient a pharmaceutically effective amount of at least one conjugate of hydrocodone and at least one nicotinic acid, a derivative thereof, or a combination thereof.

In another aspect, the present technology provides at least one method for treating a patient having a disease, disorder or condition requiring or mediated by inhibiting binding of an opioid to the opioid receptors of the patient, comprising orally administering to the patient a pharmaceutically effective amount of at least one conjugate of hydrocodone and at least one heteroaryl carboxylic acid. In some aspects, the heteroaryl carboxylic acid is selected from formula II, formula III or formula IV, wherein formula II, formula III and formula IV are:

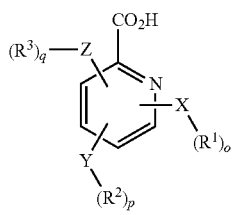

(II)

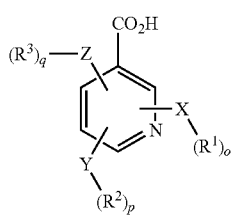

(III)

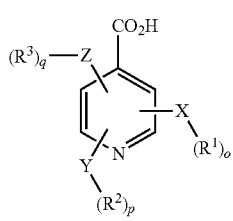

(IV)

wherein X, Y and Z are independently selected from the group consisting of H, O, S, NH and $-(CH_2)_x-$; $R^1$, $R^2$ and $R^3$ are independently selected from the group consisting of H, alkyl, alkoxy, aryl, alkenyl, alkynyl, halo, haloalkyl, alkylaryl, arylalkyl, heterocycle, arylalkoxy, cycloalkyl, cycloalkenyl and cycloalkynyl; o, p, q are independently selected from 0 or 1; and x is an integer from 1 to 10.

In another aspect, the present technology provides at least one method for treating a patient having a disease, disorder or condition requiring or mediated by inhibiting binding of an opioid to the opioid receptors of the patient, comprising orally administering to the patient a pharmaceutically effective amount of at least one conjugate of hydrocodone and at least one nicotinic acid, a derivative thereof, or a combination thereof.

In yet another aspect, the present technology provides a pharmaceutical kit including a specified number of individual doses in a package containing a pharmaceutically effective amount of at least one conjugate of hydrocodone and at least one heteroaryl carboxylic acid, a derivative thereof, or a combination thereof, wherein the heteroaryl carboxylic acid is selected from formula II, formula III or formula IV, wherein formula II, formula III and formula IV are:

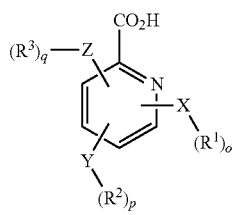

(II)

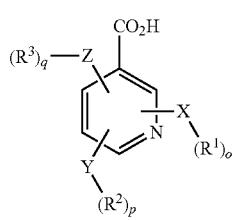

(III)

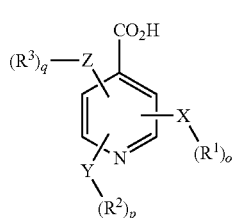

(IV)

wherein X, Y and Z are independently selected from the group consisting of H, O, S, NH and $-(CH_2)_x-$; $R^1$, $R^2$ and $R^3$ are independently selected from the group consisting of H, alkyl, alkoxy, aryl, alkenyl, alkynyl, halo, haloalkyl, alkylaryl, arylalkyl, heterocycle, arylalkoxy, cycloalkyl, cycloalkenyl and cycloalkynyl; o, p, q are independently selected from 0 or 1; and x is an integer from 1 to 10. In some aspects, the kit further comprises instructions for use of the kit in at least one method for treating or preventing drug withdrawal symptoms or pain in a human or animal patient.

In yet another aspect, the present technology provides a prodrug comprising at least one conjugate of hydrocodone and at least one benzoic acid or benzoic acid derivative, a salt thereof, or a combination thereof, the benzoic acid or benzoic acid derivative having the following formula I:

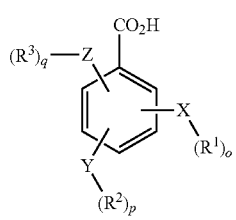

(I)

where X, Y and Z are independently selected from the group consisting of H, O, S, NH and $-(CH_2)_x-$; $R^1$, $R^2$ and $R^3$ are independently selected from the group consisting of H, alkyl, alkoxy, aryl, alkenyl, alkynyl, halo, haloalkyl, alkylaryl, arylalkyl, heterocycle, arylalkoxy, cycloalkyl, cycloalkenyl and cycloalkynyl; o, p, q are independently selected from 0 or 1; and x is an integer between 1 and 10.

In another aspect, the present technology provides a prodrug comprising at least one conjugate of hydrocodone and at least one benzoic acid, a derivative thereof, or a combination thereof.

In yet another aspect, the present technology provides a prodrug comprising at least one conjugate of hydrocodone and at least one heteroaryl carboxylic acid, a derivative thereof, or a combination thereof. In some aspects, the prodrug includes at least one heteroaryl carboxylic acid selected from formula II, formula III or formula IV, wherein formula II, formula III and formula IV are:

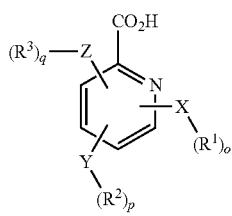

(II)

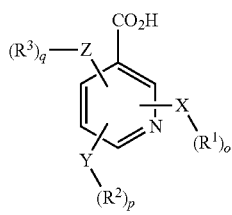

(III)

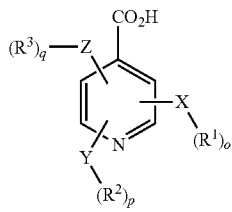

(IV)

wherein X, Y and Z are independently selected from the group consisting of H, O, S, NH and —$(CH_2)_x$—; $R^1$, $R^2$ and $R^3$ are independently selected from the group consisting of H, alkyl, alkoxy, aryl, alkenyl, alkynyl, halo, haloalkyl, alkylaryl, arylalkyl, heterocycle, arylalkoxy, cycloalkyl, cycloalkenyl and cycloalkynyl; o, p, q are independently selected from 0 or 1; and x is an integer from 1 to 10.

In yet another aspect, the present technology provides a prodrug comprising at least one conjugate of hydrocodone and at least one nicotinic acid, a derivative thereof, or a combination thereof.

In some aspects, the prodrug includes an aminobenzoate, a hydroxybenzoate, an aminohydroxybenzoate, a derivative thereof, or combination thereof.

In some aspects, at least one conjugate binds reversibly to the opioid receptors of the patient. In yet another aspect, at least one conjugate prevents or reduces at least one constipatory side effect of unconjugated hydrocodone.

In additional aspects, the current technology is related to a composition comprising 5 mg of benzoate-hydrocodone hydrochloride (Bz-HC.HCl) which contains a molar equivalent of 3.4 mg of hydrocodone.

In other aspects, the current technology is related to a composition comprising 6.67 mg of benzoate-hydrocodone hydrochloride (Bz-HC.HCl) which contains a molar equivalent of 4.54 mg of hydrocodone.

In further aspects, the current technology is related to a composition comprising 10 mg of benzoate-hydrocodone hydrochloride (Bz-HC.HCl) which contains a molar equivalent of 6.8 mg of hydrocodone.

In additional aspects, the current technology is related to a composition comprising 13.34 mg of benzoate-hydrocodone hydrochloride (Bz-HC.HCl) which contains a molar equivalent of 9.08 mg of hydrocodone.

In other aspects, the current technology is related to a composition comprising 6.67 mg benzoate-hydrocodone hydrochloride and 325 mg acetaminophen (Bz-HC.HCl/APAP, 6.67 mg/325 mg) which contains a molar equivalent of 4.54 mg of hydrocodone.

In further aspects, the current technology is related to a composition comprising 13.34 mg benzoate-hydrocodone hydrochloride and 650 mg acetaminophen (Bz-HC.HCl/APAP, 13.34 mg/650 mg) which contains a molar equivalent of 9.08 mg of hydrocodone.

BRIEF DESCRIPTION OF SEVERAL VIEWS OF THE DRAWINGS

FIG. 4. FIG. 4A is a Table of common hydrocodone products and dosage ranges and FIG. 4B is a Table of common hydrocodone products used in cough syrups.

FIG. 13. Synthesis diagrams of conjugates of hydrocodone. FIG. 13A depicts the synthesis of benzoate hydrocodone. FIG. 13B depicts the synthesis of nicotinate hydrocodone (nicotinic acid). FIG. 13C depicts the synthesis of 2-aminobenzoate hydrocodone. FIG. 13D depicts the synthesis of salicylate hydrocodone.

DETAILED DESCRIPTION OF THE INVENTION

Definitions and Conventions

Figure 1:
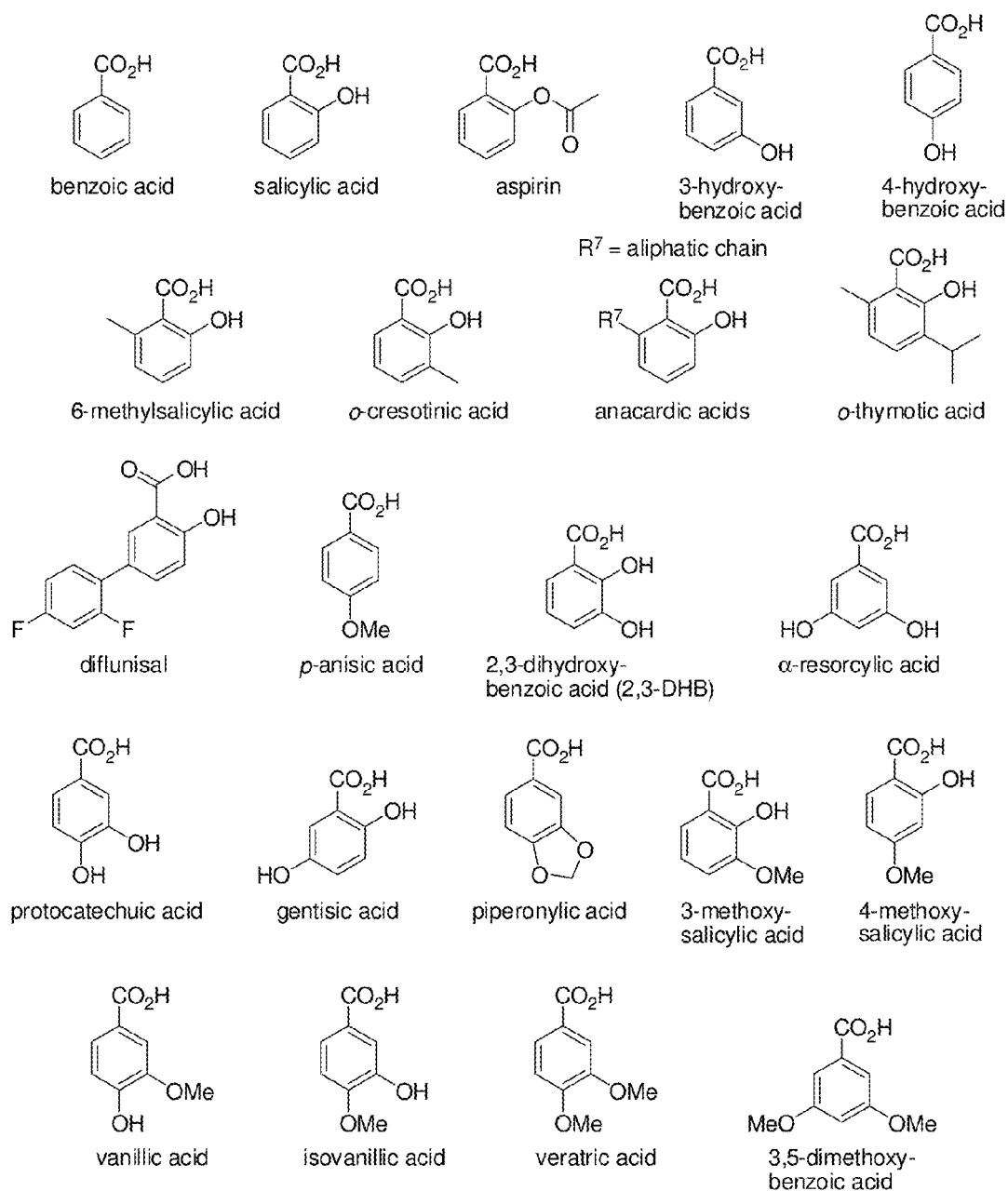
FIG. 1. Chemical structures of hydroxybenzoic acids and benzoic acid derivatives for use in the making of the conjugates of the present technology.
Figure 1:
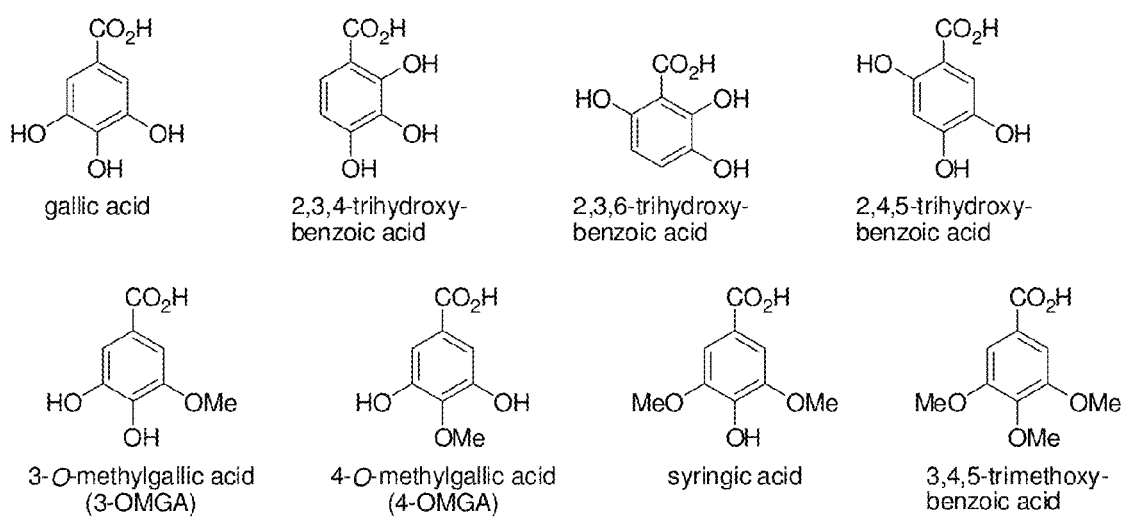

The present technology provides compositions comprising aryl carboxylic acids chemically conjugated to hydrocodone (morphinan-6-one, 4,5-alpha-epoxy-3-methoxy-17-methyl) to form novel prodrugs and compositions of hydrocodone. In some embodiments, the chemical bond between these two moieties can be established by reacting the C-6 enol tautomer of hydrocodone with the activated carboxylic acid function of an aryl carboxylic acid thereby creating an enol-ester conjugate.

The use of "opioid" is meant to include any drug that activates the opioid receptors found in the brain, spinal cord and gut. There are four broad classes of opioids: naturally occurring opium alkaloids, such as morphine (the prototypical opioid) codeine, and thebaine; endogenous opioid peptides, such as endorphins; semi-synthetics such as heroine, oxycodone and hydrocodone that are produced by modifying natural opium alkaloids (opiates) and have similar chemical structures; and pure synthetics such as fentanyl and methadone that are not produced from opium and may have very different chemical structures than the opium alkaloids. Additional examples of opioids are hydromorphone, oxymorphone, methadone, levorphanol, dihydrocodeine, meperidine, diphenoxylate, sufentanil, alfentanil, propoxyphene, pentazocine, nalbuphine, butorphanol, buprenorphine, meptazinol, dezocine, and pharmaceutically acceptable salts thereof.

The use of "hydrocodone" is meant to include a semi-synthetic narcotic analgesic and antitussive prepared from codeine with multiple actions qualitatively similar to those of codeine. It is commonly used for the relief of moderate to moderately severe pain. Trade names include Anexsia™, Hycodan™, Hycomine™, Lorcet™ Lortab™, Norco™, Tussionex™, Tylox™, and Vicodin™. Other salt forms of hydrocodone, such as hydrocodone bitartrate and hydrocodone polistirex, are encompassed by the present technology.

The use of "prodrug" is meant to include pharmacologically inactive substances that are a modified form of a pharmacologically active drug to which it is converted in the body by, for example, enzymatic action, such as during first pass metabolism.

As used herein, the following conventional unit abbreviations and terms are used as follows: "pg" refers to picogram, "ng" refers to nanogram, "rig" refers to microgram, "mg" refers to milligram, "g" refers to gram, "kg" refers to kilogram, "mL" refers to milliliter, "h" refers to hour and "t" refers to time.

As used herein, the following conventional pharmacokinetic abbreviations and terms are used as follows: "PK" refers to pharmacokinetics, "$AUC_{0-t}$" refers to area under the plasma concentration-time curve to the last time with a concentration ≥LLOQ, "$AUC_{inf}$" refers to the area under the plasma concentration-time curve to infinity, "$C_{max}$" refers to the maximum plasma concentration, "$T_{max}$" refers to the time of maximum plasma concentration, "λz" refers to the elimination rate constant and "$t_{1/2}$" refers to the elimination half-life.

As used herein, the following conventional statistical abbreviations and terms are used as follows: "LLOQ" refers to the validated lower limit of the bioanalytical method, "ANOVA" refers to Analysis of Variance and "p" refers to probability.

As used herein, "APAP" refers to acetaminophen.

As used herein, "LC/MS/MS" refers to liquid chromatography/mass spectrometry/mass spectrometry.

Some embodiments of the present technology provide carboxylic acids conjugated to hydrocodone, where the carboxylic acid group is directly attached to the aryl moiety. Carboxylic acids directly attached to the aryl moiety include benzoates and heteroaryl carboxylic acids.

Some embodiments of the present technology provide at least one conjugate of hydrocodone and at least one benzoic acid or benzoic acid derivative, a salt thereof, or a combination thereof. Benzoates are common in nature and include, for example but are not limited to, aminobenzoates (e.g., anthranilic acid analogs such as fenamates), aminohydroxybenzoates and hydroxybenzoates (e.g., salicylic acid analogs).

The general structure of benzoic acid and benzoic acid derivatives of the present technology is:

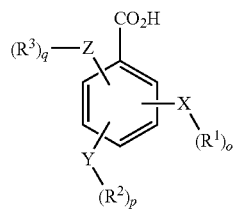

where X, Y and Z can be independently any combination of H, O, S, NH or —($CH_2$)—; $R^1$, $R^2$ and $R^3$ can be independently any of the following: H, alkyl, alkoxy, aryl, alkenyl, alkynyl, halo, haloalkyl, alkylaryl, arylalkyl, heterocycle, arylalkoxy, cycloalkyl, cycloalkenyl or cycloalkynyl, and o, p, q can be independently either 0 or 1.

Suitable hydroxyobenzoic acids can be found in FIG. 1 and include, but are not limited to, benzoic acid, salicylic acid, acetylsalicylic acid (aspirin), 3-hydroxybenzoic acid, 4-hydroxybenzoic acid, 6-methylsalicylic acid, o,m,p-cresotinic acid, anacardic acids, 4,5-dimethylsalicylic acid, o,m, p-thymotic acid, diflusinal, o,m,p-anisic acid, 2,3-dihydroxybenzoic acid (2,3-DHB), α,β,γ-resorcylic acid, protocatechuic acid, gentisic acid, piperonylic acid, 3-methoxysalicylic acid, 4-methoxysalicylic acid, 5-methoxysalicylic acid, 6-methoxysalicylic acid, 3-hydroxy-2-methoxybenzoic acid, 4-hydroxy-2-methoxybenzoic acid, 5-hydroxy-2-methoxybenzoic acid, vanillic acid, isovanillic acid, 5-hydroxy-3-methoxybenzoic acid, 2,3-dimethoxybenzoic acid, 2,4-dimethoxybenzoic acid, 2,5-dimethoxybenzoic acid, 2,6-dimethoxybenzoic acid, veratric acid (3,4-dimethoxybenzoic acid), 3,5-dimethoxybenzoic acid, gallic acid, 2,3,4-trihydroxybenzoic acid, 2,3,6-trihydroxybenzoic acid, 2,4,5-trihydroxybenzoic acid, 3-O-methylgallic acid (3-OMGA), 4-O-methylgallic acid (4-OMGA), 3,4-O-dimethylgallic acid, syringic acid, 3,4,5-trimethoxybenzoic acid.

Figure 2:
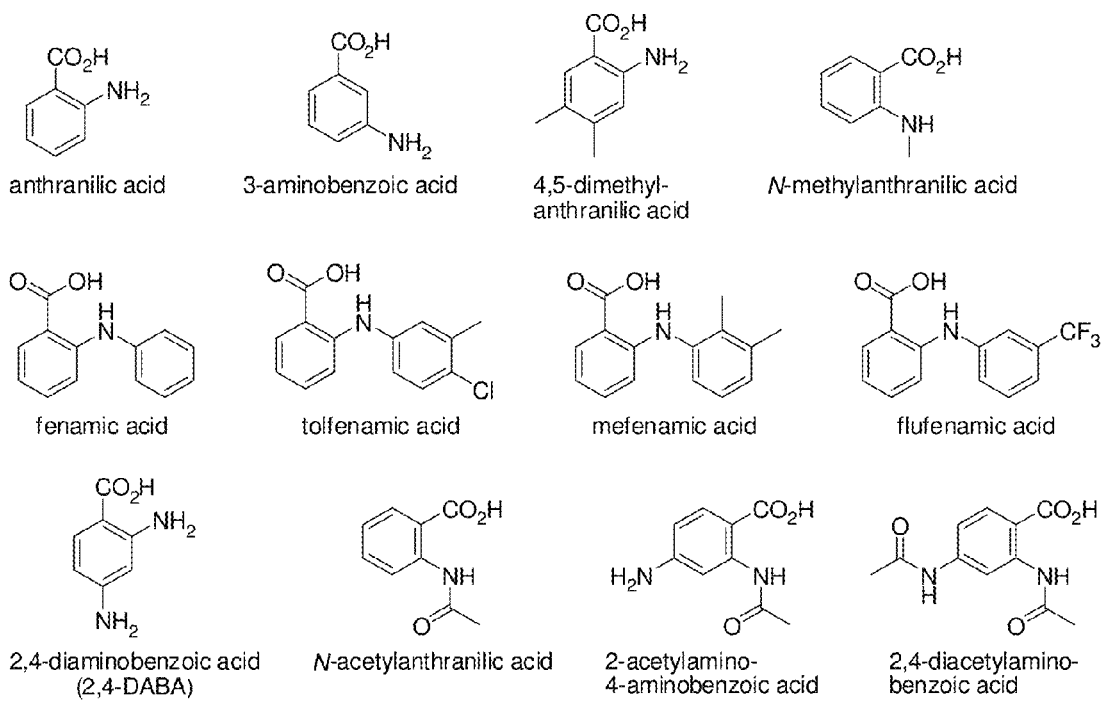
FIG. 2. Chemical structures of aminobenzoic acids for use in the making of the conjugates of the present technology.

Suitable aminobenzoic acids are shown in FIG. 2 and include, but are not limited to, anthranilic acid, 3-aminobenzoic acid, 4,5-dimethylanthranilic acid, N-methylanthranilic acid, N-acetylanthranilic acid, fenamic acids (e.g., tolfenamic acid, mefenamic acid, flufenamic acid), 2,4-diaminobenzoic acid (2,4-DABA), 2-acetylamino-4-aminobenzoic acid, 4-acetylamino-2-aminobenzoic acid, 2,4-diacetylaminobenzoic acid.

Figure 3:
FIG. 3. Chemical structures of aminohydroxybenzoic acids for use in the making of conjugates of the present technology.

Suitable aminohydroxybenzoic acids are shown in FIG. 3 and include, but are not limited to, 4-Aminosalicylic acid, 3-hydroxyanthranilic acid, 3-methoxyanthranilic acid.

In some embodiments, the composition includes a benzoate conjugate comprising at least one hydrocodone conjugated to at least one benzoic acid or benzoic acid derivative, salt thereof or combination thereof.

In some embodiments, the benzoates include numerous benzoic acid analogs, benzoate derivatives with hydroxyl or amino groups or a combination of both. The hydroxyl and amino functions may be present in their free form or capped with another chemical moiety, preferably but not limited to methyl or acetyl groups. The phenyl ring may have additional substituents, but the total number of substituents can be four or less, three or less, or two or less.

In another embodiment, the prodrug or conjugate composition of the present technology is benzoate-hydrocodone, which has the structure:

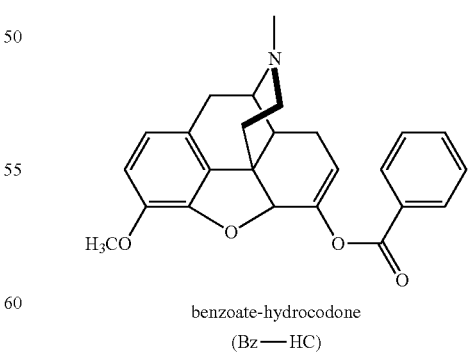

benzoate-hydrocodone
(Bz—HC)

In yet another embodiment, the present technology provides a prodrug or composition comprising at least one conjugate of hydrocodone and at least one heteroaryl carboxylic acid, a derivative thereof, or a combination thereof.

The heteroaryl carboxylic acid can be selected from formula II, formula III or formula IV where formula II, formula III and formula IV are:

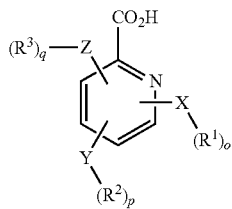

(II)

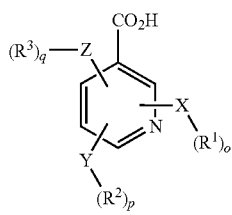

(III)

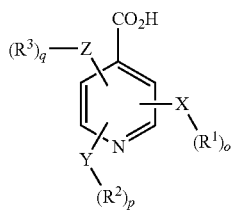

(IV)

For these formulas, X, Y and Z are independently selected from the group consisting of H, O, S, NH and —$(CH_2)_x$—; $R^1$, $R^2$ and $R^3$ are independently selected from the group consisting of H, alkyl, alkoxy, aryl, alkenyl, alkynyl, halo, haloalkyl, alkylaryl, arylalkyl, heterocycle, arylalkoxy, cycloalkyl, cycloalkenyl and cycloalkynyl; o, p, q are independently selected from 0 or 1; and x is an integer from 1 to 10.

In some embodiments, the carboxy group of the aryl carboxylic acids can be attached directly to the aromatic ring. The present technology includes both carbon-only aryl groups and aryl groups with heteroatoms (heteroaryl). The aryl or heteroaryl group which is connected directly to the carboxyl function can be a 6-membered ring and contains no or one heteroatom. In some embodiments, the additional substituted or unsubstituted aromatic or aliphatic rings can be fused to this 6-membered aryl or heteroaryl moiety. In some embodiments, the aryl carboxylic acids may have only one free carboxylic acid group and the total number of phenyl substituents on the 6-membered ring should be four or less, for example, 4, 3, 2 or 1.

In some embodiments of the present technology, depending on the individual aryl carboxylic acid that is connected to hydrocodone, the conjugate of hydrocodone can have a neutral, free acid, free base, or various pharmaceutically acceptable anionic or cationic salt forms or salt mixtures with any ratio between positive and negative components. These salt forms include, but are not limited to: acetate, L-aspartate, besylate, bicarbonate, carbonate, D-camsylate, L-camsylate, citrate, edisylate, fumarate, gluconate, hydrobromide/bromide, hydrochloride/chloride, D-lactate, L-lactate, D,L-lactate, D,L-malate, L-malate, mesylate, pamoate, phosphate, succinate, sulfate, D-tartrate, L-tartrate, D,L-tartrate, meso-tartrate, benzoate, gluceptate, D-glucuronate, hybenzate, isethionate, malonate, methylsulfate, 2-napsylate, nicotinate, nitrate, orotate, stearate, tosylate, acefyllinate, aceturate, aminosalicylate, ascorbate, borate, butyrate, camphorate, camphocarbonate, decanoate, hexanoate, cholate, cypionate, dichloroacetate, edentate, ethyl sulfate, furate, fusidate, galactarate (mucate), galacturonate, gallate, gentisate, glutamate, glutarate, glycerophosphate, heptanoate (enanthate), hydroxybenzoate, hippurate, phenylpropionate, iodide, xinafoate, lactobionate, laurate, maleate, mandelate, methanesulfonate, myristate, napadisilate, oleate, oxalate, palmitate, picrate, pivalate, propionate, pyrophosphate, salicylate, salicylsulfate, sulfosalicylate, tannate, terephthalate, thiosalicylate, tribrophenate, valerate, valproate, adipate, 4-acetamidobenzoate, camsylate, octanoate, estolate, esylate, glycolate, thiocyanate, and undecylenate.

For the present technology, a suitable conjugate of hydrocodone includes nicotinate-hydrocodone, which has the following structure:

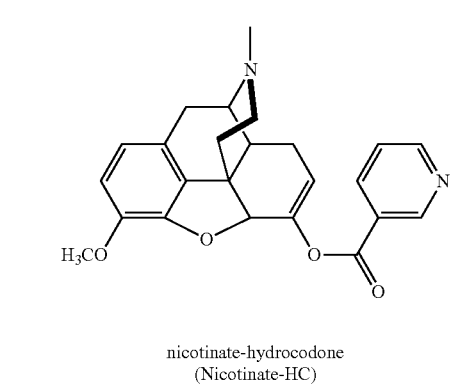

nicotinate-hydrocodone
(Nicotinate-HC)

Some embodiments of the present technology provide a conjugate of hydrocodone that is broken down in vivo either enzymatically or otherwise, releasing the active hydrocodone and the respective aryl carboxylic acid or metabolites thereof. The aryl carboxylic acids used in the conjugates of the present technology are non-toxic at the given dosing levels and are preferably known drugs, natural products, metabolites, or GRAS (Generally Regarded As Safe) compounds (e.g., preservatives, dyes, flavors, etc.) or non-toxic mimetics thereof.

Compounds, conjugates, products, prodrugs, compositions and methods of the present technology provide, for example, reduced potential for overdose, reduced potential for abuse or addiction and/or improve hydrocodone's characteristics with regard to high toxicities or suboptimal release profiles. Without wishing to be limited to the below theory, it is believed that the presently described and claimed technology provides overdose protection that may occur when the described and claimed conjugates, compounds, compositions, prodrugs, and/or products are exposed to different enzymes and/or metabolic pathways by oral administration where the conjugates, compounds, compositions, products and/or prodrugs are exposed through the gut and first-pass metabolism as opposed to exposure to enzymes in the circulation or mucosal membranes which limits the ability of the hydrocodone from being released from the conjugate. Therefore, abuse resistance and/or abuse deterrence is provided by limiting the "rush" or "high" available from the active hydrocodone released by the prodrug, product, composition, compound, and/or conjugate of the present technology and limiting the effectiveness of alternative routes of administration.

The compositions of the present technology preferably have no or a substantially decreased pharmacological activity when administered through injection or intranasal routes of administration. However, they remain orally bioavailable. Again, not wanting to be bound by any particular theory, the bioavailability of the compositions of the present technology can be a result of the hydrolysis of the chemical linkage (i.e., a covalent linkage) following oral administration. In at least one embodiment of the present technology, release of hydrocodone is reduced when the composition, compound, conjugate, product, or prodrug of the present technology is delivered, for example, by parenteral routes.

For example, in one embodiment, the composition of the present technology maintains its effectiveness and abuse resistance following the crushing of the tablet, capsule or other oral dosage form. In contrast, from parental non-conjugated (or "unconjugated") forms of hydrocodone, the hydrocodone is released immediately following crushing allowing the content of the crushed tablet to be used by injection or snorting producing the "rush" effect sought by addicts.

In some embodiments of the present technology, the conjugates of hydrocodone can be given orally to an animal or human patient, and, upon administration, release the active hydrocodone by being hydrolyzed in the body. Not to be bound by any particular theory, it is believed that since the aryl carboxylic acids are naturally occurring metabolites or mimetics thereof or pharmaceutically active compounds, these conjugates can be easily recognized by physiological systems resulting in hydrolysis and release of hydrocodone. The conjugates themselves have either no or limited pharmacological activity as a conjugate and consequently may follow a metabolic pathway that differs from the parent drug.

In some embodiments of the present technology, the choice of a suitable aryl carboxylic acids ("ligands") to conjugate to hydrocodone determines the release of hydrocodone into the systemic circulation and can be controlled even when the conjugate is administered via routes other than oral. In one embodiment, the modified hydrocodone would release hydrocodone similar to free or unmodified hydrocodone. In another embodiment, the conjugated hydrocodone releases hydrocodone in a controlled or sustained form. In some embodiments, this controlled release can alleviate certain side-effects and improve upon the safety profile of the parent drug. These side-effects may include, but are not limited to, anxiety, bruising, constipation, decreased appetite, difficulty breathing, dizziness, drowsiness, dry throat, diarrhea, headache, nausea, stomach cramps, stomach pain, vomiting. In another embodiment, the conjugated hydrocodone would selectively allow hydrocodone to be metabolized to hydromorphone. In some embodiments, these conjugates can be used for pain relief, such as moderate to severe pain relief.

Hydrocodone and other opioids are also highly addictive and prone to substance abuse. Recreational drug abuse of opioids is a common problem and usually begins with oral doses taken with the purpose of achieving euphoria ("rush", "high"). Over time the drug abuser often increases the oral dosages to attain more powerful "highs" or to compensate for heightened opioid tolerance. This behavior can escalate and result in exploring of other routes of administration such as intranasal ("snorting") and intravenous ("shooting").

In some embodiments of the present technology, the hydrocodone that is conjugated with a suitable aryl carboxylic acid ligand does not result in rapid spikes in plasma concentrations after oral administration that is sought by a potential drug abuser. In some embodiments, hydrocodone released from these conjugates has a delayed $T_{max}$ and possibly lower $C_{max}$ than the unconjugated hydrocodone. Not to be bound by any particular theory, it is believed that the conjugates of the present technology, when taken orally or by other non-oral routes, do not provide the feeling of a "rush" even when taken at higher doses but still maintain pain relief.

Additionally, in some embodiments, hydrocodone conjugated with appropriate ligands of the present technology is not hydrolyzed efficiently when administered via non-oral routes. As a result, these conjugates do not generate high plasma or blood concentrations of released hydrocodone when injected or snorted compared to free hydrocodone administered through these routes.

In some embodiments, the conjugates of the present technology, since they consist of covalently bound hydrocodone, are not able to be physically manipulated to release the hydrocodone opioid from the conjugated hydrocodone by methods, for example, of grinding up or crushing of solid forms. Further, the conjugates of the present technology exhibits resistance to chemical hydrolysis under conditions a potential drug abuser may apply to "extract" the active portion of the molecule, for example, by boiling, or acidic or basic solution treatment of the conjugate.

The compositions and prodrugs of the present technology can be oral dosage forms. These dosage forms include but are not limited to tablet, capsule, caplet, troche, lozenge, powder, suspension, syrup, solution or oral thin film (OTF). Preferred oral administration forms are capsule, tablet, solutions and OTF.

Solid dosage forms can include, but are not limited to, the following types of excipients: antiadherents, binders, coatings, disintegrants, fillers, flavors and colors, glidants, lubricants, preservatives, sorbents and sweeteners.

Oral formulations of the present technology can also be included in a solution or a suspension in an aqueous liquid or a non-aqueous liquid. The formulation can be an emulsion, such as an oil-in-water liquid emulsion or a water-in-oil liquid emulsion. The oils can be administered by adding the purified and sterilized liquids to a prepared enteral formula, which is then placed in the feeding tube of a patient who is unable to swallow.

Soft gel or soft gelatin capsules may be prepared, for example by dispersing the formulation in an appropriate vehicle (vegetable oils are commonly used) to form a high viscosity mixture. This mixture is then encapsulated with a gelatin based film using technology and machinery known to those in the soft gel industry. The individual units so formed are then dried to constant weight.

Chewable tablets, for example, may be prepared by mixing the formulations with excipients designed to form a relatively soft, flavored, tablet dosage form that is intended to be chewed rather than swallowed. Conventional tablet machinery and procedures, for example, direct compression and granulation, i.e., or slugging, before compression, can be utilized. Those individuals involved in pharmaceutical solid dosage form production are versed in the processes and the machinery used, as the chewable dosage form is a very common dosage form in the pharmaceutical industry.

Film coated tablets, for example may be prepared by coating tablets using techniques such as rotating pan coating methods or air suspension methods to deposit a contiguous film layer on a tablet.

Compressed tablets, for example may be prepared by mixing the formulation with excipients intended to add binding qualities to disintegration qualities. The mixture is either directly compressed or granulated then compressed using methods and machinery known to those in the industry. The resultant compressed tablet dosage units are then packaged according to market need, for example, in unit dose, rolls, bulk bottles, blister packs, etc.

The present technology also contemplates the use of biologically-acceptable carriers which may be prepared from a wide range of materials. Without being limited to, such materials include diluents, binders and adhesives, lubricants, plasticizers, disintegrants, colorants, bulking substances, flavorings, sweeteners and miscellaneous materials such as buffers and adsorbents in order to prepare a particular medicated composition.

Binders may be selected from a wide range of materials such as hydroxypropylmethylcellulose, ethylcellulose, or other suitable cellulose derivatives, povidone, acrylic and methacrylic acid co-polymers, pharmaceutical glaze, gums, milk derivatives, such as whey, starches, and derivatives, as well as other conventional binders known to persons working in the art. Exemplary non-limiting solvents are water, ethanol, isopropyl alcohol, methylene chloride or mixtures and combinations thereof. Exemplary non-limiting bulking substances include sugar, lactose, gelatin, starch, and silicon dioxide.

It should be understood that in addition to the ingredients particularly mentioned above, the formulations of the present technology can include other suitable agents such as flavoring agents, preservatives and antioxidants. Such antioxidants would be food acceptable and could include vitamin E, carotene, BHT or other antioxidants.

Other compounds which may be included by admixture are, for example, medically inert ingredients, e.g., solid and liquid diluents, such as lactose, dextrose, saccharose, cellulose, starch or calcium phosphate for tablets or capsules, olive oil or ethyl oleate for soft capsules and water or vegetable oil for suspensions or emulsions; lubricating agents such as silica, talc, stearic acid, magnesium or calcium stearate and/or polyethylene glycols; gelling agents such as colloidal clays; thickening agents such as gum tragacanth or sodium alginate, binding agents such as starches, arabic gums, gelatin, methylcellulose, carboxymethylcellulose or polyvinylpyrrolidone; disintegrating agents such as starch, alginic acid, alginates or sodium starch glycolate; effervescing mixtures; dyestuff; sweeteners; wetting agents such as lecithin, polysorbates or laurylsulfates; and other therapeutically acceptable accessory ingredients, such as humectants, preservatives, buffers and antioxidants, which are known additives for such formulations.

For oral administration, fine powders or granules containing diluting, dispersing and/or surface-active agents may be presented in a draught, in water or a syrup, in capsules or sachets in the dry state, in a non-aqueous suspension wherein suspending agents may be included, or in a suspension in water or a syrup. Where desirable, flavoring, preserving, suspending, thickening or emulsifying agents can be included.

Liquid dispersions for oral administration may be syrups, emulsions or suspensions. The syrups may contain as carrier, for example, saccharose or saccharose with glycerol and/or mannitol and/or sorbitol. In particular a syrup for diabetic patients can contain as carriers only products, for example sorbitol, which do not metabolize to glucose or which metabolize only a very small amount to glucose. The suspensions and the emulsions may contain a carrier, for example a natural gum, agar, sodium alginate, pectin, methylcellulose, carboxymethylcellulose or polyvinyl alcohol.

Current approved formulations of hydrocodone are combination therapies of hydrocodone and one or more other non-narcotic active ingredient depending on intended indication. Examples of these active pharmaceuticals include, but are not limited to, acetaminophen, phenylpropanolamine, homatropine, ibuprofen, aspirin, pheniramine, chlorpheniramine, phenylephrine, pseudoephedrine, pyrilamine and guaifenesin. The conjugated hydrocodone of the present technology can be formulated with one or a combination of these or other active substances or as standalone active ingredient without any other actives.

Certain formulations of the compounds, products, compositions, conjugates and prodrugs of the current technology comprise Bz-HC.HCl, bulking agents and diluents, such as, for example, microcrystalline cellulose and crospovidone, disintegrants, such as, for example, starch 1500 G, binders, such as, for example, povidone K30, lubricants, such as, for example, stearic acid, and granulation solvents, such as, for example, purified water. Such formulations of the current technology may also include additional pharmaceutical actives, such as, for example, acetaminophen.

The amounts and relative percentages of the different active and inactive components of the formulations of the current technology can be modified, selected and adjusted in order to arrive at desirable formulations, dosages and dosage forms for therapeutic administration of the compounds, products, compositions, conjugates and prodrugs of the current technology. One such oral dosage formulation of the present technology is presented, for example, in Table 1.

TABLE 1

| Component and Quality Standard (and Grade, if applicable) | Function | Strength (label claim) 6.67 mg/325 mg (Bz-HC•HCl/Acetaminophen) | |
|---|---|---|---|
| | | mg/tablet | % w/w |
| Bz-HC•HCl [a], Professed | Active | 6.67 | 1.21 |
| Acetaminophen USP | Active | 325.0 | 59.09 |
| Microcrystalline Cellulose NF | Bulking Agent | 154.78 | 28.16 |
| Crospovidone NF | Bulking Agent/Diluent | 16.0 | 2.9 |
| Starch 1500 G NF | Disintegrant | 20.0 | 3.64 |
| Povidone K30 NF | Binder | 23.65 | 4.3 |
| Stearic Acid NF | Lubricant | 3.9 | 0.71 |
| Purified water [a] | Granulation solvent | n/a | n/a |

[a] Removed by evaporation during the process.

The conjugate compositions or prodrugs may be used in methods of treating a patient having a disease, disorder or condition requiring or mediated by binding or inhibiting binding of an opioid to the opioid receptors of the patient. Treatment comprises orally administering to the patient a pharmaceutically effective amount of at least one conjugate of hydrocodone as described in the present technology. The conjugate can exhibit a slower rate of release over time and AUC when compared to an equivalent molar amount of unconjugated hydrocodone. In other embodiments, at least one conjugate can exhibit less variability in the oral PK profile when compared to unconjugated hydrocodone.

In other embodiments, at least one conjugate is provided in an amount sufficient to provide a therapeutically bioequivalent AUC (area under the curve) when compared to a molar equivalent amount of unconjugated hydrocodone. In further embodiments, the conjugate is provided in an amount sufficient to provide a therapeutically bioequivalent AUC when compared to unconjugated hydrocodone but has a lower $C_{max}$ (peak concentration) in plasma or does not provide an equivalent $C_{max}$ in plasma concentrations. In some aspects, the conjugate is provided in an amount sufficient to provide a therapeutically bioequivalent $C_{max}$ when compared to unconjugated hydrocodone.

Suitable diseases, disorders or conditions that can be treated by the prodrugs or compositions of the present technology are narcotic addiction or drug addiction and/or acute or chronic pain.

Dosages for the conjugates of the present technology depend on their molecular weight and the respective weight-percentage of hydrocodone as part of the whole conjugate, and therefore can be higher than the dosages of free hydrocodone. Dosages can be calculated based on the strengths of dosages of hydrocodone bitartrate which range between 2.5 mg and 15 mg per dose. Dose conversion from hydrocodone bitartrate to hydrocodone prodrug can be performed using the following formula:

dose(HC prodrug/conjugate)=[dose(HC bitartrate)×(molecular weight(HC prodrug/conjugate)/494.49)]/proportion of hydrocodone released from prodrug/conjugate HC: hydrocodone Suitable dosages of the conjugated hydrocodone of the present technology include, but are not limited to, formulations including from about 0.5 mg or higher, alternatively from about 2.5 mg or higher, alternatively from about 5.0 mg or higher, alternatively from about 7.5 mg or higher, alternatively from about 10 mg or higher, alternatively from about 20 mg or higher, alternatively from about 30 mg or higher, alternatively from about 40 mg or higher, alternatively from about 50 mg or higher, alternatively from about 60 mg or higher, alternatively from about 70 mg or higher, alternatively from about 80 mg or higher, alternatively from about 90 mg or higher, alternatively from about 100 mg or higher, and include any additional increments thereof, for example, 0.1, 0.2, 0.25, 0.3, 0.4, 0.5, 0.6, 0.7, 0.75, 0.8, 0.9 or 1.0 mg and multiplied factors thereof, (e.g., ×1, ×2, ×2.5, ×5, ×10, ×100, etc.). The present technology also includes dosage formulations including currently approved formulations of hydrocodone (See FIG. 4), where the dosage can be calculated using the above-noted formula determined by the amount of hydrocodone bitartrate. The present technology provides for dosage forms formulated as a single therapy or as a combination therapy with other API's (FIG. 4).

The conjugates of hydrocodone with derivatives of benzoic acid or nicotinic acid of the present technology have a number of advantages including, but not limited to, a reduced patient variability of plasma concentrations of hydrocodone or hydromorphone when compared to free hydrocodone, reduced drug abuse potential, reduced risk of chemical or physical manipulation resulting in full dosage of hydrocodone released, improved dosage forms through covalent linkage to carboxylic acids or derivatives thereof, increased or decreased metabolism of hydrocodone to hydromorphone and/or decreased side-effects other than drug abuse.

Hydrocodone is a narcotic analgesic, which acts as weak agonist at opioid receptors in the central nervous system (CNS). It primarily affects the μ (mu) receptor (OP3), but also exhibits agonist activity at the δ (delta) receptor (OP1) and κ (kappa) receptor (OP2). Additionally, hydrocodone displays antitussive properties by suppressing the cough reflex in the medullary cough center of the brain.

Side effects of opioid analgesics include gastrointestinal dysfunction caused by the opioids binding to the mu (μ) receptors present in the gastrointestinal tract. The side-effects in the stomach include a reduction in the secretion of hydrochloric acid, decreased gastric motility, thus prolonging gastric emptying time, which can result in esophageal reflux. Passage of the gastric contents through the duodenum may be delayed by as much as 12 hours, and the absorption of orally administered drugs is retarded. In the small intestines the opioid analgesics diminish biliary, pancreatic and intestinal secretions and delay digestion of food in the small intestine. Propulsive peristaltic waves in the colon are diminished or abolished after administration of opioids, and tone is increased to the point of spasm. The resulting delay in the passage of bowel contents causes considerable desiccation of the feces, which, in turn retards their advance through the colon. These actions, combined with inattention to the normal sensory stimuli for defecation reflex due to the central actions of the drug, contribute to opioid-induced constipation (OIC).

Hydrocodone is used for the treatment of moderate to moderately severe pain and for inhibition of cough (especially dry, nonproductive cough). The prodrugs of the present technology may be administered for the relief of pain or cough depression or for the treatment of any condition that may require the blocking of opioid receptors.

The conjugates of the present technology can provide a decrease in side effects of the opioid analgesic, including reduced or inhibited constipatory effects.

The present technology also provides a method of synthesis for the preparation of the conjugated hydrocodone of the present technology. In one embodiment, the synthesis of the present technology includes the steps of:
1. Protection of the ligand, if necessary;
2. Activation of the ligand carboxylic acid group, if not already in activated form;
3. Addition of the activated ligand to hydrocodone or vice versa in the presence of base; and
4. Removal of ligand protecting groups, if applicable.

If the aryl carboxylic acid contains any additional reactive functional groups that may interfere with the coupling to hydrocodone, it may be necessary to first attach one or more protecting groups. Any suitable protecting group may be used depending on the type of functional group and reaction conditions. Some protecting group examples are: acetyl (Ac), β-methoxyethoxymethyl ether (MEM), methoxymethyl ether (MOM), p-methoxybenzyl ether (PMB), trimethylsilyl (TMS), tert.-butyldimethylsilyl (TBDPS), triisopropylsilyl (TIPS), carbobenzyloxy (Cbz), p-methoxybenzyl carbonyl (Moz), tert.-butyloxycarbonyl (Boc), 9-fluorenylmethyloxycarbonyl (Fmoc), benzyl (Bn), p-methoxybenzyl (MPM), tosyl (Ts). Temporary formation of acetals or ketals from carbonyl functions may also be appropriate.

The carboxylic acid group of the ligands should be activated in order to react with hydrocodone and to generate appreciable amounts of conjugate. This activation can be accomplished in numerous ways by a variety of coupling agents known to one skilled in the art. Examples of such coupling agents are: N,N'-dicyclohexylcarbodiimide (DCC), N-(3-dimethylaminopropyl)-N'-ethylcarbodiimide (EDCI), N,N'-diisopropylcarbodiimide (DIC), 1,1'-carbonyldiimidazole (CDI) or other carbodiimides; (benzotriazol-1-yloxy)tris(dimethylamino)phosphonium hexafluorophosphate (BOP), bromotripyrrolidinophosphonium hexafluorophosphate (PyBroP), (benzotriazol-1-yloxy)tripyrrolidinophosphonium hexafluorophosphate (PyBOP) or other phosphonium-based reagents; O-(benzotriazol-1-yl)-N,N,N',N'-tetramethyluronium hexafluorophosphate (HBTU), O-(benzotriazol-1-yl)-N,N,N',N'-tetramethyluronium tetrafluoroborate (TBTU), fluoro-N,N,N',N'-tetramethylformamidinium hexafluorophosphate (TFFH), N,N,N',N'-tetramethyl-O—(N-succinimidyl)uronium tetrafluoroborate (TSTU) or other aminium-based reagents. The aryl carboxylic acid can also be converted to a suitable acyl halide, acyl azide or mixed anhydride.

A base may be required at any step in the synthetic scheme of an aryl carboxylic acid conjugate of hydrocodone. Suitable bases include but are not limited to: 4-methylmorpholine (NMM), 4-(dimethylamino)pyridine (DMAP), N,N-diisopropylethylamine, lithium bis(trimethylsilyl)amide, lithium diisopropylamide (LDA), any alkali metal tert.-butoxide (e.g., potassium tert.-butoxide), any alkali metal hydride (e.g., sodium hydride), any alkali metal alkoxide (e.g., sodium methoxide), triethylamine or any other tertiary amine.

Suitable solvents that can be used for any reaction in the synthetic scheme of an aryl carboxylic acid conjugate of hydrocodone include but are not limited to: acetone, acetonitrile, butanol, chloroform, dichloromethane, dimethylformamide (DMF), dimethylsulfoxide (DMSO), dioxane, ethanol, ethyl acetate, diethyl ether, heptane, hexane, methanol, methyl tert.-butyl ether (MTBE), isopropanol, isopropyl acetate, diisopropyl ether, tetrahydrofuran, toluene, xylene or water.

In some embodiments, the prodrug is hydrophobic and thus poorly water soluble. This results in a gel-like consistency or clumpy suspension when the compound is mixed with water. Examples of these prodrugs include, but are not limited to, Piperonylate-HC, 3-OH-4-MeO-Bz-HC, 3-OH-Bz-HC and Gallate-HC. These prodrugs cannot be dosed intranasally in rats due to their lack of water solubility. Not to be bound by any theory, it is assumed that these compounds would also congeal or become clumpy when a human subject tries to inhale them intranasally ("snorting"). This property would not only make an attempt of intranasal abuse an unpleasant experience but would likely also prevent the prodrug from permeating the nose mucosa. As a consequence, these compounds become ineffective for this route of administration.

The present technology provides pharmaceutical kits for the treatment or prevention of drug withdrawal symptoms or pain in a patient. The patient may be a human or animal patient. Suitable human patients include pediatric patients, geriatric (elderly) patients, and normative patients. The kit comprises a specific amount of the individual doses in a package containing a pharmaceutically effective amount of at least one conjugate of hydrocodone of the present technology. The kit can further include instructions for use of the kit. The specified amount of individual doses may contain from about 1 to about 100 individual dosages, alternatively from about 1 to about 60 individual dosages, alternatively from about 10 to about 30 individual dosages, including, about 1, about 2, about 5, about 10, about 15, about 20, about 25, about 30, about 35, about 40, about 45, about 50, about 55, about 60, about 70, about 80, about 100, and include any additional increments thereof, for example, 1, 2, 5, 10 and multiplied factors thereof, (e.g., ×1, ×2, ×2.5, ×5, ×10, ×100, etc.).

The presently described technology and its advantages will be better understood by reference to the following examples. These examples are provided to describe specific embodiments of the present technology. By providing these specific examples, it is not intended limit the scope and spirit of the present technology. It will be understood by those skilled in the art that the full scope of the presently described technology encompasses the subject matter defined by the claims appending this specification, and any alterations, modifications, or equivalents of those claims.

EXAMPLES

Example 1

Chemical Stability of Benzoate and Heteroaryl Carboxylate Conjugates of Hydrocodone Exemplary conjugates of hydrocodone of the present technology and control test conjugates not of the present technology were tested for chemical stability under conditions similar to what a potential drug abuser may use to "extract" the active portion of the molecule, for example dissolved in water, hydrochloric acid or sodium bicarbonate either at ambient temperature or 100° C. The conjugates were placed in a solution of water at either ambient temperature (about 20° C.) or in an oil bath at 100° C. for one hour and the amount of the conjugate that was hydrolyzed under these conditions was measured. Table 2 demonstrates the results, showing that the conjugates did not release hydrocodone at ambient temperature or when heated in water to 100° C. for one hour.

TABLE 2

| Compound | water$^a$ | |
| --- | --- | --- |
| | ambient | 100° C. |
| 4-OH-Bz-HC | 0% | 0% |
| 2-ABz-HC | 0% | 0% |
| 4-MeO-Bz-HC | 0% | 0% |

Further, samples of conjugates of hydrocodone of the present technology were tested and compared with samples of other conjugates not of the present technology of hydrocodone (Adipate-HC) for their hydrolysis to hydrocodone after dilution in 1 N hydrochloric acid (HCl) for 1 hour at ambient temperature (~20° C.) or in an oil bath at 100° C. The percentages indicate how much of the initial amount of conjugate was hydrolyzed under these conditions. The results are shown in Table 3.

TABLE 3

| Compound | %-release in 1N HCl$^a$ | |
| --- | --- | --- |
| | ambient | 100° C. |
| 4-OH-Bz-HC | 0% | 30% |
| 2-ABz-HC | 0% | 16% |
| 3-OH-4-MeO-Bz-HC | 0% | 35% |
| 2-OH-Bz-HC | 3% | 27% |
| Adipate-HC | 13% | 100% |

Samples of each conjugate were dissolved in a solution of 5% NaHCO$_3$ for one hour at either ambient temperature (~20° C.) or in an oil bath at 100° C. The percentages indicate how much of the initial amount of conjugate was hydrolyzed under these conditions as shown in Table 4 for the conjugates of the present technology and comparison conjugates not of the present technology (Tyr-Tyr-Phe-Phe-Ile-Hydrocodone (YYFFI-HC) or Adipate-HC).

TABLE 4

| Compound | %-release in 5% NaHCO$_3$$^a$ | |
| --- | --- | --- |
|  | ambient | 100° C. |
| 4-OH-Bz-HC | 1% | 23% |
| 3-OH-4-MeO-Bz-HC | 0% | 36% |
| YYFFI-HC | 0% | 70% |
| Adipate-HC | 3% | 100% |

Example 2

Oral PK Profiles of Conjugated Hydrocodone of the Present Technology

Figure 5:
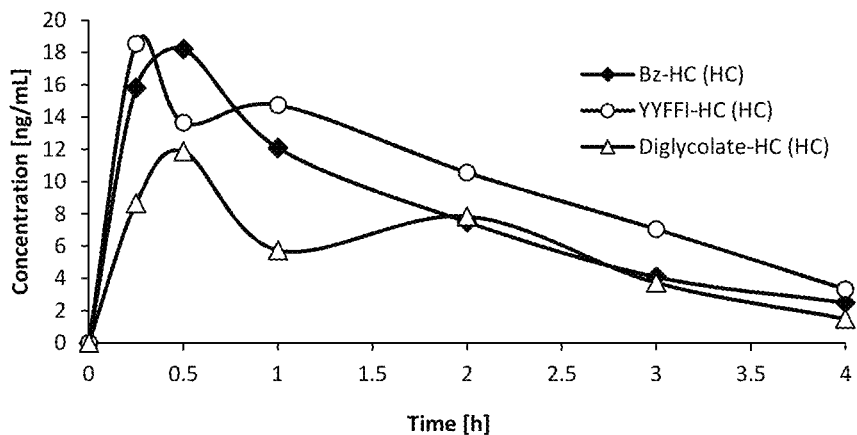
FIG. 5. PK profile graph of plasma concentrations of hydrocodone released from Bz-HC (benzoate-hydrocodone), YYFFI-HC (Tyr-Tyr-Phe-Phe-Ile-Hydrocodone) and Diglycolate-HC over time upon oral administration in rats.
Figure 6:
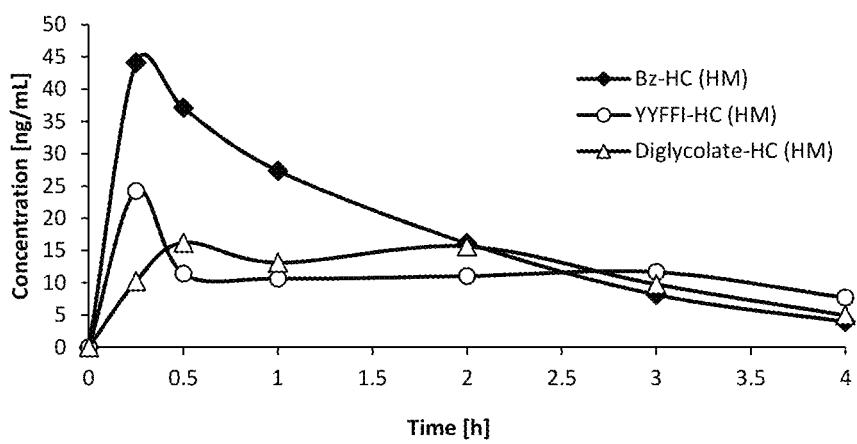
FIG. 6. PK profile graph of plasma concentrations of active metabolite hydromorphone over time upon oral administration of Bz-HC, YYFFI-HC, and Diglycolate-HC in rats.

Oral PK curves were determined for benzoate-hydrocodone (Bz-HC), a prodrug of the present technology, as compared to two conjugates not within the scope of the present technology: YYFFI-HC and Diglycolate-HC. Rats were orally administered an amount of the conjugate equivalent to 2 mg/kg of freebase hydrocodone and the plasma concentrations of released hydrocodone and of the active metabolite hydromorphone were measured over time by LC/MS/MS. As shown in FIG. 5, the oral PK curves for released hydrocodone were somewhat similar for Bz-HC and YYFFI-HC, but hydrocodone plasma concentrations produced by Bz-HC were mostly significantly higher than hydrocodone concentrations generated by Diglycolate-HC (AUC and C$_{max}$ for Bz-HC were approximately 40% and 50% higher, respectively). Additionally, Bz-HC created higher plasma concentrations of the more potent active metabolite hydromorphone (FIG. 6) than both, YYFFI-HC (AUC and C$_{max}$ for hydromorphone released from Bz-HC were approximately 60% and 80% higher, respectively) and Diglycolate-HC (AUC and C$_{max}$ for hydromorphone released from Bz-HC were approximately 55% and 180% higher, respectively). This suggests that all three compounds undergo a different metabolic pathway and that Bz-HC would have pain relieving effects potentially greater than either example.

Example 3

Intranasal PK Profile of Conjugates of Hydrocodone

Figure 7:
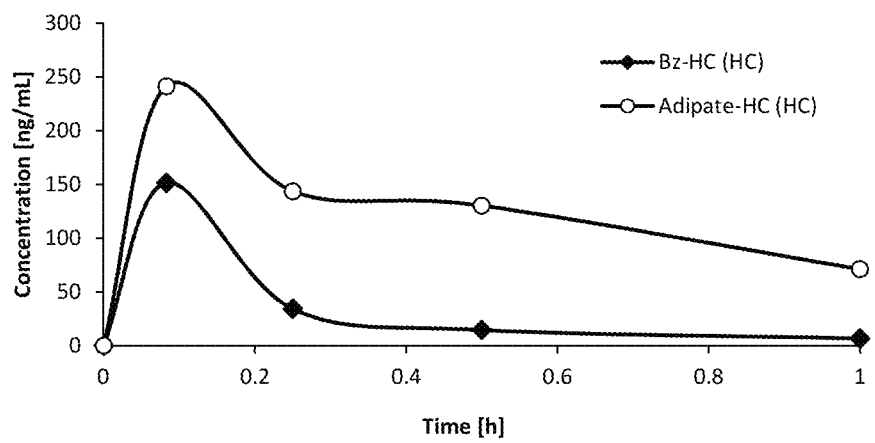
FIG. 7. PK profile graph of plasma concentrations of hydrocodone released from Bz-HC and Adipate-HC over time upon intranasal administration in rats.
Figure 8:
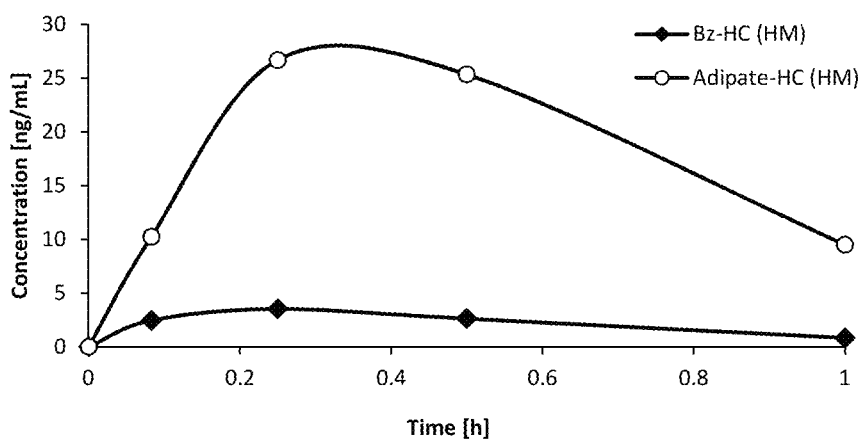
FIG. 8. PK profile graph of plasma concentrations of active metabolite hydromorphone over time upon intranasal administration of Bz-HC and Adipate-HC in rats.

Conjugates of hydrocodone of the present technology were tested for abuse resistance capabilities by examining the efficiency of a hydrolysis when administered via routes other than oral. Rats were intranasally treated with conjugate in an amount equivalent to 2 mg/kg of hydrocodone freebase and the concentration of released hydrocodone and of the active metabolite hydromorphone in the plasma of the rat were measured over time by LC/MS/MS. Hydrocodone plasma concentrations were significantly lower for Bz-HC (AUC and C$_{max}$ for hydromorphone released from Adipate-HC were approximately 280% and 60% higher, respectively) as shown in FIG. 7. Moreover, Bz-HC produced very low plasma concentration of hydromorphone when compared to Adipate-HC (AUC and C$_{max}$ for hydromorphone released from Adipate-HC were approximately 750% and 660% higher, respectively) as shown in FIG. 8.

Prodrugs of the present technology provide hydrocodone and hydromorphone plasma concentrations that are significantly lower than respective plasma concentration for unbound Hydrocodone.BT or for other prodrug classes when administered intranasally.

Example 4

Exemplary Intravenous PK Profiles of Conjugates of the Present Technology

The conjugates of hydrocodone of the present technology are hydrophobic, for example, Bz-HC, Nicotinate-HC, 4-MeO-Bz-HC, Piperonylate-HC, 4-OH-Bz-HC, Salicylate-HC, 3-OH-4-MeO-Bz-HC, 3-OH-Bz-HC and Gallate-HC. Therefore, these compounds cannot be administered intravenously at oral equivalent doses because they do not dissolve in a practical amount of water since injectable compounds must be completely in solution, because any solid particle may cause an embolism. The amount of water necessary to dissolve a desirable amount of conjugate would make an injection unfeasible and thus the present compositions and prodrugs have anti-abuse potential as opposed to other hydrocodone conjugates that are water soluble, such as Adipate-HC and Diglycolate-HC which can be administered intravenously at oral equivalent doses.

Example 5

Comparison of Oral PK Profiles of Conjugates of Hydrocodone

Figure 9:
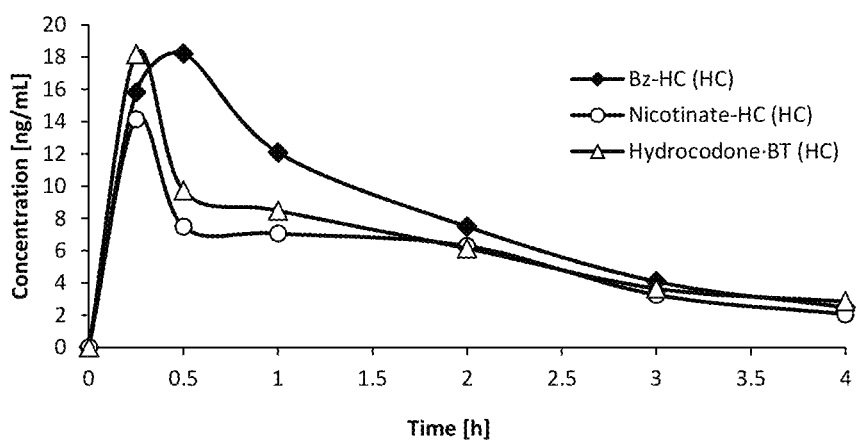
FIG. 9. PK profile graph of plasma concentrations of hydrocodone released from Bz-HC, Nicotinate-HC and Hydrocodone.BT over time upon oral administration in rats.
Figure 10:
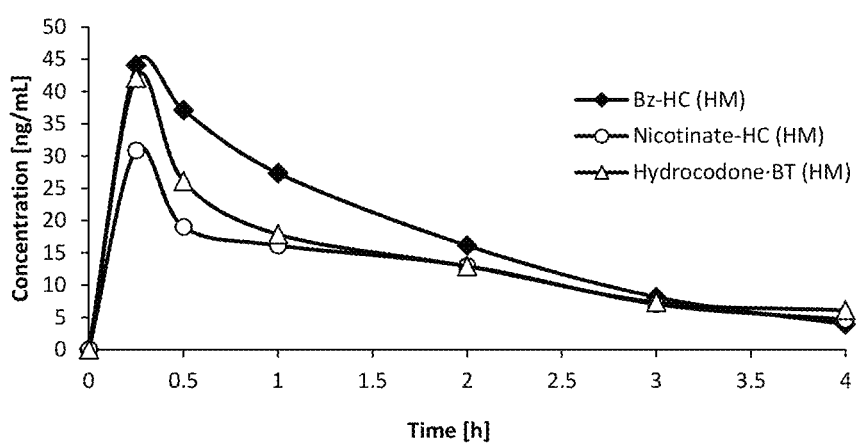
FIG. 10. PK profile graph of plasma concentrations of active metabolite hydromorphone over time upon oral administration of Bz-HC, Nicotinate-HC and Hydrocodone.BT in rats.

The plasma concentrations of hydrocodone released from Bz-HC and Nicotinate-HC were compared to plasma concentrations of hydrocodone generated by unconjugated Hydrocodone.BT after oral administration to rats. Rats were treated with conjugate or unconjugated drug in an amount equivalent to 2 mg/kg of hydrocodone freebase and the plasma concentration of hydrocodone or hydromorphone was measured by LC/MS/MS as demonstrated in FIGS. 9 and 10 respectively. The oral plasma concentration of hydrocodone released from Bz-HC increased similarly to the hydrocodone plasma concentrations observed with Hydrocodone.BT, until it reached C$_{max}$ (C$_{max}$ was approximately equal for both compounds). After T$_{max}$, the hydrocodone plasma concentration for Bz-HC decreased in a slower and more controlled fashion than for unconjugated Hydrocodone.BT (FIG. 9 and FIG. 10). Bz-HC had a higher AUC (AUC was approximately 25% higher, FIG. 9) when compared to Hydrocodone.BT and similar results were observed for the plasma concentrations of the active metabolite hydromorphone (FIG. 10).

Nicotinate-HC, produced hydrocodone and hydromorphone plasma concentrations that were below the respective concentrations found for unconjugated Hydrocodone.BT. The corresponding AUC values, however, were within the range of bioequivalence for the same dose (based on hydrocodone freebase).

Figure 11:
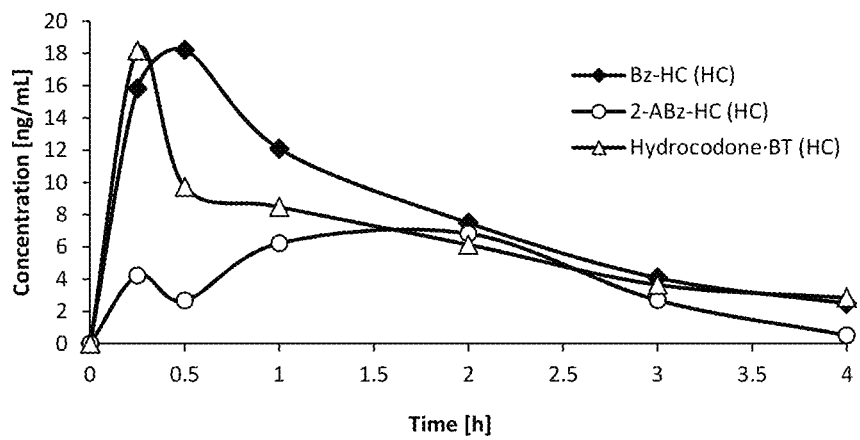
FIG. 11. PK profile graph of plasma concentrations of hydrocodone released from Bz-HC, 2-ABz-HC and Hydrocodone.BT over time upon oral administration in rats.
Figure 12:
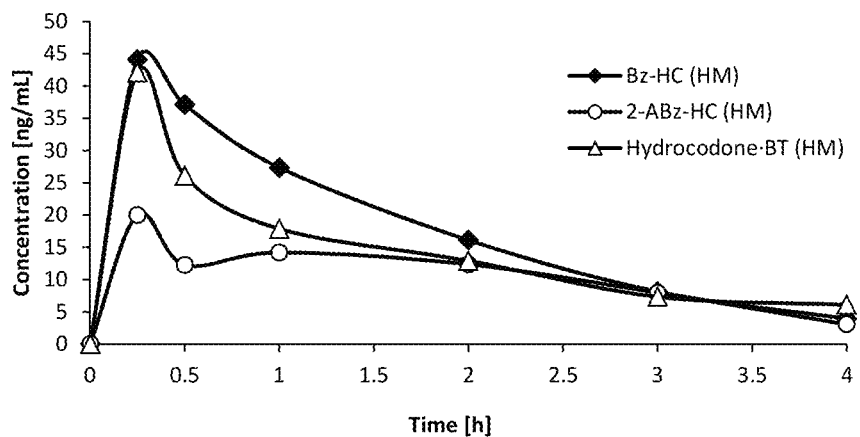
FIG. 12. PK profile graph of plasma concentrations of active metabolite hydromorphone over time upon oral administration of Bz-HC, 2-ABz-HC and Hydrocodone.BT in rats.

2-ABz-HC demonstrated a different release profile after oral administration to rats than Bz-HC or the unconjugated drug Hydrocodone.BT. Rats were treated with an amount equivalent to 2 mg/kg of hydrocodone freebase and the plasma concentration of hydrocodone or hydromorphone was measured by LC/MS/MS over time as shown in FIG. 11 or FIG. 12 respectively. 2-ABz-HC released hydrocodone very slowly indicated by a gradual increase of plasma concentration followed by an attenuated decrease (FIG. 11). This resulted in a flattened PK curve when compared with Hydrocodone.BT (T$_{max}$ for 2-ABz-HC was approximately four times longer, AUC and C$_{max}$ were approximately 35% and 60% lower, respectively). Overall, the PK curve of hydromorphone was also flatter for 2-ABz-HC than for Hydrocodone.BT (FIG. 12) but did show a small initial spike (AUC and $C_{max}$ for 2-ABz-HC were approximately 25% and 50% lower, respectively).

Example 6

Determination of Variation in Plasma Concentrations of Benzoate-Hydrocodone

To determine the variability of the plasma concentration of hydrocodone (HC) and hydromorphone (HM), the coefficient of variation (CV) was calculated for individual animals that were dosed with an amount equivalent to 2 mg/kg of hydrocodone freebase of benzoate-hydrocodone or the unconjugated hydrocodone bitartrate (BT) and the plasma concentrations of hydrocodone and hydromorphone were measured by LC/MS/MS over time. The CV was calculated by dividing the standard deviation of plasma concentrations in individual animals by the mean plasma concentrations of all dosed animals for a given time point. The "average CV" is the mean CV for all time points, as shown in Table 5.

TABLE 5

| Compound | Average CV$^a$ | |
|---|---|---|
| | HC | HM |
| Bz-HC | 46 | 41 |
| Hydrocodone•BT | 75 | 64 |

The lower average CV for Bz-HC indicates that this prodrug has lower relative variability in plasma concentrations of hydrocodone and hydromorphone across all dosed animals and time points than the unconjugated drug, hydrocodone bitartrate.

Example 7

Synthesis of Conjugates of Hydrocodone

Synthesis of Benzoate-Hydrocodone Freebase

To a solution of hydrocodone freebase (0.596 g, 1.99 mmol) in tetrahydrofuran (25 mL) was added 1 M LiN(SiMe$_3$)$_2$ in tetrahydrofuran (5.98 mL). The resulting orange suspension was stirred at ambient temperatures for 30 min. after which benzoate-succinic ester (1.25 g, 5.98 mmol) was added. The resulting mixture was stirred overnight at ambient temperatures and was quenched after 18 h by the addition of 100 mL saturated ammonium chloride solution which was allowed to stir for another 2 h. Ethyl acetate (100 mL) was added to the mixture and washed with saturated ammonium chloride solution (3×100 mL) and water (1×100 mL). Organic extracts were dried over anhydrous MgSO$_4$, solvent was removed and residue was taken up in 2-isopropanol (50 mL). Water was added until a solid formed. The resulting mixture was chilled, filtered and dried to obtain benzoate-hydrocodone freebase (0.333 g, 0.826 mmol, 42% yield) as a dark brown solid. This synthesis is depicted in FIG. 13A.

Synthesis of 2-Boc-aminobenzoic succinate

2-Boc-aminobenzoic acid (2.56 g, 10.8 mmol) and N-hydroxysuccinimide (1.37 g, 11.88 mmol) were dissolved in 25 mL of THF. DCC (2.45 g, 11.88 mmol) was added in one portion. The reaction was stirred overnight. The solid was filtered off and rinsed with acetone (2×10 mL). The filtrate was concentrated to dryness and dissolved in 100 mL of acetone. The resulting precipitate (DCU) was filtered off and the filtrate was concentrated to give a solid, which was collected and rinsed with methanol (3×4 mL) to yield 3.26 g (90%) of white product.

Synthesis of 2-Boc-aminobenzoic acid ester of hydrocodone

To hydrocodone freebase (0.449 g, 1.5 mmol) dissolved in 20 mL of anhydrous THF was added a solution of LiHMDS in THF (1 M, 4.5 mL, 4.5 mmol) over 20 min. The mixture was stirred for 30 min. and 2-Boc-aminobenzoic succinate (1.50 g, 4.5 mmol) was added in one portion. The reaction was stirred for 4 hours and subsequently quenched with 100 mL of sat. NH$_4$Cl. The mixture was stirred for 1 h. and extracted with 200 mL of ethyl acetate. The ethyl acetate layer was washed with sat. NaHCO$_3$ (2×80 mL) and 5% brine (80 mL), dried over anhydrous Na$_2$SO$_4$ and concentrated. The residue was purified by silica gel column chromatography (7% MeOH/CH$_2$Cl$_2$) to give 449 mg (58%) of an amorphous solid.

Synthesis of 2-aminobenzoic acid ester of hydrocodone dihydrochloride salt

2-Boc-aminobenzoic acid ester of hydrocodone (259 mg, 0.5 mmol) was stirred in 4 mL of 4 N HCl/dioxane for 4 h. The solvent was evaporated to dryness and to the residue was added 5 mL of ethyl acetate. The solid was collected and rinsed with ethyl acetate to give 207 mg (84%) of product.

Synthesis of 2-MOM-salicylic succinate

2-MOM-salicylic acid (3.2 g, 17.6 mmol) and N-hydroxysuccinimide (2.23 g, 19.36 mmol) were dissolved in 40 mL of THF. DCC (3.99 g, 19.36 mmol) was added in one portion. The reaction was stirred overnight. The solid was filtered off and rinsed with acetone (2×10 mL). The filtrate was concentrated and the residue was recrystallized from 10 mL of methanol to give 2.60 g (53%) of a white solid.

Synthesis of 2-MOM-salicylic acid ester of hydrocodone

To hydrocodone freebase (0.449 g, 1.5 mmol) dissolved in 20 mL of anhydrous THF was added a solution of LiHMDS in THF (1 M, 4.5 mL, 4.5 mmol) over 20 min. The mixture was stirred for 30 min. and 2-MOM-salicylic succinate (1.26 g, 4.5 mmol) was added in one portion. The reaction was stirred for 4 h. and subsequently quenched with 100 mL of sat. NH$_4$Cl. The mixture was stirred for 1 h. and extracted with 200 mL of ethyl acetate. The ethyl acetate layer was washed with sat. NaHCO$_3$ (2×80 mL) and 5% brine (80 mL), dried over anhydrous Na$_2$SO$_4$ and concentrated. The residue was purified by silica gel column chromatography (8% MeOH/CH$_2$Cl$_2$) to give 381 mg (58%) of a syrup.

Synthesis of Salicylic Acid Ester of Hydrocodone Hydrochloride Salt

To 2-MOM-salicylic acid ester of hydrocodone (380 mg, 0.82 mmol) in 12 mL of methanol was added 0.5 mL of conc. HCl (12 N). The reaction was stirred for 6 hr. The solution was concentrated and residual water was removed by coevaporating with methanol (5×5 mL). The resulting residue was dissolved in 1 mL of methanol followed by 20 mL of ethyl acetate. The cloudy mixture was evaporated to about 4 mL. The resulting solid was collected and rinsed with ethyl acetate to yield 152 mg (41%) of product.

Example 8

Figure 14:
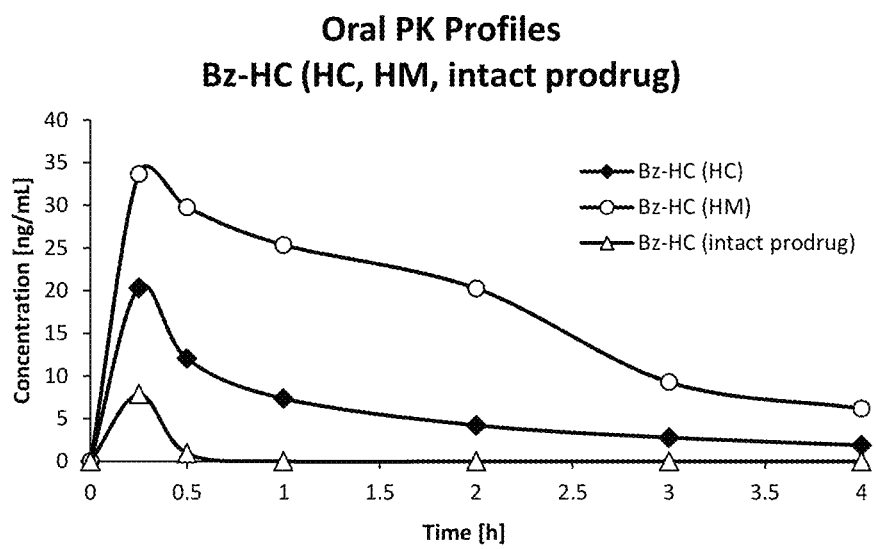
FIG. 14. PK profile graph of plasma concentrations of intact Bz-HC, active metabolite hydromorphone and of hydrocodone released from Bz-HC over time upon oral administration in rats.

Oral PK Profiles of Conjugated Hydrocodone, Hydrocodone, and Hydromorphone in Rats After oral administration of benzoate-hydrocodone (Bz-HC) to rats, PK curves were determined for intact Bz-HC, hydrocodone, and the active metabolite hydromorphone. Rats were orally administered an amount of the conjugate equivalent to 2 mg/kg of freebase hydrocodone and the plasma concentrations of intact Bz-HC, released hydrocodone, and the active metabolite, hydromorphone, were measured over time by LC/MS/MS. As shown in FIG. 14, the exposure to intact Bz-HC prodrug was much lower than the exposure to hydrocodone or hydromorphone (the AUC for intact Bz-HC was approximately 10% and 3% of the AUC values for hydrocodone and hydromorphone, respectively).

Example 9

Oral PK Profiles of Conjugated Hydrocodone, Hydrocodone, and Hydromorphone in Dogs After oral administration of benzoate-hydrocodone (Bz-HC) or Hydrocodone.BT to dogs, PK curves were determined for intact Bz-HC (Bz-HC arm only), hydrocodone, and the active metabolite hydromorphone. Dogs were orally administered an amount of Hydrocodone.BT or the conjugate equivalent to 2 mg/kg of freebase hydrocodone. The plasma concentrations of intact Bz-HC, released hydrocodone, and the active metabolite, hydromorphone, were measured over time by LC/MS/MS.

Figure 15:
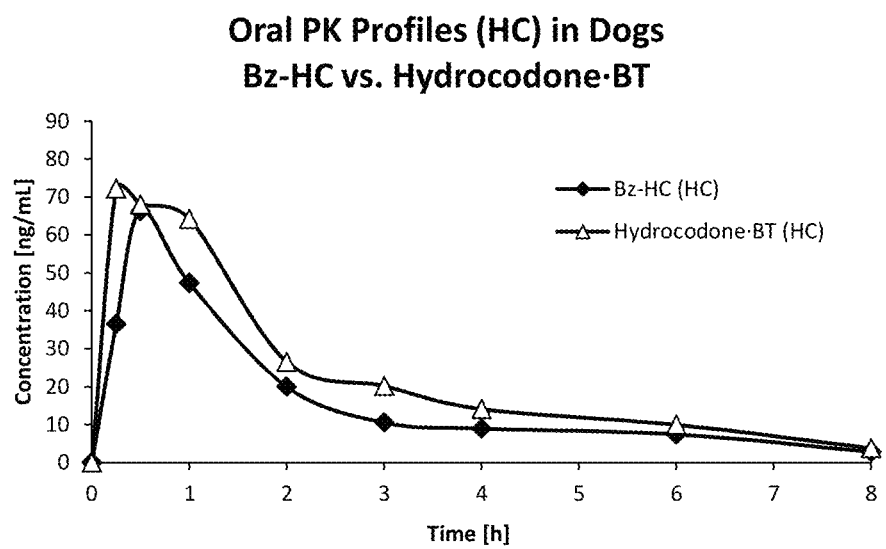
FIG. 15. PK profile graph of plasma concentrations of hydrocodone released from Bz-HC and hydrocodone.BT over time upon oral administration in dogs.

A comparison of plasma concentrations of hydrocodone released from Bz-HC and Hydrocodone.BT is shown in FIG. 15. Overall, the plasma concentrations of hydrocodone generated by both compounds were quite similar. The systemic exposure to hydrocodone was somewhat reduced for Bz-HC when compared to Hydrocodone.BT (the AUC value of hydrocodone for Bz-HC was approximately 72% of the AUC value for Hydrocodone.BT). The $C_{max}$ value of hydrocodone for Bz-HC was approximately 92% of the $C_{max}$ value for Hydrocodone.BT.

Figure 16:
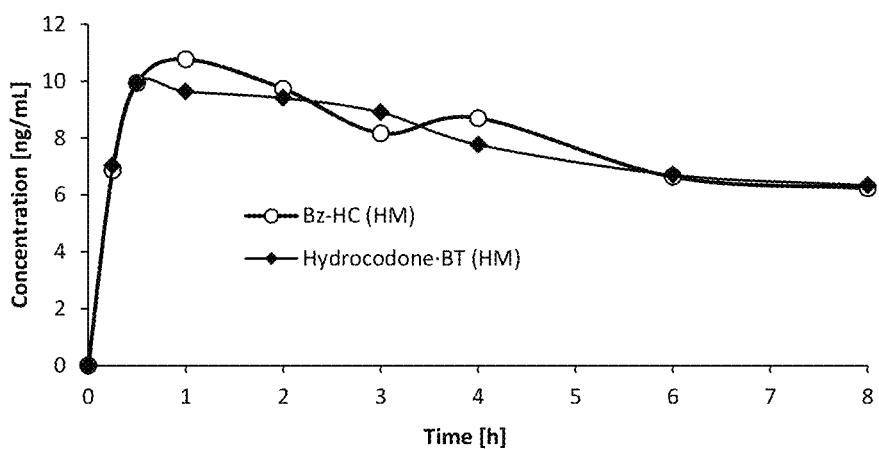
FIG. 16. PK profile graph of plasma concentrations of active metabolite hydromorphone over time upon oral administration of Bz-HC and hydrocodone.BT in dogs.
Figure 17:
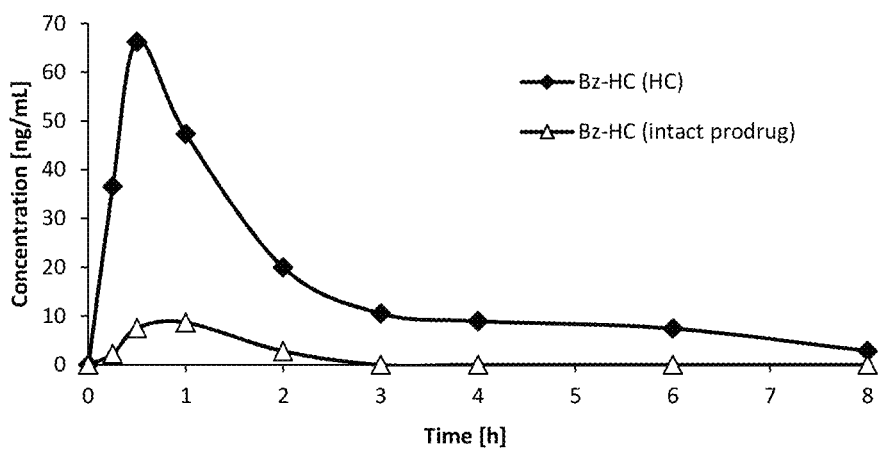
FIG. 17. PK profile graph of plasma concentrations of intact Bz-HC and of hydrocodone released from Bz-HC over time upon oral administration in dogs.

A comparison of the plasma concentrations of the active metabolite, hydromorphone, following oral administration of Bz-HC or Hydrocodone. BT is shown in FIG. 16. Systemic exposure and maximum plasma concentrations of hydromorphone were similar for both compounds. The AUC and $C_{max}$ values of hydromorphone for Bz-HC were approximately 103% and 109% of the respective values for Hydrocodone.BT A comparison the plasma concentrations of intact Bz-HC and hydrocodone released from Bz-HC is shown in FIG. 17. Similar to the results seen in rats, the plasma concentrations of intact Bz-HC prodrug in dogs were low when compared to the plasma concentrations of hydrocodone (the AUC value for intact Bz-HC was approximately 10% of the AUC value for hydrocodone).

Example 10

Figure 18:
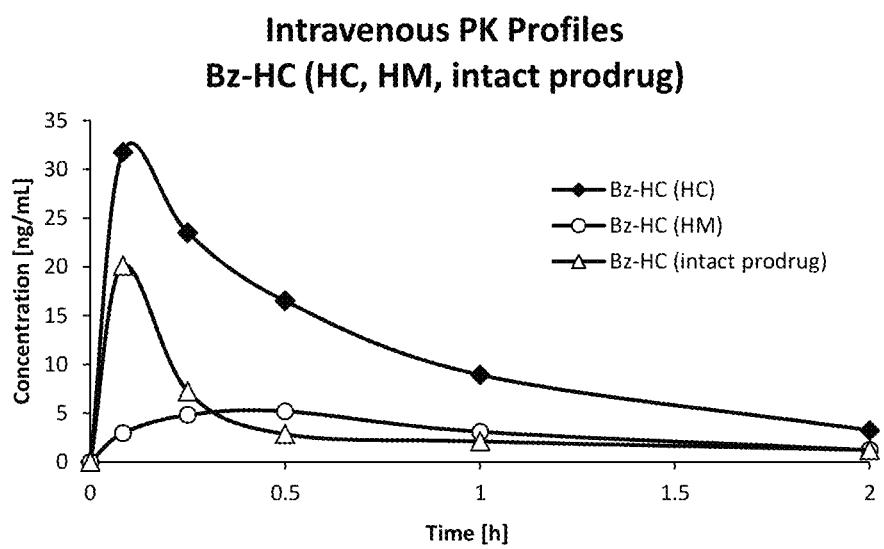
FIG. 18. PK profile graph of plasma concentrations of intact Bz-HC, active metabolite hydromorphone and of hydrocodone released from Bz-HC over time upon intravenous administration in rats at 0.30 mg/kg.

Intravenous PK Profiles of Conjugated Hydrocodone, Hydrocodone, and Hydromorphone in Rats Bz-HC (0.30 mg/kg) was administered intravenously to rats. Due to its poor water solubility (or solubility in PBS), 0.30 mg/kg was close to the maximum dose that could be administered intravenously to rats. PK curves were determined for intact Bz-HC, hydrocodone, and the active metabolite hydromorphone. The plasma concentrations of intact Bz-HC, released hydrocodone, and the active metabolite, hydromorphone, were measured over time by LC/MS/MS. The resulting PK curves are shown in FIG. 18.

Example 11

Figure 19:
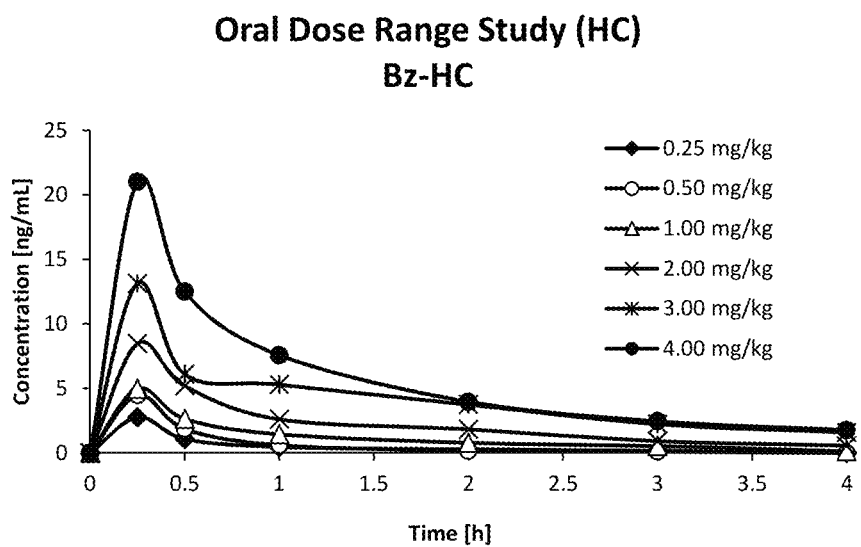
FIG. 19. PK profile graph of plasma concentrations of hydrocodone released from Bz-HC over time upon oral administration in rats at six different dosages.
Figure 20:
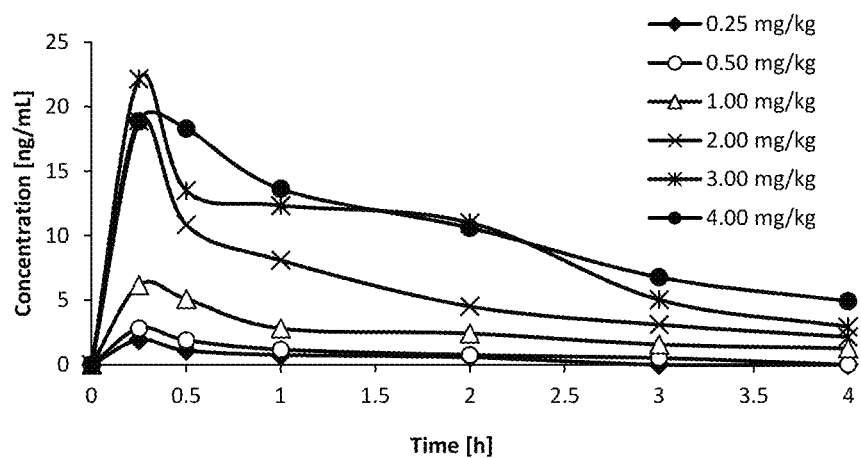
FIG. 20. PK profile graph of plasma concentrations of active metabolite hydromorphone over time upon oral administration of Bz-HC in rats at six different dosages.

Oral PK Profiles of Hydrocodone and Hydromorphone Following Various Dosages of Bz-HC in Rats Bz-HC was orally administered to rats at dosages of 0.25, 0.50, 1.00, 2.00, 3.00, or 4.00 mg/kg. The plasma concentrations of hydrocodone or hydromorphone were measured by LC/MS/MS, as demonstrated in FIGS. 19 and 20, respectively. The exposures (AUC) to hydrocodone and hydromorphone at doses of Bz-HC between 0.25 and 4.00 mg/kg were fairly linear. The respective $C_{max}$ values, however, were more variable, particularly for hydromorphone. The maximum plasma concentrations of hydromorphone did not significantly change at doses above 2.00 mg/kg of Bz-HC.

Example 12

Tamper Resistance

In order to further evaluate the tamper-resistant properties of Bz-HC, a wide variety of Bz-HC solvent extraction studies were performed. Bz-HC.HCl is soluble in various solvents, but dissolving Bz-HC.HCl in solution only yields the inactive prodrug in solution. The prodrug is not cleaved and no hydrocodone becomes available. Bz-HC.HCl is much less soluble in water than the hydrocodone bitartrate that is used in certain hydrocodone bitartrate/APAP combination products. In addition, at the human physiological pH of 7.4 (blood), Bz-HC is highly insoluble. We also conducted a wide variety of Bz-HC solvent hydrolysis studies in our own laboratories. As shown in Table 6 below, our studies indicate that Bz-HC is completely stable and will not hydrolyze in commonly available solvents, and is stable to conditions that hydrolyze other formulated abuse-deterrent drugs (e.g., water and alcohol, with or without heating).

Solvent Hydrolysis: No Hydrocodone Release

TABLE 6

| | %-release of Hydrocodone | | | | | |
|---|---|---|---|---|---|---|
| | Ambient Temperature | | | at Boiling Point | | |
| Solvent | 0.5 h | 1 h | 4 h | 0.5 h | 1 h | 4 h |
| Water | 0 | 0 | 0 | 0 | 0 | 0 |
| Ethanol | 0 | 0 | 0 | 0 | 0 | 0 |
| Methanol | 0 | 0 | 0 | 0 | 0 | 0 |
| Acetone | 0 | 0 | 0 | 0 | 0 | 0 |
| Ethyl acetate | 0 | 0 | 0 | 0 | 0 | 0 |
| Toluene | 0 | 0 | 0 | 0 | 0 | 0 |
| Xylene | 0 | 0 | 0 | 0 | 0 | 0 |
| Tetrahydrofuran | 0 | 0 | 0 | 0 | 0 | 0 |
| Methyl ethyl ketone | 0 | 0 | 0 | 0 | 0 | 0 |
| Octane | 0 | 0 | 0 | 0 | 0 | 0 |
| Petrol ether | 0 | 0 | 0 | 0 | 0 | 0 |

In addition, real-world studies that used typical drug abuser-accessible solvents and methodologies, as well as a simulated smoking study were performed. No hydrocodone release from the prodrug was observed in any of these studies.

Finally, numerous enzymatic tampering studies were performed on Bz-HC, utilizing enzymes that included trypsin, pancreatin, pepsin and various esterases, and no significant release of hydrocodone from the prodrug was observed. Without being bound by theory, it is believed that metabolism of Bz-HC after oral administration that allows for the rapid release of therapeutic amounts of hydrocodone requires the combinations and processes of the esterases and other enzymes functioning in the living enterocytes and liver tissue inside the body.

These tamper-resistance studies, demonstrate that Bz-HC is very difficult to tamper with and is stable under conditions that can potentially defeat other abuse-deterrent technologies.

Example 13

Reduction of Opioid-Induced Constipation (OIC)

Opioid-induced constipation (OIC) is a common side effect of pain treatment with opioids and affects approximately 40% of patients who are chronically taking opioid medications. Without being bound by theory, it is believed that the binding of opioid agonists to the peripheral p-opioid receptors in the GI tract is the primary cause of OIC. This p-opioid receptor activation impairs the coordination of the GI function resulting in various effects on the GI tract, including decreasing the gut's motility, increasing nonpropulsive contractions of the circular muscles, increasing fluid absorption, reducing forward contractions and increasing anal sphincter tone. The clinical presentation of these effects typically manifests itself in symptoms of hard/dry stool, straining, incomplete evacuation, bloating and abdominal distension.

Although Bz-HC is metabolized to hydrocodone after oral administration, the prodrug itself has a very low binding affinity to the p-opioid receptors and, without being bound by theory, it is believed that Bz-HC does not interact with the p-opioid receptors in the GI tract.

Figure 21:
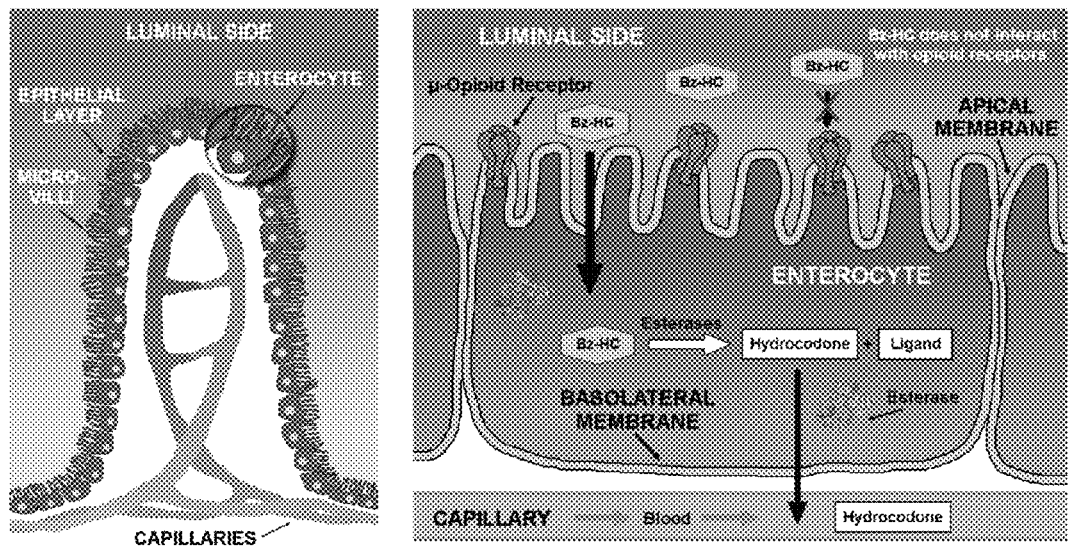
FIG. 21. Possible mechanism by which Bz-HC may minimize the side effect of OIC.

Without being bound by theory, a possible mechanism by which Bz-HC may minimize the side effect of OIC is illustrated by in FIG. 21. It is believed that due to its low binding affinity to the p-opioid receptors located on the inside of the intestine, Bz-HC is completely absorbed fully intact into the intestinal enterocytes where it is hydrolyzed down to hydrocodone and the ligand. It is also believed that the intestinal p-opioid receptors never come in contact with significant concentrations of hydrocodone, thus minimizing OIC.

Figure 22:
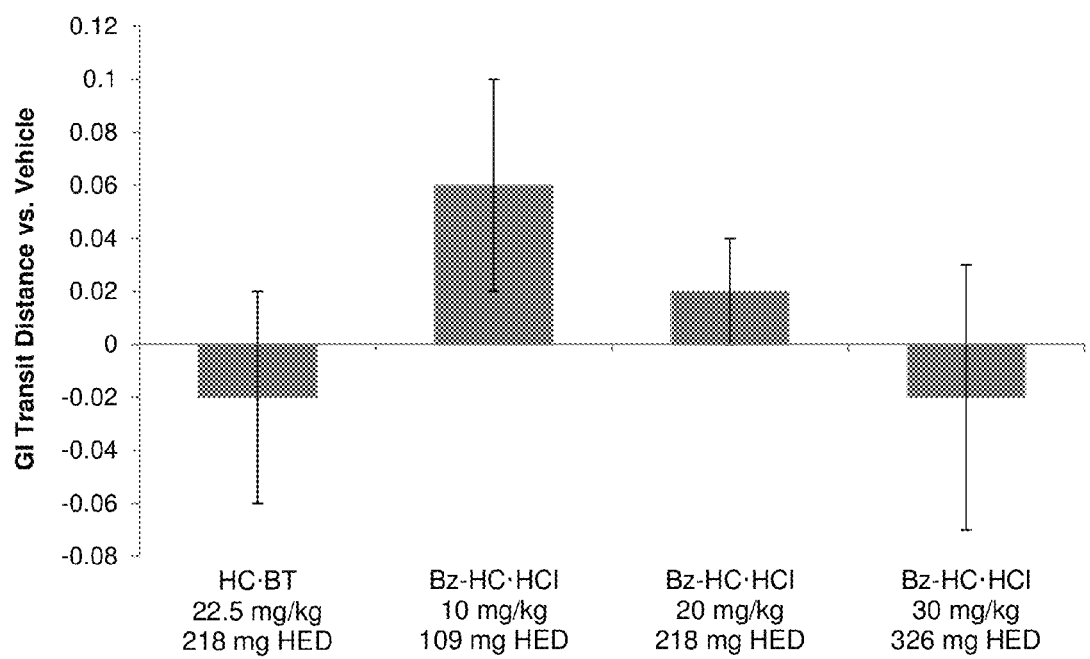
FIG. 22. Gastrointestinal motility study demonstrating increase/decrease gastrointestinal transit distance in rats treated with hydrocodone bitartrate (HC. BT) and benzoate-hydrocodone hydrochloride (Bz-HC.HCl) compared to rats treated with vehicle (water).

First, a GI motility study was performed three groups of 10 rats that were each dosed with Bz-HC.HCl at 10, 20 and 30 mg/kg, respectively. Another group of ten rats received 22.5 mg/kg of hydrocodone bitartrate and a fifth group of ten rats was administered the study vehicle, water, as a control. The doses administered of Bz-HC.HCl and hydrocodone bitartrate were very high on a human equivalent dosage basis, as normal human equivalent doses typically have no effect on rat GI motility. Each of the rats was then fed a meal of activated charcoal and then, 30 minutes later, GI motility was measured based on the distances the charcoal meals had traveled through the rats' GI tracts. As indicated in FIG. 22, GI motility was increased. Without being bound by theory, it is believed that this observation may be explained by the fact that the Bz-HC doses represented such large volumes inside the rats that, in the absence of a μ-opioid receptor mitigated OIC effect, the Bz-HC had acted like dietary fiber and increased GI motility.

Figure 23:
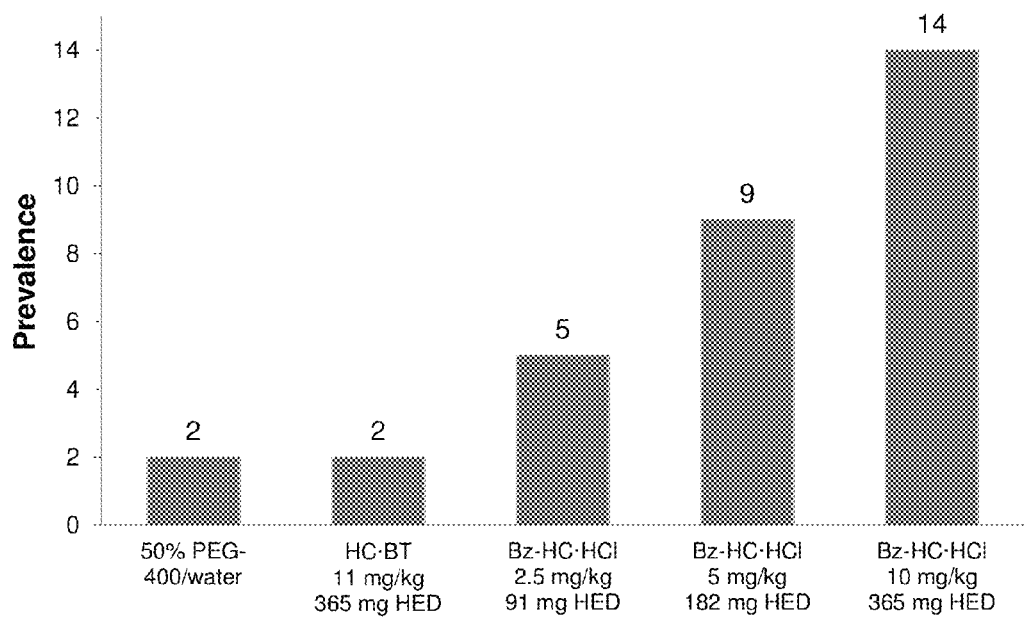
FIG. 23. Opioid-induced constipation study of post-dose prevalence of soft/loose feces after oral administration of hydrocodone bitartrate (HC.BT) and benzoate-hydrocodone hydrochloride (Bz-HC.HCl) in dogs.

A subsequent 14-day oral repeat dose toxicity study in dogs (beagle) was performed. This study indicated a higher prevalence of post-dose soft or loose feces in animals dosed with Bz-HC.HCl compared to hydrocodone bitartrate (FIG. 23). These studies indicate that Bz-HC reduces OIC when compared to other hydrocodone containing products.

Description of Bioanalytical Methods Used in Examples 14-19

Validated LC/MS/MS methods were used to measure plasma concentrations of Bz-HC, hydrocodone, hydromorphone and acetaminophen (APAP). The lower limits of quantitation (LLOQ) for Bz-HC, hydrocodone, hydromorphone, and APAP in plasma were 25 pg/mL, 250 pg/mL, 25 pg/mL, and 0.025 μg/mL, respectively.

Description of Pharmacokinetic and Statistical Analysis Conducted in Examples 14-19

Actual blood sampling collection times were used in all PK analyses. Per protocol times were used to calculate mean plasma concentrations for graphical displays. Pharmacokinetic parameters for hydrocodone, hydromorphone, and APAP were calculated using standard equations for non-compartmental analysis. Only plasma concentrations that were greater than the LLOQs for the respective assays were used in the pharmacokinetic analysis. Data were compared using the standard ANOVA model applied to the natural logarithms of the data.

Example 14

Bz-HC Human Pharmacokinetic Studies

Forty-two (42) healthy volunteers were enrolled in a single dose pharmacokinetic study. Subjects received a single dose of either 1 capsule of Bz-HC.HCl capsule, 5 mg (22 volunteers), 2 capsules of Bz-HC.HCl, 5 mg (20 volunteers) or 1 tablet of Norco® (hydrocodone bitartrate/acetaminophen, NDC # 52544-539-01), 10 mg/325 mg (21 volunteers) orally. All study doses were administered after a standard overnight fast (approximately 10 hours). The plasma concentrations of hydrocodone were measured by LC/MS/MS. The PK data and is summarized in Tables 7 and 8. These results show that at equimolar doses Bz-HC.HCl is bioequivalent and thus therapeutically equivalent to Norco® and similar immediate release hydrocodone combination products.

Single oral dose of 5 mg of Bz-HC.HCl summary:

TABLE 7

| Parameter | Hydrocodone Released from Bz-HC•HCl |
|---|---|
| $AUC_{0-24\ h}$ | 70.69 h × ng/mL ± 17.39 h × ng/mL |
| $AUC_{inf}$ | 79.37 h × ng/mL ± 18.67 h × ng/mL |
| $C_{max}$ | 12.8 ng/mL ± 3.84 ng/mL |
| $T_{max}$ (mean) | 1.866 h ± 0.901 h |
| $T_{max}$ (median) | 1.5 h |
| $T_{max}$ (range) | [0.5 h-4 h] |
| $t_{1/2}$ | 3.79 h ± 0.88 h |

Single oral dose of 10 mg of Bz-HC.HCl summary:

TABLE 8

| Parameter | Hydrocodone Released from Bz-HC•HCl |
|---|---|
| $AUC_{0-24\,h}$ | 165.4 h × ng/mL ± 42.35 h × ng/mL |
| $AUC_{inf}$ | 172.5 h × ng/mL ± 43.44 h × ng/mL |
| $C_{max}$ | 24.7 ng/mL ± 6.43 ng/mL |
| $T_{max}$ (mean) | 1.700 h ± 0.880 h |
| $T_{max}$ (median) | 1.5 h |
| $T_{max}$ (range) | [0.5 h-4 h] |
| $t_{1/2}$ | 4.36 h ± 0.81 h |

Example 15

Bz-HC.HCl/APAP Single Dose Human Pharmacokinetic Studies

A study, was conducted to determine the rate and extent of absorption of hydrocodone, hydromorphone, and acetaminophen (APAP) from Bz-HC.HCl/APAP tablets (1×6.67 mg/325 mg) relative to Norco® tablets (1×7.5 mg/325 mg, NDC #52544-162-01) when administered to healthy subjects under fasted conditions.

This was an open-label, single-dose, randomized, 2-treatment, 2-period, 2-sequence, crossover bioavailability study in which 30 healthy adult subjects were to be enrolled with the goal of completing 24. Subjects received two single-dose treatments according to a randomization schedule. Each treatment was separated by at least a 7-day washout period. All study doses were administered after a standard overnight fast (approximately 10 hours). Each dose was administered along with approximately 240 mL (8 fl. oz.) of room temperature tap water. No food was allowed until 4 hours after dose administration. Except for the 240 mL of room temperature tap water provided with the dose, no water was consumed for 1 hour prior through 1 hour after dosing.

Blood samples (2×6 mL) for pharmacokinetic analysis were collected prior to and up to 24 hours after each dose.

A total of 30 subjects were enrolled and 23 subjects completed both periods of the study to comprise the pharmacokinetic (PK) analysis population.

Figure 24:
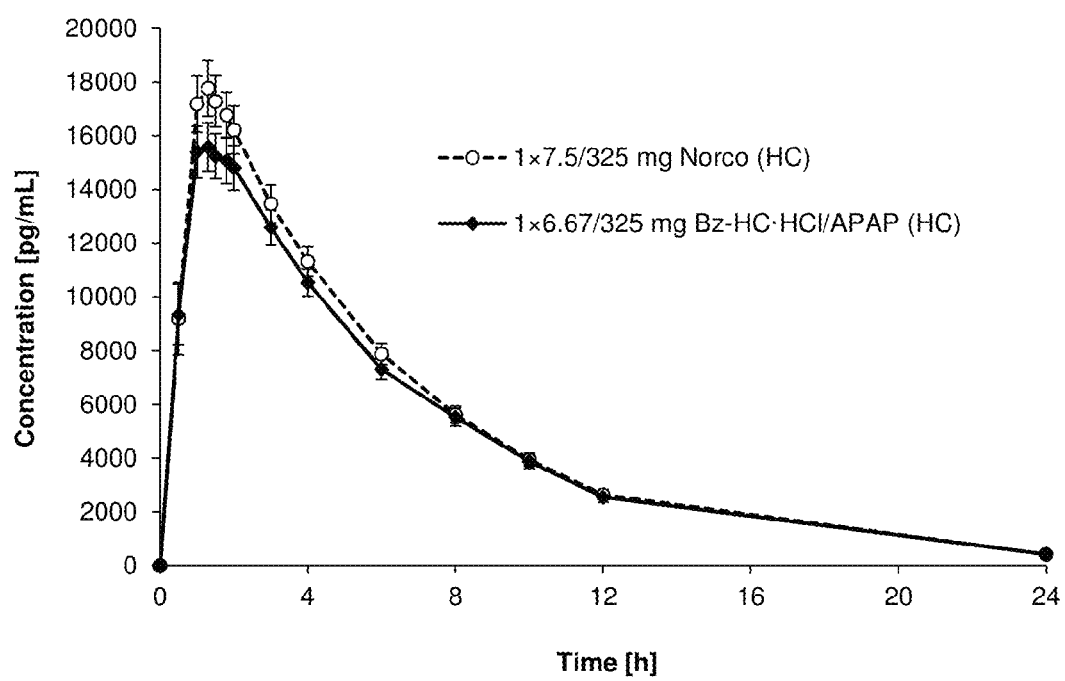
FIG. 24. PK profile graph of plasma concentrations of hydrocodone released from Bz-HC.HCl/APAP (6.67 mg/325 mg) and Norco® over time upon single dose, oral administration in fasted humans.
Figure 25:
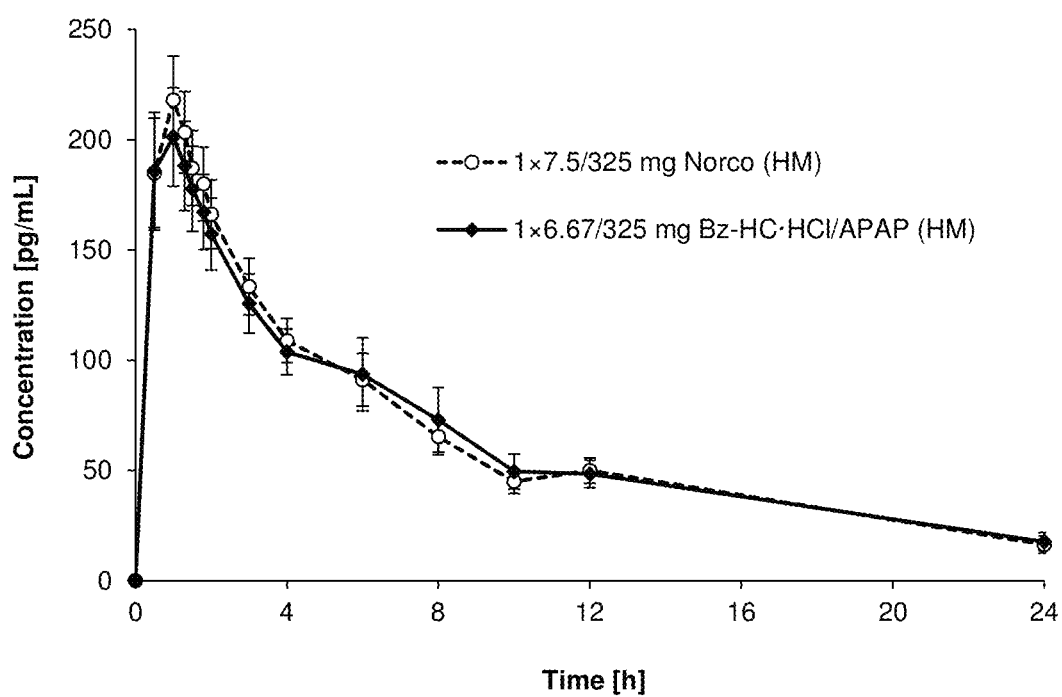
FIG. 25. PK profile graph of plasma concentrations of hydromorphone released from Bz-HC.HCl/APAP (6.67 mg/325 mg) and Norco® over time upon single dose, oral administration in fasted humans.
Figure 26:
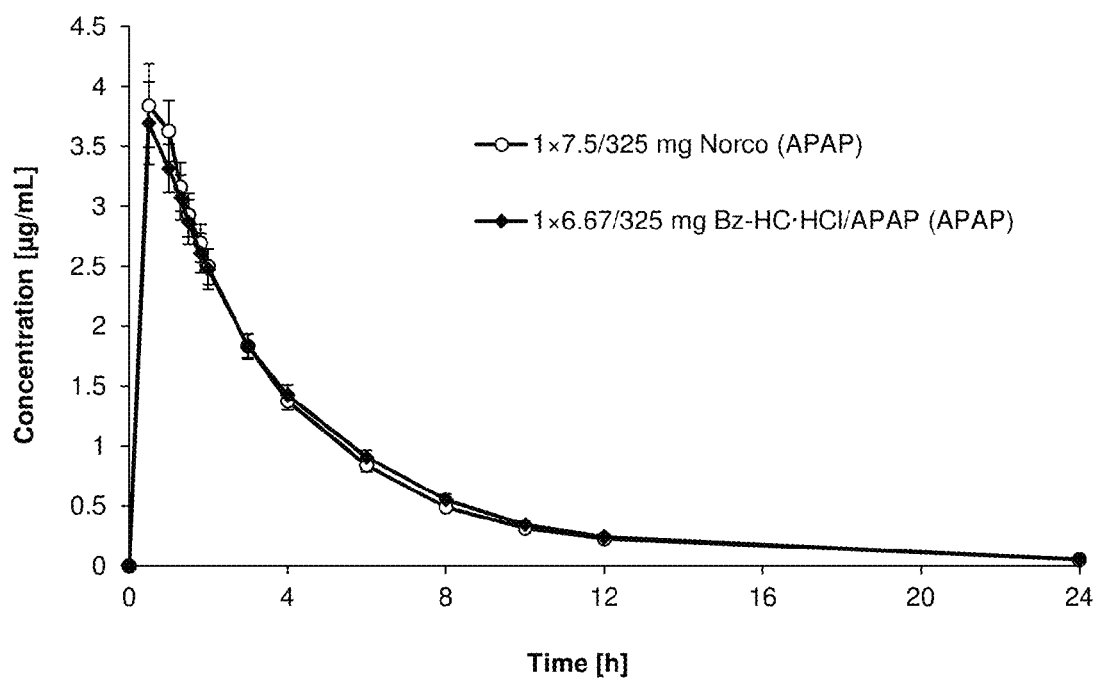
FIG. 26. PK profile graph of plasma concentrations of acetaminophen released from Bz-HC.HCl/APAP (6.67 mg/325 mg) and Norco® over time upon single dose, oral administration in fasted humans.

A summary of the PK data for hydrocodone, hydromorphone and acetaminophen is presented in Tables 9, 10, and 11. PK curves of the of the mean±standard error plasma concentrations of hydrocodone, hydromorphone and acetaminophen are presented in FIGS. 24, 25, and 26, respectively. These results demonstrate that Bz-HC.HCl/APAP (6.67 mg/325 mg) is bioequivalent and thus therapeutically equivalent to Norco® (7.5 mg/325 mg) and similar immediate release hydrocodone combination.

Hydrocodone Summary:
single dose; Bz-HC.HCl/APAP tablet, 6.67 mg/325 mg; oral; fasted

TABLE 9

| Parameter | Hydrocodone Released from Bz-HC•HCl/APAP |
|---|---|
| $AUC_{0-24\,h}$ | 112,088 h × pg/mL ± 28,774 h × pg/mL |
| $AUC_{inf}$ | 115,773 h × pg/mL ± 29,099 h × pg/mL |
| $C_{max}$ | 16,859 pg/mL ± 4,153 pg/mL |
| $T_{max}$ (mean) | 1.351 h ± 0.535 h |
| $T_{max}$ (median) | 1.25 h |
| $T_{max}$ (range) | [0.5 h-3 h] |
| $t_{1/2}$ | 4.214 h ± 0.574 h |

Hydromorphone Summary:
single dose; Bz-HC.HCl/APAP tablet, 6.67 mg/325 mg; oral; fasted

TABLE 10

| Parameter | Hydromorphone Released from Bz-HC•HCl/APAP |
|---|---|
| $AUC_{0-24\,h}$ | 1,453 h × pg/mL ± 900 h × pg/mL |
| $AUC_{inf}$ | 1,702 h × pg/mL ± 1,215 h × pg/mL (only N = 14) |
| $C_{max}$ | 225 pg/mL ± 120 pg/mL |
| $T_{max}$ (mean) | 1.065 h ± 1.156 h |
| $T_{max}$ (median) | 0.5 h |
| $T_{max}$ (range) | [0.5 h-6 h] |
| $t_{1/2}$ | 8.282 h ± 6.327 h (only N = 14) |

Acetaminophen (APAP) Summary:
single dose; Bz-HC.HCl/APAP tablet, 6.67 mg/325 mg; oral; fasted

TABLE 11

| Parameter | APAP Released from Bz-HC•HCl/APAP |
|---|---|
| $AUC_{0-24\,h}$ | 16.388 h × µg/mL ± 3.987 h × µg/mL |
| $AUC_{inf}$ | 17.220 h × µg/mL ± 3.696 h × µg/mL |
| $C_{max}$ | 4.067 µg/mL ± 1.319 µg/mL |
| $T_{max}$ (mean) | 0.717 h ± 0.394 h |
| $T_{max}$ (median) | 0.5 h |
| $T_{max}$ (range) | [0.5 h-2 h] |
| $t_{1/2}$ | 4.934 h ± 0.977 h |

Example 16

Bz-HC.HCl/APAP Steady State Human Pharmacokinetic Studies

A study was conducted to assess the pharmacokinetics of Bz-HC, hydrocodone, hydromorphone, and acetaminophen (APAP) after single and multiple doses of Bz-HC.HCl/APAP tablets (2×6.67 mg/325 mg) under fasted conditions and the systemic exposure to Bz-HC after administration of multiple doses of Bz-HC.HCl/APAP tablets (2×6.67 mg/325 mg) with a total daily dose of 12 tablets based on the maximum daily APAP dose of 4 grams.

This was a single-period, single- and multiple-dose study in which 26 healthy adult subjects were to be enrolled with the goal of completing 20. After completing an overnight fast (10 hours), subjects received a single dose (Dose 1, Day 1) of 2 Bz-HC.HCl/APAP tablets to evaluate single-dose pharmacokinetics. Twenty-four (24) hours after the first dose (Day 2), subjects entered the multi-dose portion of the study and received 2 Bz-HC.HCl/APAP tablets (Dose 2 through Dose 14) every 4 hours for a total of 14 doses in a confined setting.

Blood samples (2×6 mL) for pharmacokinetic analysis were collected prior to and up to 24 hours after dose 1 (Day 1) and Dose 14 (Day 4). In addition, to confirm that steady-state was achieved, blood samples were collected prior to Doses 4 and 6 on Day 2, and prior to Doses 8, 10, and 12 on Day 3. A total of 26 subjects were enrolled and 24 subjects completed the study. The 24 subjects that completed the study comprised the pharmacokinetic (PK) analysis population.

Figure 27:
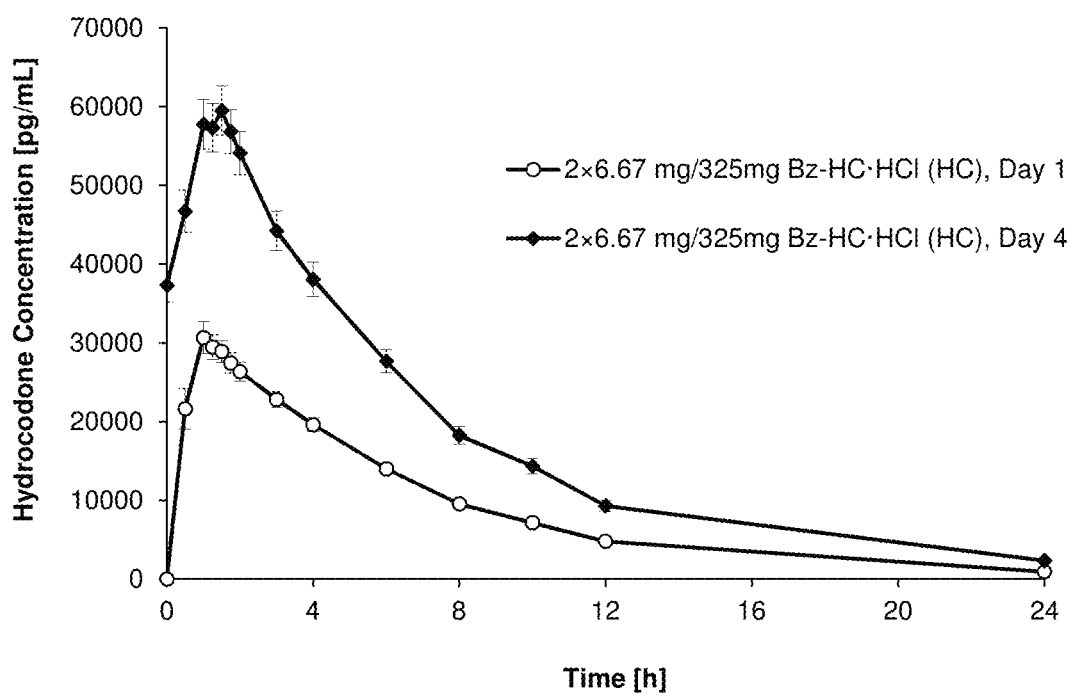
FIG. 27. PK profile graph of plasma concentrations of hydrocodone released from Bz-HC.HCl/APAP (2×6.67 mg/325 mg) over time upon multiple dose, oral administration in fasted humans.
Figure 28:
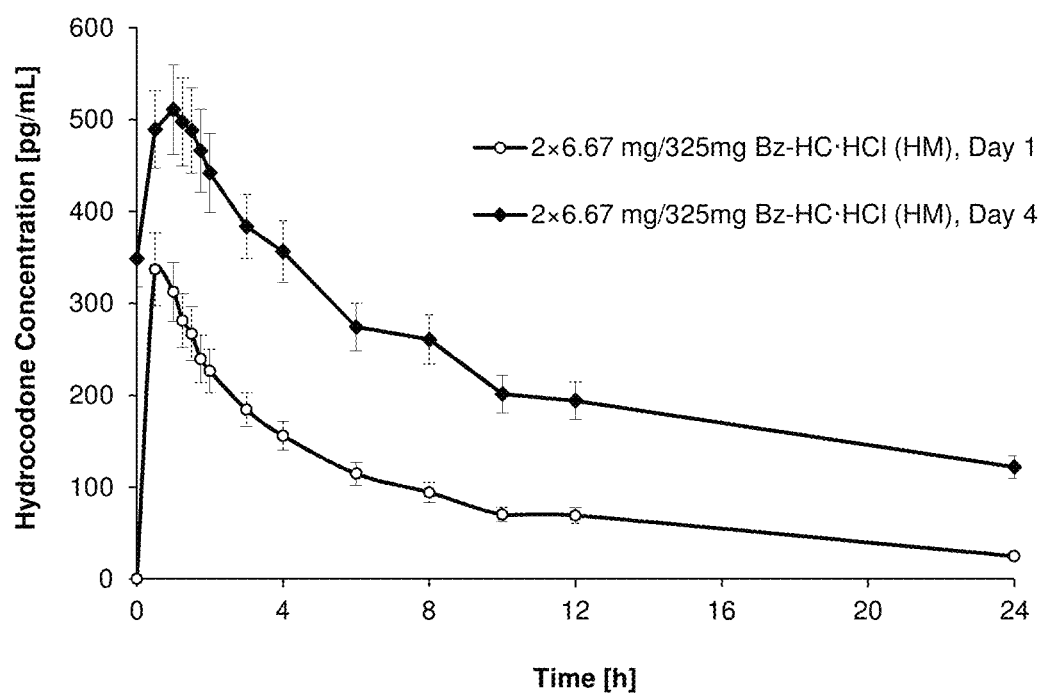
FIG. 28. PK profile graph of plasma concentrations of hydromorphone released from Bz-HC.HCl/APAP (2×6.67 mg/325 mg) over time upon multiple dose, oral administration in fasted humans.
Figure 29:
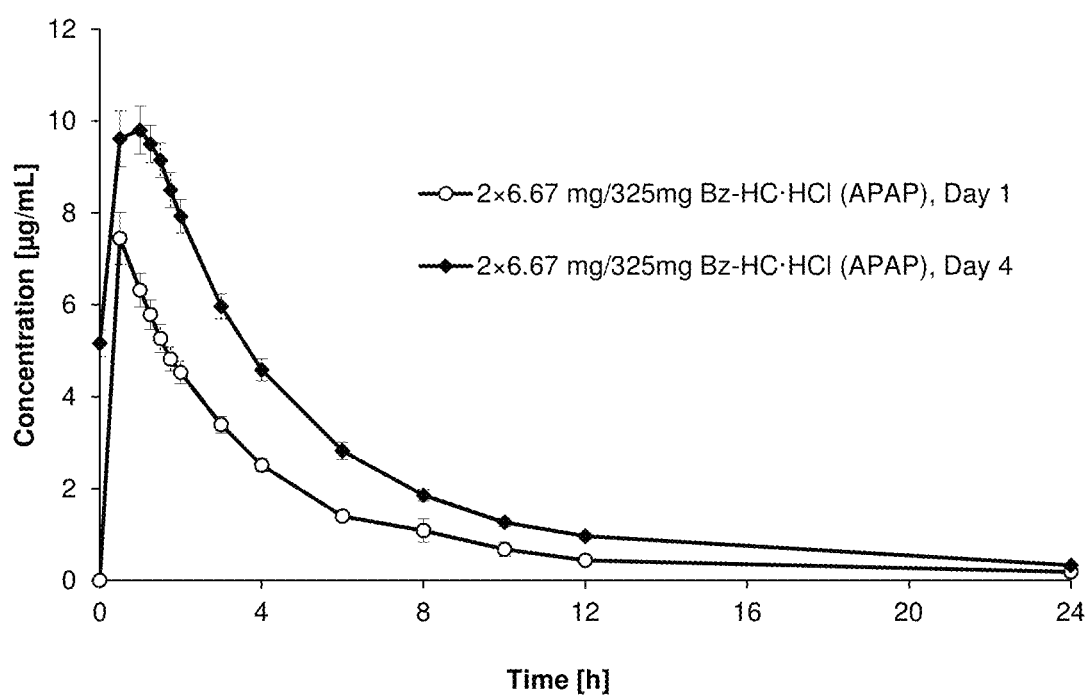
FIG. 29. PK profile graph of plasma concentrations of acetaminophen released from Bz-HC.HCl/APAP (2×6.67 mg/325 mg) over time upon multiple dose, oral administration in fasted humans.
Figure 30:
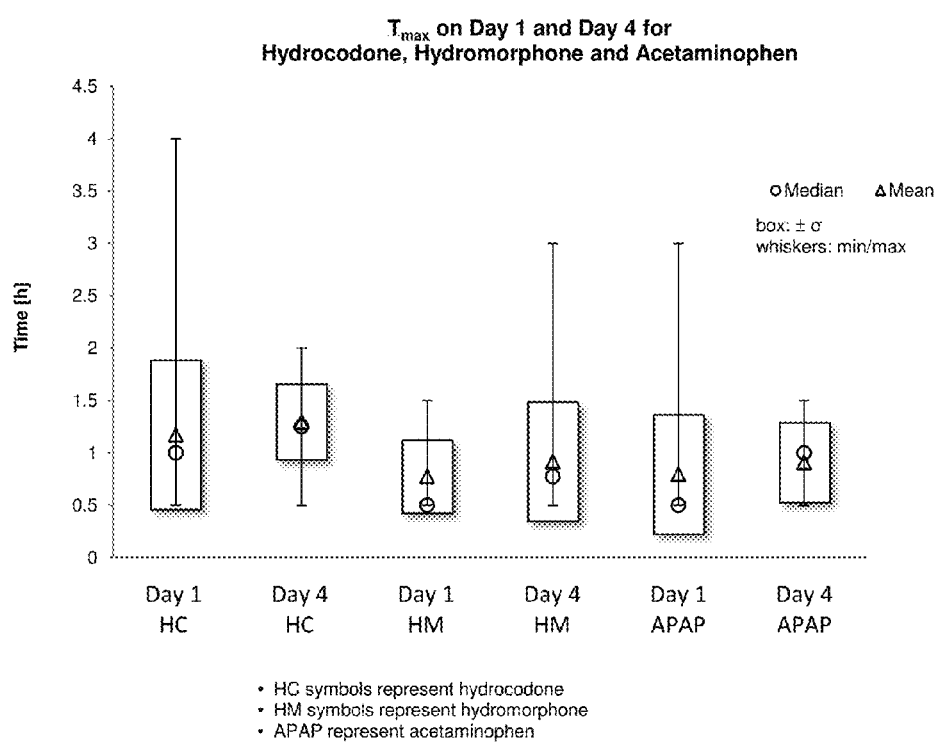
FIG. 30. Comparison of $T_{max}$ for hydrocodone, hydromorphone and acetaminophen upon multiple dose, oral administration in fasted humans between day 1 and day 4.
Figure 31:
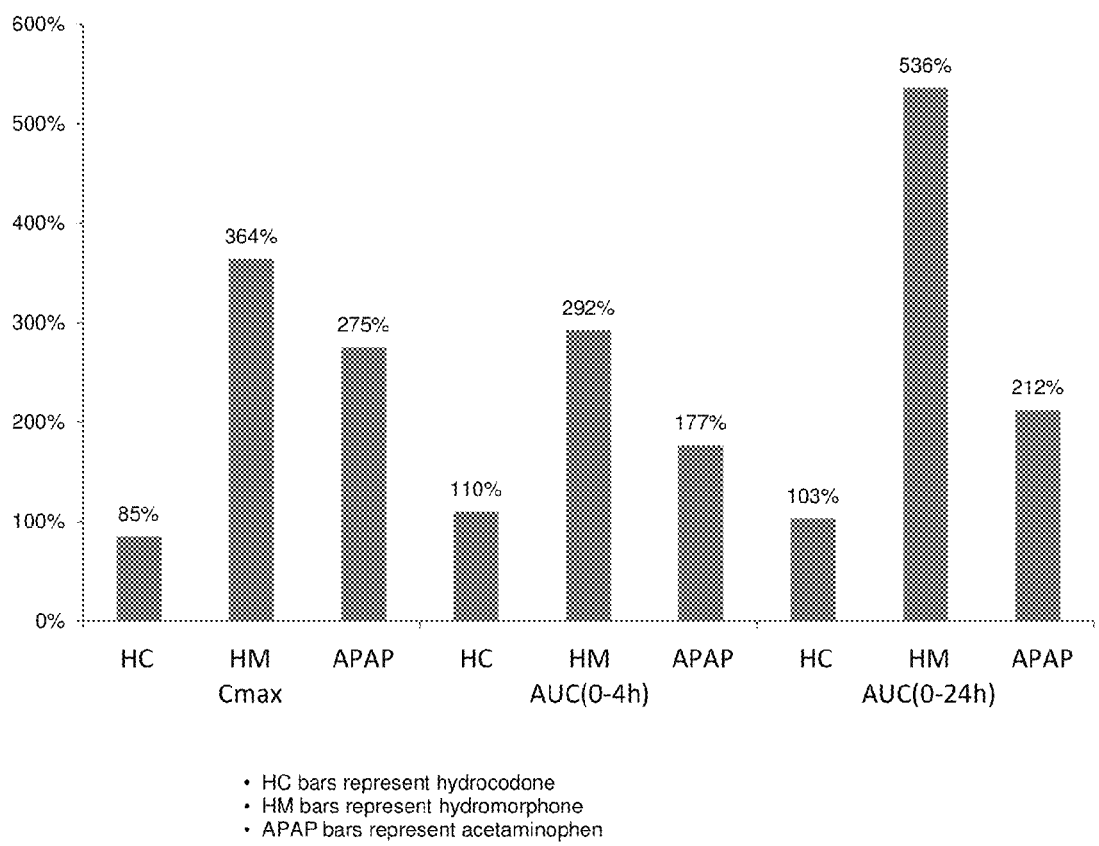
FIG. 31. Day 1 to Day 4 accumulation ratios for hydrocodone, hydromorphone and acetaminophen upon multiple dose, oral administration in fasted humans.

A summary of the PK data for hydrocodone single dose, multiple dose and steady state is presented in Tables 12, 13, and 14, respectively. A summary of the PK data for hydromorphone single dose and multiple dose is presented in Tables 15 and 16, respectively. A summary of the PK data for acetaminophen single dose, multiple dose and steady state is presented in Tables 17, 18, and 19. PK curves of the of the mean±standard error plasma concentrations of hydrocodone, hydromorphone and acetaminophen are present in FIGS. 27, 28, and 29, respectively. A comparison of $T_{max}$ for hydrocodone, hydromorphone and acetaminophen between Day 1 and Day 4 is presented in FIG. 30. Accumulation ratios for hydrocodone, hydromorphone and acetaminophen from Day 1 to Day 4 ($C_{max}$, $AUC_{0-4\,h}$ and $AUC_{inf}$) are shown in FIG. 31. These results demonstrate that the PK of hydrocodone and acetaminophen are linear and predictable after administration of single and multiple doses of Bz-HC.HCl.

Hydrocodone Single Doses:
single oral dose of Bz-HC.HCl/APAP tablets, 13.34 mg/650 mg

TABLE 12

| Parameter | Hydrocodone Released from Bz-HC•HCl/APAP |
| --- | --- |
| $AUC_{0-4\,h}$ | 92,940 h × pg/mL ± 20,158 h × pg/mL |
| $AUC_{0-24\,h}$ | 212,948 h × pg/mL ± 52,803 h × pg/mL |
| $AUC_{inf}$ | 219,357 h × pg/mL ± 57,283 h × pg/mL |
| $C_{max}$ | 33,946 pg/mL ± 8,407 pg/mL |
| $T_{max}$ (mean) | 1.173 h ± 0.709 h |
| $T_{max}$ (median) | 1 h |
| $T_{max}$ (range) | [0.5 h-4 h] |
| $t_{1/2}$ | 4.448 h ± 0.590 h |

Hydrocodone Multiple Doses:
post-dose at steady-state, oral dose of Bz-HC.HCl/APAP tablets, 13.34 mg/650 mg

TABLE 13

| Parameter | Hydrocodone Released from Bz-HC•HCl/APAP |
| --- | --- |
| $AUC_{0-4\,h}$ | 195,074 h × pg/mL ± 47,655 h × pg/mL |
| $AUC_{0-24\,h}$ | 432,752 h × pg/mL ± 118,669 h × pg/mL |
| $C_{max}$ | 62,788 pg/mL ± 14,751 pg/mL |
| $T_{max}$ (mean) | 1.295 h ± 0.361 h |
| $T_{max}$ (median) | 1.25 h |
| $T_{max}$ (range) | [0.5 h-2 h] |
| $t_{1/2}$ | 4.874 h ± 0.629 h |

Hydrocodone Steady-State:

TABLE 14

| steady-state reached >24 h with Q4H dosing (after Dose 6) |
| --- |
| $C_{max}$ ratio (single dose vs. steady-state): 1.85 |
| $AUC_{0-4\,h}$ ratio (single dose vs. steady-state): 2.10 |
| $AUC_{0-24\,h}$ ratio (single dose vs. steady-state): 2.03 |

Hydromorphone Single Doses:
single oral dose of Bz-HC.HCl/APAP tablets, 13.34 mg/650 mg

TABLE 15

| Parameter | Hydromorphone Released from Bz-HC•HCl/APAP |
| --- | --- |
| $AUC_{0-4\,h}$ | 888 h × pg/mL ± 431 h × pg/mL |
| $AUC_{0-24\,h}$ | 2,148 h × pg/mL ± 1,197 h × pg/mL |
| $AUC_{inf}$ | 2,418 h × pg/mL ± 1,249 h × pg/mL (only N = 11) |
| $C_{max}$ | 372 pg/mL ± 184 pg/mL |
| $T_{max}$ (mean) | 0.776 h ± 0.350 h |
| $T_{max}$ (median) | 0.5 h |
| $T_{max}$ (range) | [0.5 h-1.5 h] |
| $t_{1/2}$ | 8.896 h ± 3.892 h (only N = 11) |

Hydromorphone Multiple Doses:
post-dose at steady-state, oral dose of Bz-HC.HCl/APAP tablets, 13.34 mg/650 mg

TABLE 16

| Parameter | Hydromorphone Released from Bz-HC•HCl/APAP |
| --- | --- |
| $AUC_{0-4\,h}$ | 1,727 h × pg/mL ± 770 h × pg/mL |
| $AUC_{0-24\,h}$ | 5,645 h × pg/mL ± 2,525 h × pg/mL |
| $C_{max}$ | 548 pg/mL ± 232 pg/mL |
| $T_{max}$ (mean) | 0.919 h ± 0.568 h |
| $T_{max}$ (median) | 0.773 h |
| $T_{max}$ (range) | [0.5 h-3 h] |
| $t_{1/2}$ | 13.306 h ± 3.602 h (only N = 9) |

Acetaminophen SINGLE Doses:
single oral dose of Bz-HC.HCl/APAP tablets, 13.34 mg/650 mg

TABLE 17

| Parameter | APAP Released from Bz-HC•HCl/APAP |
| --- | --- |
| $AUC_{0-4\,h}$ | 17.622 h × µg/mL ± 4.247 h × µg/mL |
| $AUC_{0-24\,h}$ | 30.526 h × µg/mL ± 12.736 h × µg/mL |
| $AUC_{inf}$ | 28.945 h × µg/mL ± 7.069 h × µg/mL |
| $C_{max}$ | 7.951 µg/mL ± 2.157 µg/mL |
| $T_{max}$ (mean) | 0.797 h ± 0.567 h |
| $T_{max}$ (median) | 0.5 h |
| $T_{max}$ (range) | [0.5 h-3 h] |
| $t_{1/2}$ | 4.787 h ± 1.210 h |

Acetaminophen Multiple Doses:
post-dose at steady-state, oral dose of Bz-HC.HCl/APAP tablets, 13.34 mg/650 mg

TABLE 18

| Parameter | APAP Released from Bz-HC•HCl/APAP |
| --- | --- |
| $AUC_{0-4\,h}$ | 29.820 h × µg/mL ± 6.186 h × µg/mL |
| $AUC_{0-24\,h}$ | 54.997 h × µg/mL ± 13.570 h × µg/mL |
| $C_{max}$ | 11.033 µg/mL ± 2.344 µg/mL |
| $T_{max}$ (mean) | 0.908 h ± 0.380 h |
| $T_{max}$ (median) | 1 h |
| $T_{max}$ (range) | [0.5 h-1.5 h] |
| $t_{1/2}$ | 6.840 h ± 2.415 h |

Acetaminophen Steady-State:

TABLE 19

| steady-state reached between 24 h and 36 h with Q4H dosing |
| --- |
| $C_{max}$ ratio (single dose vs. steady-state): 1.38 |
| $AUC_{0-4\,h}$ ratio (single dose vs. steady-state): 1.69 |
| $AUC_{0-24\,h}$ ratio (single dose vs. steady-state): 1.80 |

Example 17

Bz-HC.HCl/APAP Human Pharmacokinetic Effect of Food Studies

A study was conducted to assess the effect of food on the bioavailability and pharmacokinetics of hydrocodone and acetaminophen (APAP) from Bz-HC.HCl/APAP Tablets, 6.67 mg/325 mg and to assess the relative bioavailability of Bz-HC.HCl/APAP Tablet, 6.67 mg/325 mg and Norco® tablet, 7.5 mg/325 mg (NDC #52544-162-01) under fed conditions in healthy volunteers.

This was a single-dose, randomized, 3-treatment, 3-period, 6-sequence, crossover study in which 42 healthy adult subjects were to be enrolled with the goal of completing 30. Subjects received single-dose treatments according to a randomization schedule. The fed treatments included a single dose of Bz-HC.HCl/APAP, 6.67 mg/325 mg and a single dose of Norco®, 7.5 mg/325 mg, administered under fed conditions while the fasted treatment included Bz-HC.HCl/APAP, 6.67 mg/325 mg, administered under fasted conditions.

Each treatment period was separated by at least a 7-day washout period. Fasted doses were administered after a standard overnight fast (approximately 10 hours) and fed doses were administered 30 minutes after beginning to ingest a standard meal. Each dose was administered along with approximately 240 mL (8 fl. oz.) of room temperature tap water. No food was allowed until 4 hours after dose administration. Except for the 240 mL of room temperature tap water provided with the dose, no water was consumed for 1 hour prior through 1 hour after dosing.

Blood samples (1×6 mL+1×4 mL) for pharmacokinetic analysis were collected prior to and up to 24 hours after each dose.

A total of 42 subjects were enrolled. The pharmacokinetic (PK) analysis population was comprised of 40 subjects for the fed treatments (39 for APAP) and 38 subjects for the fasted treatment.

Figure 32:
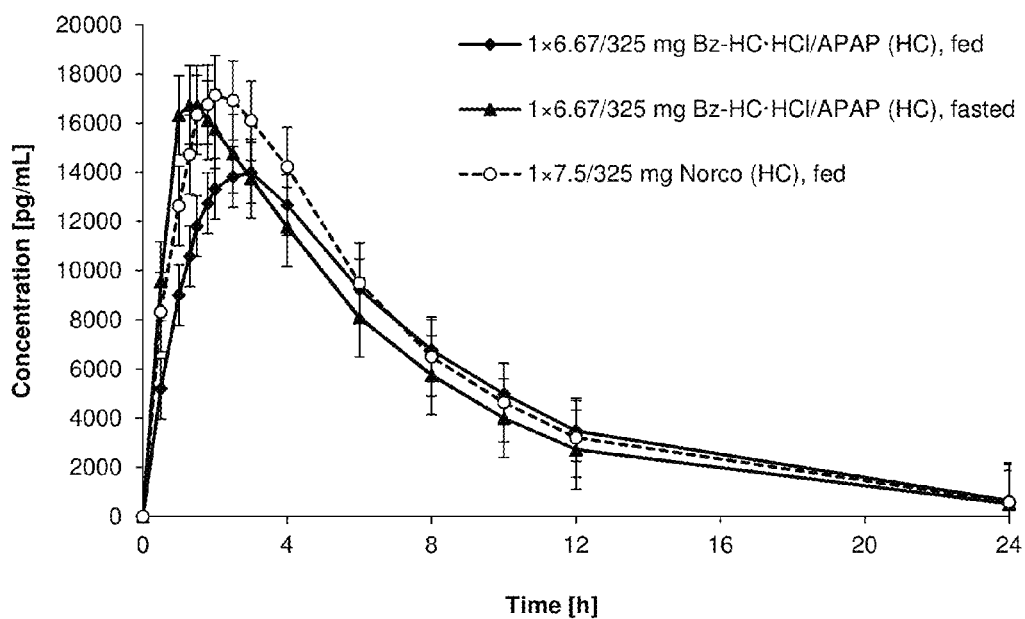
FIG. 32. PK profile graph of plasma concentrations of hydrocodone released from Bz-HC.HCl/APAP (6.67 mg/325 mg) and Norco® upon single dose, oral administration in fed and fasted humans.
Figure 33:
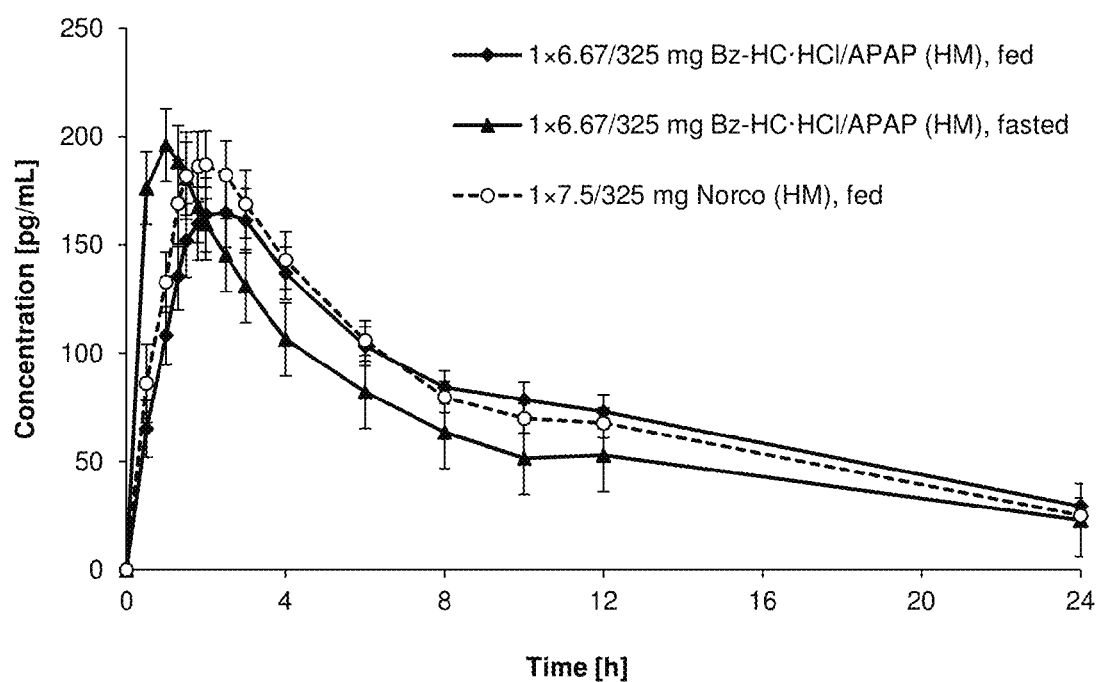
FIG. 33. PK profile graph of plasma concentrations of hydromorphone released from Bz-HC.HCl/APAP (6.67 mg/325 mg) and Norco® upon single dose, oral administration in fed and fasted humans.
Figure 34:
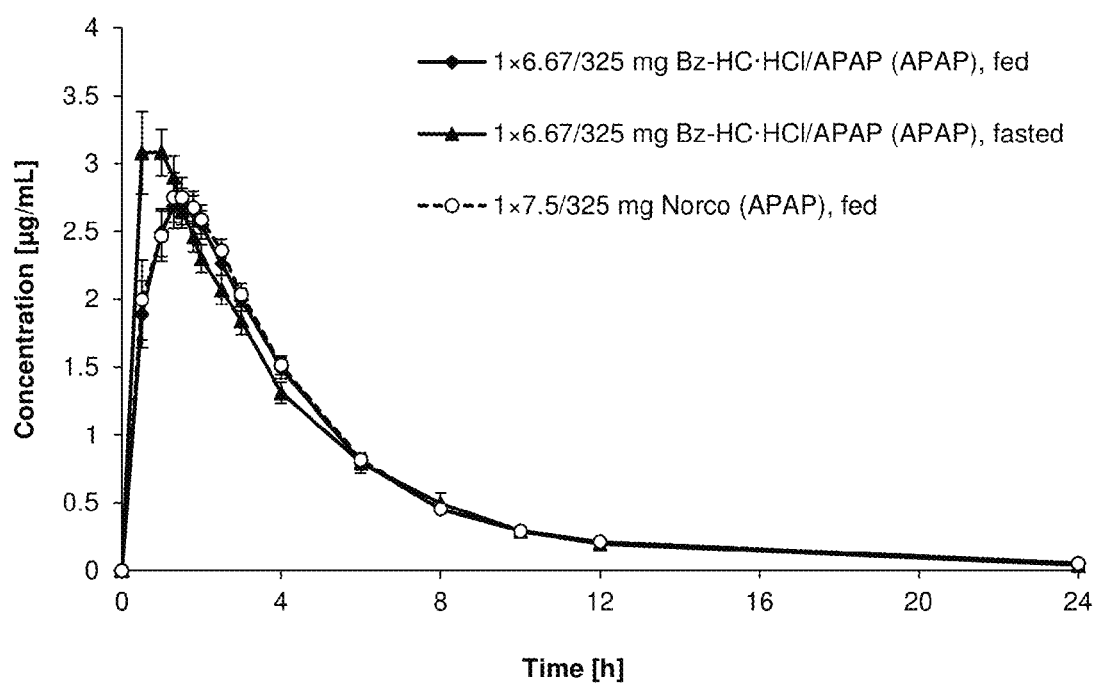
FIG. 34. PK profile graph of plasma concentrations of acetaminophen released from Bz-HC.HCl/APAP (6.67 mg/325 mg) and Norco® upon single dose, oral administration in fed and fasted humans.
Figure 35:
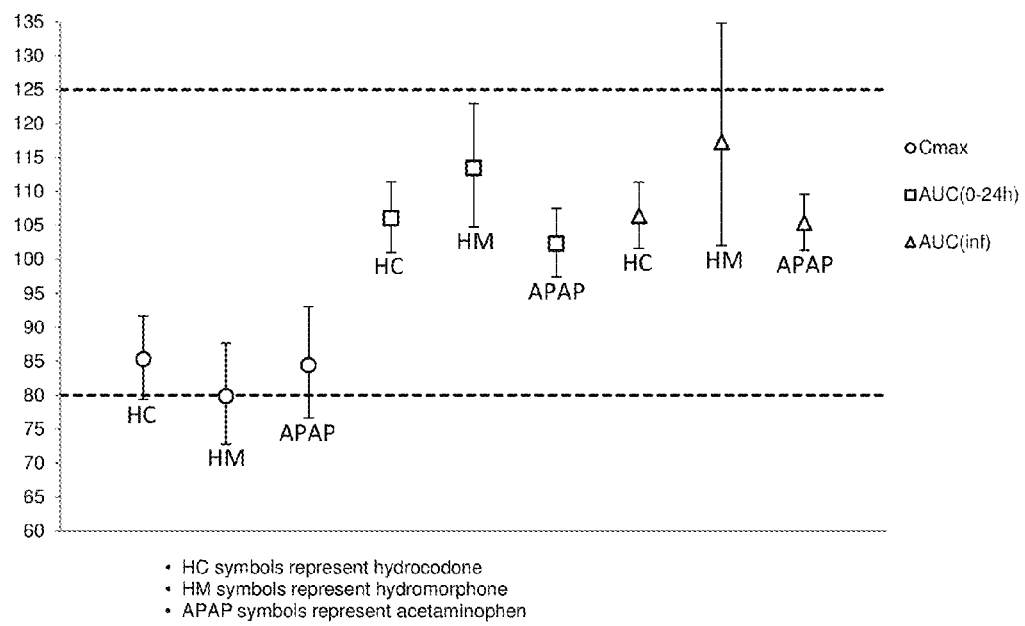
FIG. 35. Estimated geometric means and 90% confidence intervals for hydrocodone, hydromorphone and acetaminophen under fed and fasted conditions.

A summary of the PK data for hydrocodone fasted, fed and fed vs. fasted is presented in Tables 20, 21, and 22, respectively. A summary of the PK data for hydromorphone fasted, fed and fed vs. fasted is presented in Tables 23, 24, and 25, respectively. A summary of the PK data for acetaminophen fasted, fed and fed vs. fasted is presented in Tables 26, 27, and 28, respectively. PK curves of the of the mean±standard error plasma concentrations of hydrocodone, hydromorphone and acetaminophen under fed and fasted conditions are presented in FIGS. 32, 33, and 34, respectively. Estimated geometric mean rations and 90% confidence intervals (Cl) for the least squares mean ratios (GMR) of the log-transformed PK parameters comparing Bz-HC.HCl/APAP under fed and fasted conditions are presented in FIG. 35. These results demonstrate that Bz-HC.HCl/APAP (6.67 mg/325 mg) shows no clinically relevant food effect.

Hydrocodone Food Effect:
single oral dose of 6.67 mg/325 mg of Bz-HC.HCl/APAP, fasted

TABLE 20

| Parameter | Hydrocodone Released from Bz-HC•HCl/APAP |
|---|---|
| $AUC_{0-24\,h}$ | 121,404 h × pg/mL ± 35,183 h × pg/mL |
| $AUC_{inf}$ | 125,729 h × pg/mL ± 36,783 h × pg/mL |
| $C_{max}$ | 19,175 pg/mL ± 4,840 pg/mL |
| $T_{max}$ (mean) | 1.408 h ± 0.602 h |
| $T_{max}$ (median) | 1.25 h |
| $T_{max}$ (range) | [0.5 h-3 h] |
| $t_{1/2}$ | 4.325 h ± 0.669 h |

Hydrocodone Food Effect:
single oral dose of 6.67 mg/325 mg of Bz-HC.HCl/APAP, fed

TABLE 21

| Parameter | Hydrocodone Released from Bz-HC•HCl/APAP |
|---|---|
| $AUC_{0-24\,h}$ | 125,798 h × pg/mL ± 26,900 h × pg/mL |
| $AUC_{inf}$ | 130,905 h × pg/mL ± 29,451 h × pg/mL |

TABLE 21-continued

| Parameter | Hydrocodone Released from Bz-HC•HCl/APAP |
|---|---|
| $C_{max}$ | 16,044 pg/mL ± 3,608 pg/mL |
| $T_{max}$ (mean) | 2.502 h ± 0.955 h |
| $T_{max}$ (median) | 2.5 h |
| $T_{max}$ (range) | [0.5 h-4 h] |
| $t_{1/2}$ | 4.530 h ± 0.700 h |

Hydrocodone Fed Vs. Fasted:

TABLE 22

$C_{max}$ decreased with food by 16.3% (mean to mean), from −48% to 37%
$AUC_{0-24\,h}$ increased with food by 3.6% (mean to mean), from −37% to 77%
$AUC_{inf}$ increased with food by 4.1% (men to mean), from −38% to 80%
$T_{max}$ (mean) change from
$T_{max}$ (median) increased with food from 1.25 h
$T_{max}$ (range) increased with food from [0.5 h-3 h] (fasted) to [0.5 h-4 h] (fed)
Statistically no overall change in exposure.

Hydromorphone Food Effect:
single oral dose of 6.67 mg/325 mg of Bz-HC.HCl/APAP, fasted

TABLE 23

| Parameter | Hydromorphone Released from Bz-HC•HCl/APAP |
|---|---|
| $AUC_{0-24\,h}$ | 1,521 h × pg/mL ± 915 h × pg/mL |
| $AUC_{inf}$ | 2,229 h × pg/mL ± 1,272 h × pg/mL (only N = 17) |
| $C_{max}$ | 235 pg/mL ± 130 pg/mL |
| $T_{max}$ (mean) | 0.994 h ± 0.597 h |
| $T_{max}$ (median) | 1 h |
| $T_{max}$ (range) | [0.5 h-3 h] |
| $t_{1/2}$ | 11.185 h ± 4.411 h (only N = 17) |

Hydromorphone Food Effect:
single oral dose of 6.67 mg/325 mg of Bz-HC.HCl/APAP, fed

TABLE 24

| Parameter | Hydromorphone Released from Bz-HC•HCl/APAP |
|---|---|
| $AUC_{0-24\,h}$ | 1,806 h × pg/mL ± 1,141 h × pg/mL |
| $AUC_{inf}$ | 2,562 h × pg/mL ± 1,463 h × pg/mL (only N = 30) |
| $C_{max}$ | 194 pg/mL ± 113 pg/mL |
| $T_{max}$ (mean) | 2.358 h ± 1.158 h |
| $T_{max}$ (median) | 2 h |
| $T_{max}$ (range) | [0.5 h-6 h] |
| $t_{1/2}$ | 12.182 h ± 5.447 h (only N = 30) |

Hydromorphone Fed vs. Fasted:

TABLE 25

$C_{max}$ decreased with food by 17.5% (mean to mean), from −78% to 193%
$AUC_{0-24\,h}$ increased with food by 18.7% (mean to mean), from −73% to 386%
$T_{max}$ (mean) change from −25% to 786%
$T_{max}$ (median) increased with food from 1 h (fasted) to 2 h (fed)
$T_{max}$ (range) increased with food from [0.5 h-3 h] (fasted) to [0.5 h-6 h] (fed)
Statistically no overall change in exposure.

Acetaminophen Food Effect:
single oral dose of 6.67 mg/325 mg of Bz-HC.HCl/APAP, fasted

TABLE 26

| Parameter | APAP Released from Bz-HC•HCl/APAP |
|---|---|
| $AUC_{0-24\,h}$ | 14.640 h × µg/mL ± 4.424 h × µg/mL |
| $AUC_{inf}$ | 14.683 h × µg/mL ± 3.867 h × µg/mL |
| $C_{max}$ | 4.048 µg/mL ± 1.300 µg/mL |
| $T_{max}$ (mean) | 1.054 h ± 0.708 h |
| $T_{max}$ (median) | 1 h |
| $T_{max}$ (range) | [0.5 h-3 h] |
| $t_{1/2}$ | 4.781 h ± 1.303 h |

Acetaminophen Food Effect:
  single oral dose of 6.67 mg/325 mg of Bz-HC.HCl/APAP, fed

TABLE 27

| Parameter | APAP Released from Bz-HC•HCl/APAP |
|---|---|
| $AUC_{0-24\,h}$ | 14.497 h × µg/mL ± 3.414 h × µg/mL |
| $AUC_{inf}$ | 15.031 h × µg/mL ± 3.533 h × µg/mL |
| $C_{max}$ | 3.344 µg/mL ± 1.011 µg/mL |
| $T_{max}$ (mean) | 1.547 h ± 0.871 h |
| $T_{max}$ (median) | 1.5 h |
| $T_{max}$ (range) | [0.5 h-4 h] |
| $t_{1/2}$ | 5.636 h ± 1.577 h |

Acetaminophen Fed vs. Fasted:

TABLE 28

$C_{max}$ decreased with food by 17.4% (mean to mean), from −56% to 58%
$AUC_{0-24\,h}$ decreased with food by 1.0% (mean to mean), from −42% to 75%
$AUC_{inf}$ increased with food by 2.4% (mean to mean), from −38% to 72%
$T_{max}$ (mean) change from −62% to 598%
$T_{max}$ (median) increased with food from 1 h (fasted) to 1.5 h (fed)
$T_{max}$ (range) increased with food from [0.5 h-3 h] (fasted) to [0.5 h-4 h] (fed)
Statistically no overall change in exposure.

Example 18

Bz-HC.HCl/APAP Single Dose Human Pharmacokinetic Studies

An additional study was conducted to further investigate the rate and extent of absorption of hydrocodone and hydromorphone from Bz-HC.HCl/APAP tablets (1×6.67 mg/325 mg) when administered to healthy subjects under fasted conditions.

This was a single-dose, randomized, 2-treatment, 2-period, 2-sequence, crossover study in which 30 healthy adult subjects were to be enrolled with the goal of completing 26. Subjects received 2 single-dose treatments according to a randomization schedule. The treatment included were Bz-HC.HCl/APAP, 6.67 mg/325 mg and Vicoprofen® (hydrocodone bitartrate/ibuprofen), 7.5 mg/200 mg (NDC #0074-2277-14), administered under fasted conditions.

Each treatment period was separated by at least a 7-day washout period. Each dose was administered after a standard overnight fast (approximately 10 hours) with approximately 240 mL (8 fl. oz.) of room temperature tap water. No food was allowed until 4 hours after dose administration. Except for the 240 mL of room temperature tap water provided with the dose, no water was consumed for 1 hour prior through 1 hour after dosing.

Blood samples (1×6 mL) for pharmacokinetic analysis were collected prior to and up to 24 hours after each dose.

A total of 30 subjects were enrolled. Twenty-eight (28) subjects completed both study periods. The pharmacokinetic (PK) analysis population was comprised of 28 subjects.

Figure 36:
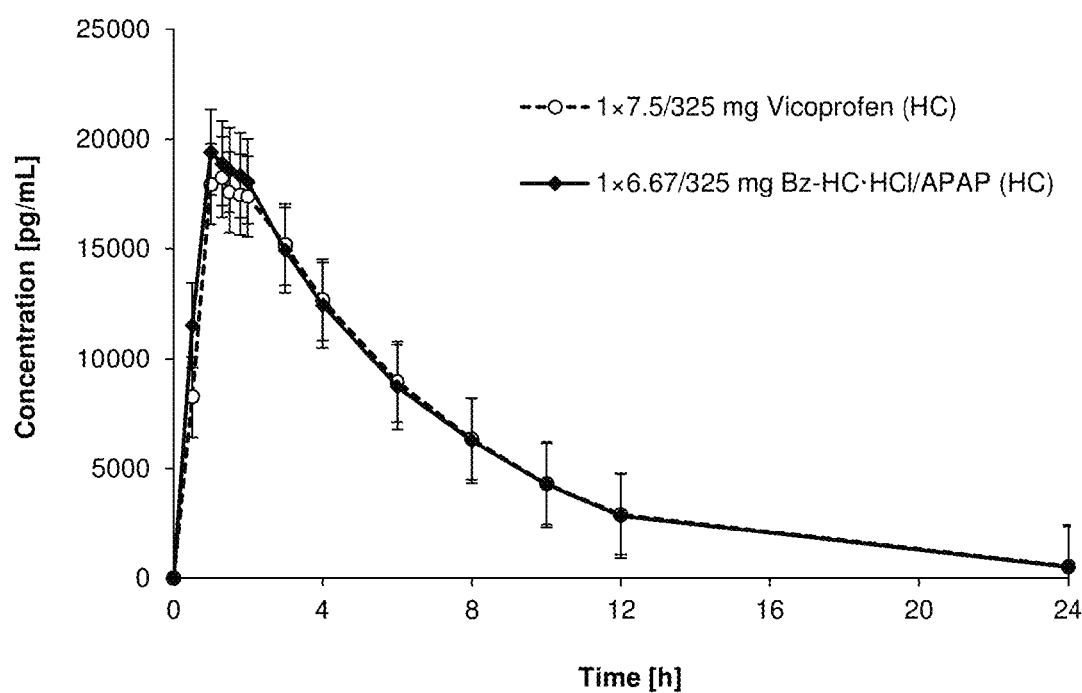
FIG. 36. PK profile graph of plasma concentrations of hydrocodone released from Bz-HC.HCl/APAP (6.67 mg/325 mg) and Vicoprofen® upon single dose, oral administration in fasted humans.
Figure 37:
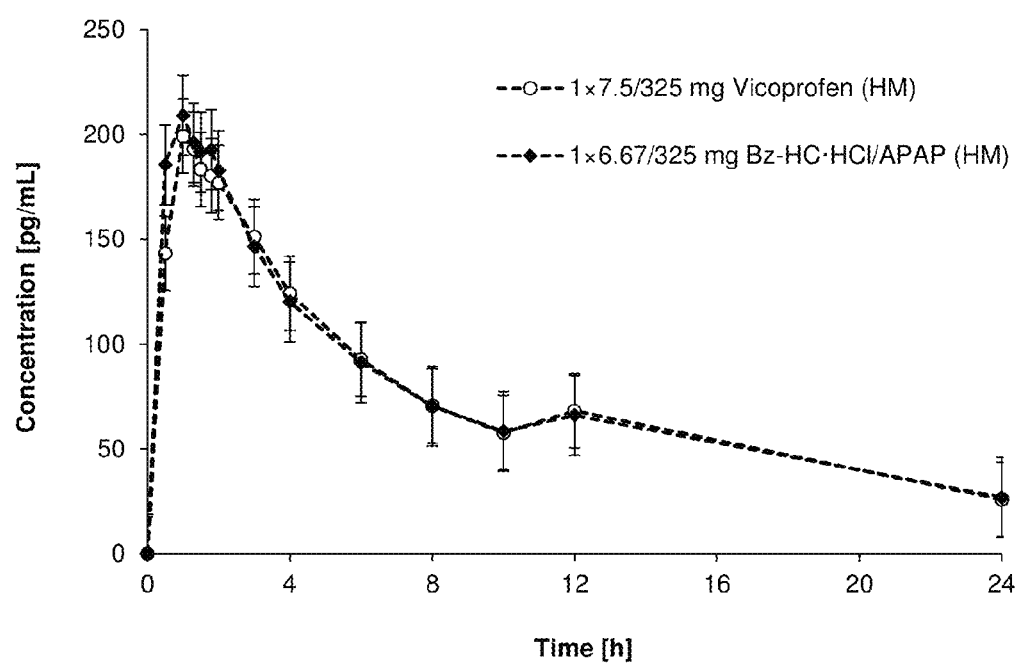
FIG. 37. PK profile graph of plasma concentrations of hydromorphone released from Bz-HC.HCl/APAP (6.67 mg/325 mg) and Vicoprofen® upon single dose, oral administration in fasted humans.

A summary of the PK data for hydrocodone and hydromorphone is presented in Tables 29 and 30, respectively. PK curves of the of the mean±standard error plasma concentrations of hydrocodone and hydromorphone are presented in FIGS. 36 and 37, respectively. These results demonstrate that Bz-HC.HCl/APAP (6.67 mg/325 mg) is bioequivalent to Vicoprofen® (7.5 mg/200 mg) and similar immediate release hydrocodone combination products.

Hydrocodone Summary:
  single oral dose of 6.67 mg/325 mg of Bz-HC.HCl/APAP

TABLE 29

| Parameter | Hydrocodone Released from Bz-HC•HCl/APAP |
|---|---|
| $AUC_{0-24\,h}$ | 132,618 h × pg/mL ± 34,198 h × pg/mL |
| $AUC_{inf}$ | 136,499 h × pg/mL ± 34,899 h × pg/mL |
| $C_{max}$ | 21,061 pg/mL ± 4,426 pg/mL |
| $T_{max}$ (mean) | 1.241 h ± 0.394 h |
| $T_{max}$ (median) | 1.00 h |
| $T_{max}$ (range) | [0.5 h-2 h] |
| $t_{1/2}$ | 4.190 h ± 0.638 h |

Hydromorphone Summary:
  single oral dose of 6.67 mg/325 mg of Bz-HC.HCl/APAP

TABLE 30

| Parameter | Hydromorphone Released from Bz-HC•HCl/APAP |
|---|---|
| $AUC_{0-24\,h}$ | 1,741 h × pg/mL ± 896 h × pg/mL |
| $AUC_{inf}$ | 2,269 h × pg/mL ± 1,541 h × pg/mL (only N = 4) |
| $C_{max}$ | 246 pg/mL ± 98 pg/mL |
| $T_{max}$ (mean) | 0.964 h ± 0.434 h |
| $T_{max}$ (median) | 1.00 h |
| $T_{max}$ (range) | [0.5 h-2 h] |
| $t_{1/2}$ | 8.791 h ± 4.827 h |

Example 19

Bz-HC.HCl/APAP Single Dose Human Pharmacokinetic Studies

An additional study was conducted to further analyze the rate and extent of absorption of hydrocodone, and hydromorphone, and acetaminophen (APAP) from Bz-HC.HCl/APAP tablets (1×6.67 mg/325 mg) when administered to healthy subjects under fasted conditions.

This was a single-dose, randomized, 2-treatment, 2-period, 2-sequence, crossover study in which 26 healthy adult subjects were to be enrolled with the goal of completing 20. Subjects received 2 single-dose treatments according to a randomization schedule. The treatments included were Bz-HC.HCl/APAP, 6.67 mg/325 mg and Ultracet® (tramadol/ acetaminophen), 37.5 mg/325 mg (NDC #50458-650-60), administered under fasted conditions.

Each treatment period was separated by at least a 7-day washout period. Each dose was administered after a standard overnight fast (approximately 10 hours) with approximately 240 mL (8 fl. oz.) of room temperature tap water. No food was allowed until 4 hours after dose administration. Except for the 240 mL of room temperature tap water provided with the dose, no water was consumed for 1 hour prior through 1 hour after dosing.

Blood samples (1×6 mL) for pharmacokinetic analysis were collected prior to and up to 36 hours after each dose.

A total of 30 subjects were enrolled. Twenty-seven (27) subjects completed both study periods. The pharmacokinetic (PK) analysis population was comprised of 27 subjects.

Figure 38:
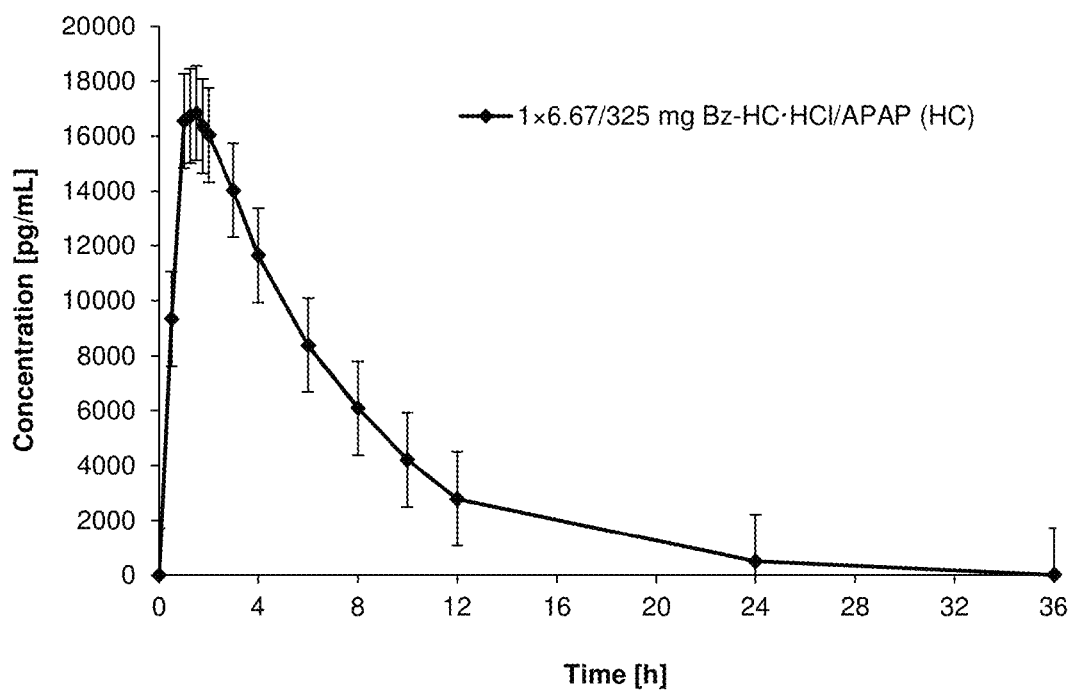
FIG. 38. PK profile graph of plasma concentrations of hydrocodone released from Bz-HC.HCl/APAP (6.67 mg/325 mg) upon single dose, oral administration in fasted humans.
Figure 39:
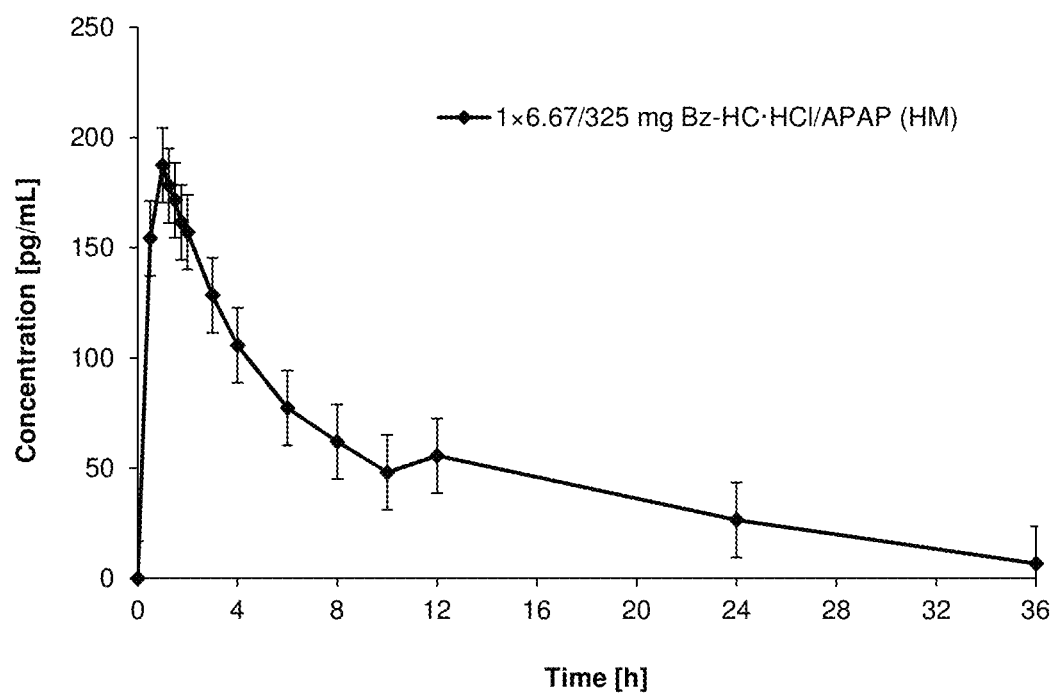
FIG. 39. PK profile graph of plasma concentrations of hydromorphone released from Bz-HC.HCl/APAP (6.67 mg/325 mg) upon single dose, oral administration in fasted humans.
Figure 40:
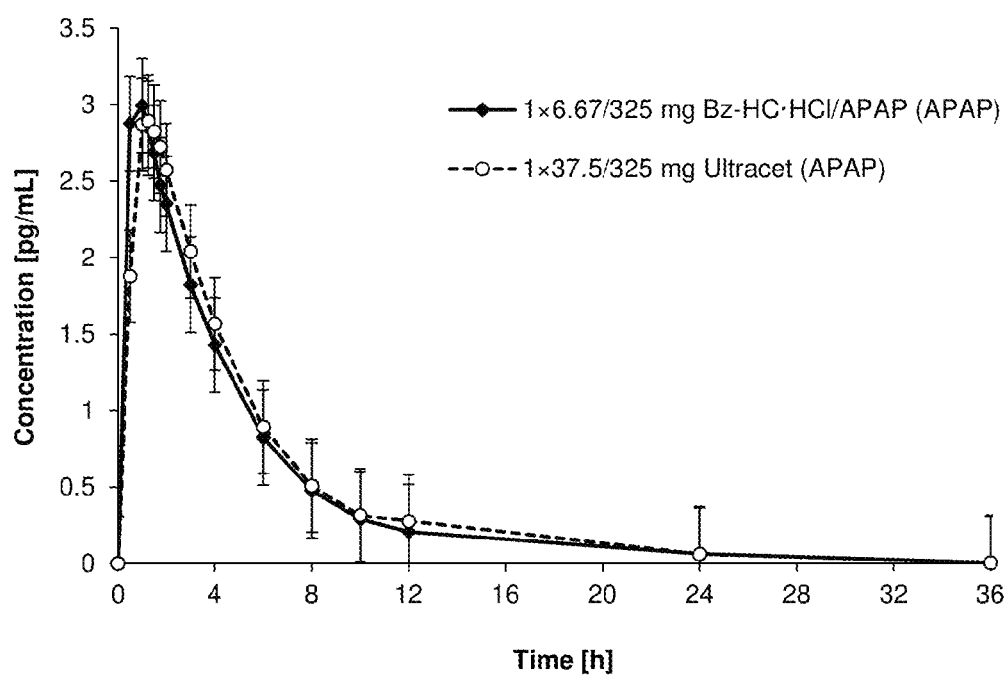
FIG. 40. PK profile graph of plasma concentrations of acetaminophen released from Bz-HC.HCl/APAP (6.67 mg/325 mg) and Ultracet® upon single dose, oral administration in fasted humans.

A summary of the PK data for hydrocodone, hydromorphone, and acetaminophen is presented in Tables 31, 32, and 33, respectively. PK curves of the of the mean±standard error plasma concentrations of hydrocodone, hydromorphone and acetaminophen are presented in FIGS. 38, 39, and 40, respectively. These results demonstrate that Bz-HC.HCl/APAP (6.67 mg/325 mg) is bioequivalent to Ultracet® (37.5 mg/325 mg) with respect to acetaminophen.

Hydrocodone Summary:
single oral dose of 6.67 mg/325 mg of Bz-HC.HCl/APAP

TABLE 31

| Parameter | Hydrocodone Released from Bz-HC•HCl/APAP |
|---|---|
| $AUC_{0-36\,h}$ | 124,102 h × pg/mL ± 30,541 h × pg/mL |
| $AUC_{inf}$ | 128,085 h × pg/mL ± 30,784 h × pg/mL |
| $C_{max}$ | 19,278 pg/mL ± 5,462 pg/mL |
| $T_{max}$ (mean) | 1.595 h ± 0.922 h |
| $T_{max}$ (median) | 1.25 h |
| $T_{max}$ (range) | [0.5 h-4 h] |
| $t_{1/2}$ | 4.347 h ± 0.681 h |

Hydromorphone Summary:
single oral dose of 6.67 mg/325 mg of Bz-HC.HCl/APAP

TABLE 32

| Parameter | Hydromorphone Released from Bz-HC•HCl/APAP |
|---|---|
| $AUC_{0-36\,h}$ | 1,644 h × pg/mL ± 1,012 h × pg/mL |
| $AUC_{inf}$ | not available |
| $C_{max}$ | 224 pg/mL ± 137 pg/mL |
| $T_{max}$ (mean) | 1.185 h ± 0.798 h |
| $T_{max}$ (median) | 1.00 h |
| $T_{max}$ (range) | [0.5 h-4 h] |
| $t_{1/2}$ | not available |

Acetaminophen Summary:
single oral dose of 6.67 mg/325 mg of Bz-HC.HCl/APAP

TABLE 33

| Parameter | APAP Released from Bz-HC•HCl/APAP |
|---|---|
| $AUC_{0-36\,h}$ | 15.138 h × μg/mL ± 4.480 h × μg/mL |
| $AUC_{inf}$ | 15.472 h × μg/mL ± 4.572 h × μg/mL |
| $C_{max}$ | 3.810 μg/mL ± 1.301 μg/mL |
| $T_{max}$ (mean) | 1.243 h ± 1.064 h |

TABLE 33-continued

| Parameter | APAP Released from Bz-HC•HCl/APAP |
|---|---|
| $T_{max}$ (median) | 1.00 h |
| $T_{max}$ (range) | [0.5 h-4 h] |
| $t_{1/2}$ | 5.269 h ± 1.856 h |

Example 20

Bz-HC.HCl/APAP Single Dose Human Pharmacokinetic Studies

The dose-dependent ranges of the PK parameters obtained in single dose studies conducted with oral formulations containing Bz-HC.HCl at doses from 5 mg to 13.34 mg in fasted, healthy subjects are summarized for hydrocodone, hydromorphone and APAP, as applicable, in Tables 34, 35, and 36, respectively. The ranges of the PK parameters obtained in single oral dose studies conducted with Bz-HC.HCl/APAP tablets, 6.67 mg/325 mg in fasted, healthy subjects are summarized hydrocodone, hydromorphone and APAP, as applicable, in Tables 37, 38 and 39, respectively.

Hydrocodone Summary:
single oral dose from 5 mg to 13.34 mg of Bz-HC.HCl, fasted

TABLE 34

| Parameter | Hydrocodone Released from Bz-HC•HCl or Bz-HC•HCl/APAP |
|---|---|
| $AUC_{0-24\,h}$ | 70.69 h × ng/mL ± 17.39 h × ng/mL to 212.95 h × ng/mL ± 52.80 h × ng/mL |
| $AUC_{inf}$ | 79.37 h × ng/mL ± 18.67 h × ng/mL to 219.36 h × ng/mL ± 57.28 h × ng/mL |
| $C_{max}$ | 12.8 ng/mL ± 3.84 ng/mL to 33.95 ng/mL ± 8.41 ng/mL |
| $T_{max}$ (mean) | 1.173 h ± 0.709 h to 1.866 h ± 0.901 h |
| $T_{max}$ (median) | 1 h to 1.5 h |
| $T_{max}$ (range) | [0.5 h-4 h] |
| $t_{1/2}$ | 3.79 h ± 0.88 h to 4.448 h ± 0.590 h |

Hydromorphone Summary:
single oral dose from 6.67 mg to 13.34 mg of Bz-HC.HCl, fasted

TABLE 35

| Parameter | Hydromorphone Released from Bz-HC•HCl or Bz-HC•HCl/APAP |
|---|---|
| $AUC_{0-24\,h}$ | 1,453 h × pg/mL ± 900 h × pg/mL to 2,148 h × pg/mL ± 1,197 h × pg/mL |
| $C_{max}$ | 194 pg/mL ± 113 pg/mL to 372 pg/mL ± 184 pg/mL |
| $T_{max}$ (mean) | 0.776 h ± 0.350 h to 1.065 h ± 1.156 h |
| $T_{max}$ (median) | 0.5 h to 1 h |
| $T_{max}$ (range) | [0.5 h-6 h] |

Acetaminophen Summary:
single oral dose from 6.67 mg to 13.34 mg of Bz-HC.HCl, fasted

TABLE 36

| Parameter | APAP Released from Bz-HC•HCl/APAP |
|---|---|
| $AUC_{0-24\,h}$ | 14.640 h × µg/mL ± 4.424 h × µg/mL to 30.526 h × µg/mL ± 12.736 h × µg/mL |
| $AUC_{inf}$ | 14.683 h × µg/mL ± 3.867 h × µg/mL to 28.945 h × µg/mL ± 7.069 h × µg/mL |
| $C_{max}$ | 4.048 µg/mL ± 1.300 µg/mL to 7.951 µg/mL ± 2.157 µg/mL |
| $T_{max}$ (mean) | 0.717 h ± 0.394 h to 1.054 h ± 0.708 h |
| $T_{max}$ (median) | 0.5 h to 1 h |
| $T_{max}$ (range) | [0.5 h-3 h] |
| $t_{1/2}$ | 4.781 h ± 1.303 h to 4.934 h ± 0.977 h |

Hydrocodone Summary:
single oral dose of Bz-HC.HCl/APAP, 6.67 mg/325 mg, fasted

TABLE 37

| Parameter | Hydrocodone Released from Bz-HC•HCl/APAP |
|---|---|
| $AUC_{0-24\,h}$ | 112.09 h × ng/mL ± 28.77 h × ng/mL to 132.62 h × ng/mL ± 34.20 h × ng/mL |
| $AUC_{inf}$ | 115.77 h × ng/mL ± 29.10 h × ng/mL to 136.50 h × ng/mL ± 34.90 h × ng/mL |
| $C_{max}$ | 16.86 ng/mL ± 4.15 ng/mL to 21.06 ng/mL ± 4.43 ng/mL |
| $T_{max}$ (mean) | 1.241 h ± 0.394 h to 1.595 h ± 0.922 h |
| $T_{max}$ (median) | 1 h to 1.25 h |
| $T_{max}$ (range) | [0.5 h-4 h] |
| $t_{1/2}$ | 4.190 h ± 0.638 h to 4.347 h ± 0.681 h |

Hydromorphone Summary:
single oral dose of Bz-HC.HCl/APAP, 6.67 mg/325 mg, fasted

TABLE 38

| Parameter | Hydromorphone Released from Bz-HC•HCl/APAP |
|---|---|
| $AUC_{0-24\,h}$ | 1,453 h × pg/mL ± 900 h × pg/mL to 1,741 h × pg/mL ± 896 h × pg/mL |
| $C_{max}$ | 224 pg/mL ± 137 pg/mL to 246 pg/mL ± 98 pg/mL |
| $T_{max}$ (mean) | 0.964 h ± 0.434 h to 1.185 h ± 0.798 h |
| $T_{max}$ (median) | 0.5 h to 1 h |
| $T_{max}$ (range) | [0.5 h-6 h] |

Acetaminophen Summary:
single oral dose of Bz-HC.HCl/APAP, 6.67 mg/325 mg, fasted

TABLE 39

| Parameter | APAP Released from Bz-HC•HCl/APAP |
|---|---|
| $AUC_{0-24\,h}$ | 16.388 h × µg/mL ± 3.987 h × µg/mL to 14.640 h × µg/mL ± 4.424 h × µg/mL |
| $AUC_{inf}$ | 17.220 h × µg/mL ± 3.696 h × µg/mL to 14.683 h × µg/mL ± 3.867 h × µg/mL |
| $C_{max}$ | 3.810 µg/mL ± 1.301 µg/mL to 4.067 µg/mL ± 1.319 µg/mL |
| $T_{max}$ (mean) | 0.717 h ± 0.394 h to 1.243 h ± 1.064 h |
| $T_{max}$ (median) | 0.5 h to 1 h |
| $T_{max}$ (range) | [0.5 h-4 h] |
| $t_{1/2}$ | 4.781 h ± 1.303 h to 5.269 h ± 1.856 h |

Example 21

Intact Bz-HC Pharmacokinetic Studies

LC/MS/MS analyses were performed in order to attempt to measure intact Bz-HC concentrations in the plasma samples obtained from any of the blood samples described above in Examples 14-19. However, all plasma concentrations of intact Bz-HC were <LLOQ (25 pg/mL) and no PK analyses could be performed In the present specification, use of the singular includes the plural except where specifically indicated.

The compositions, prodrugs, and methods described herein can be illustrated by the following embodiments enumerated in the numbered paragraphs that follow:

1. A composition comprising at least one conjugate of hydrocodone and at least one benzoic acid or benzoic acid derivative, a salt thereof, or a combination thereof, at least one benzoic acid or benzoic acid derivative having the following formula I:

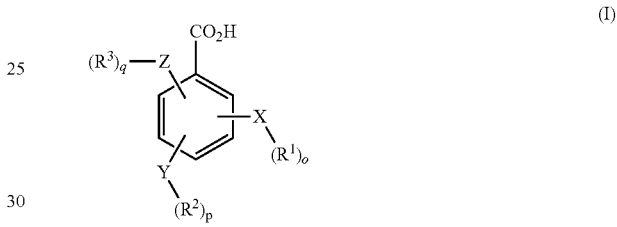

wherein,
X, Y and Z are independently selected from the group consisting of H, O, S, NH and —$(CH_2)_x$—;
$R^1$, $R^2$ and $R^3$ are independently selected from the group consisting of H, alkyl, alkoxy, aryl, alkenyl, alkynyl, halo, haloalkyl, alkylaryl, arylalkyl, heterocycle, arylalkoxy, cycloalkyl, cycloalkenyl and cycloalkynyl;
o, p, q are independently selected from 0 or 1; and
x is an integer between 1 and 10.

2. A composition comprising at least one conjugate of hydrocodone and at least one benzoic acid, a derivative thereof, or a combination thereof.

3. A composition comprising a benzoate conjugate, wherein the benzoate conjugate comprises at least one hydrocodone conjugated to at least one benzoic acid or benzoic acid derivative.

4. The composition of paragraph 1, wherein at least one benzoic acid or benzoic acid derivative is an aminobenzoate, a hydroxybenzoate, an aminohydroxybenzoate, a derivative thereof, or combination thereof.

5. The composition of paragraph 4, wherein the aminobenzoate is selected from the group consisting of: anthranilic acid, 3-aminobenzoic acid, 4,5-dimethylanthranilic acid, N-methylanthranilic acid, N-acetylanthranilic acid, fenamic acids (e.g., tolfenamic acid, mefenamic acid, flufenamic acid), 2,4-diaminobenzoic acid (2,4-DABA), 2-acetylamino-4-aminobenzoic acid, 4-acetylamino-2-aminobenzoic acid, 2,4-diacetylaminobenzoic acid, derivatives thereof and combinations thereof.

6. The composition of paragraph 4, wherein the hydroxybenzoate is selected from the group consisting of salicylic acid, acetylsalicylic acid (aspirin), 3-hydroxybenzoic acid, 4-hydroxybenzoic acid, 6-methylsalicylic acid, o,m,p-cresotinic acid, anacardic acids, 4,5-dimethylsalicylic acid, o,m,p-thymotic acid, diflusinal, o,m,p-anisic acid, 2,3-dihydroxybenzoic acid (2,3-DHB), α,β,γ-resorcylic acid, protocatechuic acid, gentisic acid, piperonylic acid, 3-methoxysalicylic acid, 4-methoxysalicylic acid, 5-methoxysalicylic acid, 6-methoxysalicylic acid, 3-hydroxy-2-methoxybenzoic acid, 4-hydroxy-2-methoxybenzoic acid, 5-hydroxy-2-methoxybenzoic acid, vanillic acid, isovanillic acid, 5-hydroxy-3-methoxybenzoic acid, 2,3-dimethoxybenzoic acid, 2,4-dimethoxybenzoic acid, 2,5-dimethoxybenzoic acid, 2,6-dimethoxybenzoic acid, veratric acid (3,4-dimethoxybenzoic acid), 3,5-dimethoxybenzoic acid, gallic acid, 2,3,4-trihydroxybenzoic acid, 2,3,6-trihydroxybenzoic acid, 2,4,5-trihydroxybenzoic acid, 3-O-methylgallic acid (3-OMGA), 4-O-methylgallic acid (4-OMGA), 3,4-O-dimethylgallic acid, syringic acid, 3,4,5-trimethoxybenzoic acid, derivatives thereof and combinations thereof.

7. The composition of paragraph 4, wherein the aminohydroxybenzoate is selected from the group consisting of 4-aminosalicylic acid, 3-hydroxyanthranilic acid, 3-methoxyanthranilic acid, derivatives thereof and combinations thereof.

8. The composition of paragraph 1, 2, 3, or 4, wherein at least one conjugate is a treatment or preventative composition used to treat narcotic or opioid abuse or prevent withdrawal.

9. The composition of paragraph 1, 2, 3, or 4, wherein at least one conjugate is a pain treatment composition.

10. The composition of paragraph 1, 2, 3, or 4, wherein at least one conjugate is moderate to severe pain treatment composition.

11. The composition of paragraph 1, 2, 3, or 4, wherein at least one conjugate reduces or prevents oral, intranasal or intravenous drug abuse.

12. The composition of paragraph 1, 2, 3, or 4, wherein at least one conjugate provides oral, intranasal or parenteral drug abuse resistance.

13. The composition of paragraph 1, 2, 3, or 4, wherein at least one conjugate exhibits an improved rate of release over time and AUC when compared to unconjugated hydrocodone over the same time period.

14. The composition of paragraph 1, 2, 3, or 4, wherein at least one conjugate exhibits less variability in the oral PK profile when compared to unconjugated hydrocodone.

15. The composition of paragraph 1, 2, 3, or 4, wherein at least one conjugate has reduced side effects when compared with unconjugated hydrocodone.

16. The composition of paragraph 1, 2, 3, or 4, wherein at least one conjugate prevents drug tampering by either physical or chemical manipulation.

17. The composition of paragraph 1, 2, 3, or 4, wherein at least one conjugate is provided in a dosage form selected from the group consisting of: a tablet, a capsule, a caplet, a suppository, a troche, a lozenge, an oral powder, a solution, an oral film, a thin strip, a slurry, and a suspension.

18. The composition of paragraph 1, 2, 3, or 4, wherein at least one conjugate is provided in an amount sufficient to provide a therapeutically bioequivalent AUC when compared to unconjugated hydrocodone.

19. The composition of paragraph 1, 2, 3, or 4, wherein at least one conjugate is provided in an amount sufficient to provide a therapeutically bioequivalent AUC and $C_{max}$ compared to an equivalent molar amount of unconjugated hydrocodone.

20. The composition of paragraph 1, 2, 3, or 4, wherein at least one conjugate is provided in an amount sufficient to provide a therapeutically bioequivalent AUC and a lower $C_{max}$ compared to an equivalent molar amount of unconjugated hydrocodone.

21. The composition of paragraph 1, 2, 3 or 4, wherein at least one conjugate is present in an amount of from about 0.5 mg or higher.

22. The composition of paragraph 1, 2, 3 or 4, wherein at least one conjugate is present in an amount of from about 2.5 mg or higher.

23. The composition of paragraph 1, 2, 3 or 4, wherein at least one conjugate is present in an amount of from about 5 mg or higher.

24. The composition of paragraph 1, 2, 3 or 4, wherein at least one conjugate is present in an amount of from about 10 mg or higher.

25. The composition of paragraph 1, 2, 3 or 4, wherein at least one conjugate is present in an amount of from about 20 mg or higher.

26. The composition of paragraph 1, 2, 3 or 4, wherein at least one conjugate is present in an amount of from about 50 mg or higher.

27. The composition of paragraph 1, 2, 3 or 4, wherein at least one conjugate is present in an amount of from about 100 mg or higher.

28. A method for treating a patient having a disease, disorder or condition requiring or mediated by binding of an opioid to opioid receptors of the patient, comprising orally administering to the patient a pharmaceutically effective amount of at least one conjugate of hydrocodone and at least one benzoic acid or benzoic acid derivative, a salt thereof, or a combination thereof, the benzoic acid or benzoic acid derivative having formula I:

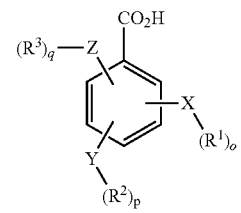

wherein

X, Y and Z are independently selected from the group consisting of H, O, S, NH and $-(CH_2)_x-$;

$R^1$, $R^2$ and $R^3$ are independently selected from the group consisting of H, alkyl, alkoxy, aryl, alkenyl, alkynyl, halo, haloalkyl, alkylaryl, arylalkyl, heterocycle, arylalkoxy, cycloalkyl, cycloalkenyl and cycloalkynyl;

o, p, q are independently selected from 0 or 1; and x is an integer between 1 and 10.

29. The method of paragraph 28, wherein at least one conjugate exhibits a slower rate of release over time and greater AUC when compared to an equivalent molar amount of unconjugated hydrocodone over the same time period.

30. The method of paragraph 28, wherein at least one conjugate exhibits less variability in the oral PK profile when compared to unconjugated hydrocodone.

31. The method of paragraph 28, wherein at least one conjugate has reduced side effects when compared with unconjugated hydrocodone.

32. The method of paragraph 28, wherein at least one conjugate is provided in a dosage form selected from the group consisting of: a tablet, a capsule, a caplet, a suppository, a troche, a lozenge, an oral powder, a solution, an oral film, a thin strip, a slurry, and a suspension.

33. The method of paragraph 28, wherein at least one conjugate is provided in an amount sufficient to provide a therapeutically bioequivalent AUC when compared to a molar equivalent amount of unconjugated hydrocodone.

34. The method of paragraph 28, wherein at least one conjugate is provided in an amount sufficient to provide a therapeutically bioequivalent AUC and when compared to a molar equivalent amount of unconjugated hydrocodone.

35. The method of paragraph 28, wherein at least one conjugate is provided in an amount sufficient to provide a therapeutically bioequivalent AUC and a lower $C_{max}$ when compared to a molar equivalent amount of unconjugated hydrocodone.

36. The method of paragraph 28, wherein at least one conjugate is present in an amount of from about 0.5 mg or higher.

37. The method of paragraph 28, wherein at least one conjugate is present in an amount of from about 2.5 mg or higher.

38. The method of paragraph 28, wherein at least one conjugate is present in an amount of from about 5 mg or higher.

39. The method of paragraph 28, wherein at least one conjugate is present in an amount of from about 10 mg or higher.

40. The method of paragraph 28, wherein at least one conjugate is present in an amount of from about 20 mg or higher.

41. The method of paragraph 28, wherein at least one conjugate is present in an amount of from about 50 mg or higher.

42. The method of paragraph 28, wherein at least one conjugate is present in an amount of from about 100 mg or higher.

43. The method of paragraph 28, wherein at least one conjugate binds reversibly to the opioid receptors of the patient.

44. The method of paragraph 28, wherein at least one conjugate prevents or reduces at least one constipatory side effect of unconjugated hydrocodone.

45. The method of paragraph 28, wherein at least one conjugate exhibits reduced or prevented constipatory effects when compared with unconjugated hydrocodone.

46. The method of paragraph 28, wherein at least one conjugate binds irreversibly to the opioid receptors of the patient.

47. A method for treating a patient having a disease, disorder or condition requiring or mediated by inhibiting binding of an opioid to opioid receptors of the patient, comprising orally administering to the patient a pharmaceutically effective amount of at least one conjugate of hydrocodone and at least one benzoic acid or benzoic acid derivative, a salt thereof, or a combination thereof, the benzoic acid or benzoic acid derivative having formula I:

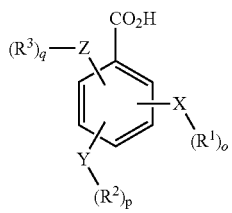

(I)

wherein
X, Y and Z are independently selected from the group consisting of H, O, S, NH and —$(CH_2)_x$—;

$R^1$, $R^2$ and $R^3$ are independently selected from the group consisting of H, alkyl, alkoxy, aryl, alkenyl, alkynyl, halo, haloalkyl, alkylaryl, arylalkyl, heterocycle, arylalkoxy, cycloalkyl, cycloalkenyl and cycloalkynyl;

o, p, q are independently selected from 0 or 1; and x is an integer between 1 and 10.

48. The method of paragraph 47, wherein at least one conjugate reversibly inhibits binding of an opioid to the opioid receptor of the patient.

49. The method of paragraph 47, wherein at least one conjugate prevents or reduces at least one constipatory side effect of hydrocodone alone.

50. A method for treating a patient having a disease, disorder or condition requiring or mediated by binding of an opioid to opioid receptors of the patient, comprising orally administering to the patient a pharmaceutically effective amount of at least one conjugate of hydrocodone and at least one benzoic acid, a salt thereof, a derivative thereof or a combination thereof.

51. The method of paragraph 50, wherein at least one conjugate provides a slower rate of release over time and higher AUC when compared to an equivalent molar amount of unconjugated hydrocodone over the same time period.

52. The method of paragraph 50, wherein at least one conjugate exhibits less variability in the oral PK profile when compared to hydrocodone alone.

53. The method of paragraph 50, wherein at least one conjugate has reduced side effects when compared with hydrocodone alone.

54. The method of paragraph 50, wherein at least one conjugate is provided in a dosage form selected from the group consisting of: a tablet, a capsule, a caplet, a suppository, a troche, a lozenge, an oral powder, a solution, an oral film, a thin strip, a slurry, and a suspension.

55. The method of paragraph 50, wherein at least one conjugate is provided in an amount sufficient to provide a bioequivalent, and thus therapeutically equivalent, AUC when compared to hydrocodone alone.

56. The method of paragraph 50, wherein at least one conjugate is provided in an amount sufficient to provide a bioequivalent, and thus therapeutically equivalent, AUC and $C_{max}$ when compared to hydrocodone alone.

57. The method of paragraph 50, wherein at least one conjugate is provided in an amount sufficient to provide a bioequivalent, and thus therapeutically equivalent, AUC when compared to hydrocodone alone with a lower $C_{max}$.

58. The method of paragraph 50, wherein at least one conjugate is provided in an amount sufficient to provide a bioequivalent, and thus therapeutically equivalent, AUC when compared to hydrocodone alone, but does not provide an equivalent $C_{max}$.

59. The method of paragraph 50, wherein at least one conjugate is present in an amount of from about 0.5 mg or higher.

60. The method of paragraph 50, wherein at least one conjugate is present in an amount of from about 2.5 mg or higher.

61. The method of paragraph 50, wherein at least one conjugate is present in an amount of from about 5 mg or higher.

62. The method of paragraph 50, wherein at least one conjugate is present in an amount of from about 10 mg or higher.

63. The method of paragraph 50, wherein at least one conjugate is present in an amount of from about 20 mg or higher.

64. The method of paragraph 50, wherein at least one conjugate is present in an amount of from about 50 mg or higher.
65. The method of paragraph 50, wherein at least one conjugate is present in an amount of from about 100 mg or higher.
66. The method of paragraph 50, wherein at least one conjugate binds reversibly to the opioid receptors of the patient.
67. The method of paragraph 50, wherein at least one conjugate prevents or reduces at least one constipatory side effect of hydrocodone alone.
68. The method of paragraph 50, wherein at least one conjugate exhibits reduced or prevented constipatory effects.
69. The method of paragraph 50, wherein at least one conjugate binds permanently to the opioid receptors of the patient.
70. A method for treating a patient having a disease, disorder or condition requiring or mediated by inhibiting binding of an opioid to opioid receptors of the patient, comprising orally administering to the patient a pharmaceutically effective amount of at least one conjugate of hydrocodone and at least one benzoic acid, a salt thereof, a derivative thereof or a combination thereof.
71. The method of paragraph 70, wherein at least one conjugate reversibly inhibits binding of an opioid to the opioid receptor of the patient.
72. The method of paragraph 70, wherein at least one conjugate prevents or reduces at least one constipatory side effect of hydrocodone alone.
73. A pharmaceutical kit comprising:
a specified amount of individual doses in a package containing a pharmaceutically effective amount of at least one conjugate of hydrocodone and at least one benzoic acid or benzoic acid derivative, a salt thereof, or a combination thereof, the benzoic acid or benzoic acid derivative having the formula I:

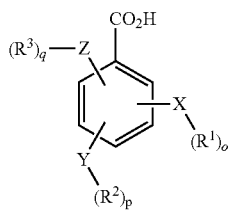

(I)

wherein
X, Y and Z are independently selected from the group consisting of H, O, S, NH and —$(CH_2)_x$—;
$R^1$, $R^2$ and $R^3$ are independently selected from the group consisting of H, alkyl, alkoxy, aryl, alkenyl, alkynyl, halo, haloalkyl, alkylaryl, arylalkyl, heterocycle, arylalkoxy, cycloalkyl, cycloalkenyl and cycloalkynyl;
o, p, q can be independently selected from 0 or 1; and
x is an integer between 1 and 10
74. The kit of paragraph 73, wherein the kit further comprises:
(ii) instructions for use of the kit in a method for treating or preventing drug withdrawal symptoms or pain in a human or animal patient.
75. The kit of paragraph 74, wherein the patient is a pediatric patient.
76. The kit of paragraph 74, wherein the patient is an elderly patient.
77. The kit of paragraph 74, wherein the patient is a normative patient.
78. A pharmaceutical kit comprising:
a specified amount of individual doses in a package containing a pharmaceutically effective amount of at least one conjugate of hydrocodone and at least one benzoic acid, a salt thereof, a derivative thereof or a combination thereof.
79. The kit of paragraph 78, wherein the kit further comprises:
(ii) instructions for use of the kit in a method for treating or preventing drug withdrawal symptoms or pain in a human or animal patient.
80. The kit of paragraph 79, wherein the patient is a pediatric patient.
81. The kit of paragraph 79, wherein the patient is an elderly patient.
82. The kit of paragraph 79, wherein the patient is a normative patient.
83. The kit of paragraph 73, 74, 78, or 79, wherein the individual dosages comprise at least about 0.5 mg or higher of at least one conjugate.
84. The kit of paragraph 73, 74, 78, or 79, wherein the individual dosages comprise at least about 2.5 mg or higher of at least one conjugate.
85. The kit of paragraph 73, 74, 78, or 79, wherein the individual dosages comprise at least about 5.0 mg or higher of at least one conjugate.
86. The kit of paragraph 73, 74, 78, or 79, wherein the individual dosages comprise at least about 10 mg or higher of at least one conjugate.
87. The kit of paragraph 73, 74, 78, or 79, wherein the individual dosages comprise at least about 20 mg or higher of at least one conjugate.
88. The kit of paragraph 73, 74, 78, or 79, wherein the individual dosages comprise at least about 50 mg or higher of at least one conjugate.
89. The kit of paragraph 73, 74, 78, or 79, wherein the individual dosages comprise at least about 100 mg or higher of at least one conjugate.
90. The kit of paragraph 73, 74, 78, or 79, wherein the kit comprises from about 1 to about 60 individual doses.
91. The kit of paragraph 73, 74, 78, or 79, wherein the kit comprises from about 10 to about 30 individual doses.
92. A composition comprising at least one conjugate of hydrocodone and at least one heteroaryl carboxylic acid, a derivative thereof, or a combination thereof.
93. The composition of paragraph 92, wherein at least one heteroaryl carboxylic acid is selected from formula II, formula III or formula IV,
wherein formula II, formula III and formula IV are:

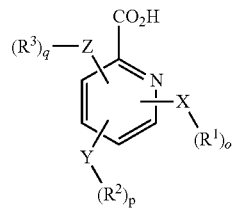

(II)

-continued

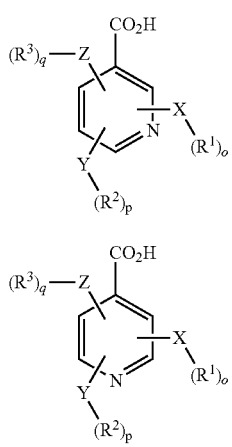

wherein

X, Y and Z are independently selected from the group consisting of H, O, S, NH and —(CH$_2$)$_x$—;

R$^1$, R$^2$ and R$^3$ are independently selected from the group consisting of H, alkyl, alkoxy, aryl, alkenyl, alkynyl, halo, haloalkyl, alkylaryl, arylalkyl, heterocycle, arylalkoxy, cycloalkyl, cycloalkenyl and cycloalkynyl;

o, p, q are independently selected from 0 or 1; and x is an integer from 1 to 10.

94. A composition comprising at least one conjugate of hydrocodone and at least one nicotinic acid, a derivative thereof, or a combination thereof.

95. The composition of paragraph 92, wherein at least one heteroaryl carboxylic acid is a pyridine derivative.

96 The composition of paragraph 92, wherein the heteroaryl carboxylic acid is selected from the group consisting of, isonicotinic acid, picolinic acid, 3-hydroxypicolinic acid, 6-hydroxynicotinic acid, citrazinic acid, 2,6-dihydroxynicotinic acid, kynurenic acid, xanthurenic acid, 6-hydroxykynurenic acid, 8-methoxykynurenic acid, 7,8-dihydroxykynurenic acid, 7,8-dihydro-7,8-dihydroxykynurenic acid, derivatives thereof and combinations thereof.

97. The composition of paragraph 92, 93, or 94, wherein at least one conjugate is used to treat drug, narcotic or opioid abuse or prevent withdrawal.

98. The composition of paragraph 92, 93, or 94, wherein at least one conjugate is used to treat pain.

99. The composition of paragraph 92, 93, or 94, wherein at least one conjugate is used to treat moderate to severe pain.

100. The composition of paragraph 92, 93, or 94, wherein at least one conjugate reduces or prevents oral, intranasal or intravenous drug abuse.

101. The composition of paragraph 92, 93, or 94, wherein at least one conjugate provides oral, intranasal or parenteral drug abuse resistance.

102. The composition of paragraph 92, 93, or 94, wherein at least one conjugate prevents drug tampering by either physical or chemical manipulation.

103. The composition of paragraph 92, 93, or 94, wherein at least one conjugate exhibits an improved rate of release over time and AUC when compared to a molar equivalent of unconjugated hydrocodone alone over the same time period.

104. The composition of paragraph 92, 93, or 94, wherein at least one conjugate exhibits less variability in the oral PK profile when compared to a molar equivalent of unconjugated hydrocodone alone.

105. The composition of paragraph 92, 93, or 94, wherein at least one conjugate has reduced side effects when compared with hydrocodone alone.

106. The composition of paragraph 92, 93, or 94, wherein the composition is provided in a dosage form selected from the group consisting of: a tablet, a capsule, a caplet, a suppository, a troche, a lozenge, an oral powder, a solution, an oral film, a thin strip, a slurry, and a suspension.

107. The composition of paragraph 92, 93, or 94, wherein at least one conjugate is provided in an amount sufficient to provide a bioequivalent, and thus therapeutically equivalent, AUC when compared to a molar equivalent of unconjugated hydrocodone alone.

108. The composition of paragraph 92, 93, or 94, wherein at least one conjugate is provided in an amount sufficient to provide a bioequivalent, and thus therapeutically equivalent, AUC and C$_{max}$ when compared to hydrocodone alone.

109. The composition of paragraph 92, 93, or 94, wherein at least one conjugate is provided in an amount sufficient to provide a bioequivalent, and thus therapeutically equivalent, AUC when compared to hydrocodone alone, with a lower C$_{max}$.

110. The composition of paragraph 92, 93, or 94, wherein at least one conjugate is present in an amount of from about 0.5 mg or higher.

111. The composition of paragraph 92, 93, or 94, wherein at least one conjugate is present in an amount of from about 2.5 mg or higher.

112. The composition of paragraph 92, 93, or 94, wherein at least one conjugate is present in an amount of from about 5 mg or higher.

113. The composition of paragraph 92, 93, or 94, wherein at least one conjugate is present in an amount of from about 10 mg or higher.

114. The composition of paragraph 92, 93, or 94, wherein at least one conjugate is present in an amount of from about 20 mg or higher.

115. The composition of paragraph 92, 93, or 94, wherein at least one conjugate is present in an amount of from about 50 mg or higher.

116. The composition of paragraph 92, 93, or 94, wherein at least one conjugate is present in an amount of from about 100 mg or higher.

117. A method for treating a patient having a disease, disorder or condition requiring or mediated by binding of an opioid to opioid receptors of the patient, comprising orally administering to the patient a pharmaceutically effective amount of at least one conjugate of hydrocodone and at least one heteroaryl carboxylic acid.

118. The method of paragraph 117, wherein at least one heteroaryl carboxylic acid is selected from formula II, formula III or formula IV, wherein formula II, formula III and formula IV are:

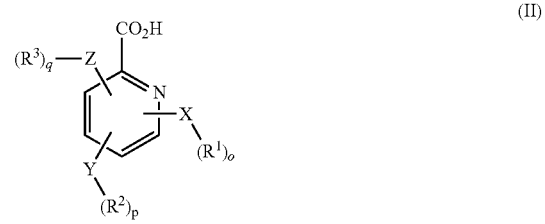

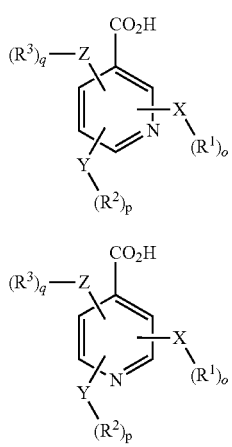

wherein

X, Y and Z are independently selected from the group consisting of H, O, S, NH and $-(CH_2)_x-$;

$R^1$, $R^2$ and $R^3$ are independently selected from the group consisting of H, alkyl, alkoxy, aryl, alkenyl, alkynyl, halo, haloalkyl, alkylaryl, arylalkyl, heterocycle, arylalkoxy, cycloalkyl, cycloalkenyl and cycloalkynyl;

o, p, q are independently selected from 0 or 1; and x is an integer from 1 to 10.

119. A method for treating a patient having a disease, disorder or condition requiring or mediated by binding of an opioid to one or more opioid receptors of the patient, comprising orally administering to the patient a pharmaceutically effective amount of at least one conjugate of hydrocodone and at least one nicotinic acid, a derivative thereof, or a combination thereof.

120. The method of paragraph 117, 118, or 119, wherein at least one conjugate exhibits an improved rate of release over time and AUC when compared to hydrocodone alone over the same time period.

121. The method of paragraph 117, 118, or 119, wherein at least one conjugate exhibits less variability in the oral PK profile when compared to hydrocodone alone.

122. The method of paragraph 117, 118, or 119, wherein at least one conjugate has reduced side effects when compared to hydrocodone alone.

123. The method of paragraph 117, 118, or 119, wherein at least one conjugate is provided in a dosage from selected from the group consisting of: a tablet, a capsule, a caplet, a suppository, a troche, a lozenge, an oral powder, a solution, an oral film, a thin strip, a slurry, and a suspension.

124. The method of paragraph 117, 118, or 119, wherein at least one conjugate is provided in an amount sufficient to provide a bioequivalent, and thus therapeutically equivalent, AUC when compared to an equivalent molar amount of unconjugated hydrocodone.

125. The method of paragraph 117, 118, or 119, wherein at least one conjugate is provided in an amount sufficient to provide a bioequivalent, and thus therapeutically equivalent, AUC and $C_{max}$ when compared to an equivalent molar amount of unconjugated hydrocodone.

126. The method of paragraph 117, 118, or 119, wherein at least one conjugate is provided in an amount sufficient to provide a bioequivalent, and thus therapeutically equivalent, AUC and a lower $C_{max}$ compared to the same molar amount of unconjugated hydrocodone.

127. The method of paragraph 117, 118, or 119, wherein at least one conjugate is provided in an amount sufficient to provide a bioequivalent, and thus therapeutically equivalent, AUC when compared to hydrocodone alone, but does not provide an equivalent $C_{max}$.

128. The method of paragraph 117, 118, or 119, wherein at least one conjugate is present in an amount of from about 0.5 mg or higher.

129. The method of paragraph 117, 118, or 119, wherein at least one conjugate is present in an amount of from about 2.5 mg or higher.

130. The method of paragraph 117, 118, or 119, wherein at least one conjugate is present in an amount of from about 5 mg or higher.

131. The method of paragraph 117, 118, or 119, wherein at least one conjugate is present in an amount of from about 10 mg or higher.

132. The method of paragraph 117, 118, or 119, wherein at least one conjugate is present in an amount of from about 20 mg or higher.

133. The method of paragraph 117, 118, or 119, wherein at least one conjugate is present in an amount of from about 50 mg or higher.

134. The method of paragraph 117, 118, or 119, wherein at least one conjugate is present in an amount of from about 100 mg or higher.

135. The method of paragraph 117, 118, or 119, wherein at least one conjugate binds reversibly to one or more opioid receptors of the patient.

136. The method of paragraph 117, 118, or 119, wherein at least one conjugate prevents or reduces at least one constipatory side effect of hydrocodone alone.

137. The method of paragraph 117, 118, or 119, wherein at least one conjugate exhibits reduced or prevented constipatory effects.

138. The method of paragraph 117, 118, or 119, wherein at least one conjugate binds permanently to the opioid receptors of the patient.

139. A method for treating a patient having a disease, disorder or condition requiring or mediated by inhibiting binding of an opioid to opioid receptors of the patient, comprising orally administering to the patient a pharmaceutically effective amount of at least one conjugate of hydrocodone and at least one heteroaryl carboxylic acid.

140. The method of paragraph 139, wherein at least one heteroaryl carboxylic acid is selected from formula II, formula III or formula IV, wherein formula II, formula III and formula IV are:

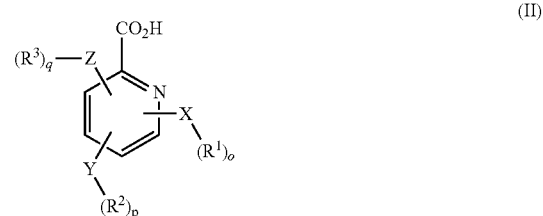

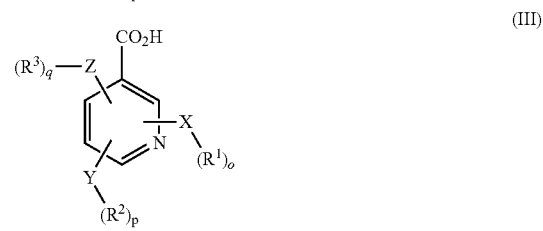

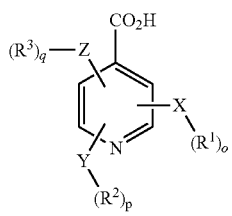

wherein

X, Y and Z are independently selected from the group consisting of H, O, S, NH and —(CH$_2$)$_x$—;

R$^1$, R$^2$ and R$^3$ are independently selected from the group consisting of H, alkyl, alkoxy, aryl, alkenyl, alkynyl, halo, haloalkyl, alkylaryl, arylalkyl, heterocycle, arylalkoxy, cycloalkyl, cycloalkenyl and cycloalkynyl;

o, p, q are independently selected from 0 or 1; and x is an integer from 1 to 10.

141. A method for treating a patient having a disease, disorder or condition requiring or mediated by inhibiting binding of an opioid to opioid receptors of the patient, comprising orally administering to the patient a pharmaceutically effective amount of at least one conjugate of hydrocodone and at least one nicotinic acid, a derivative thereof, or a combination thereof.

142. The method of paragraph 139, 140, or 141, wherein at least one conjugate reversibly inhibits binding of an opioid to the opioid receptor of the patient.

143. The method of paragraph 139, 140, or 141, wherein at least one conjugate prevents or reduces at least one constipatory side effect of hydrocodone alone.

144. A pharmaceutical kit comprising:

a specified number of individual doses in a package containing a pharmaceutically effective amount of at least one conjugate of hydrocodone and at least one heteroaryl carboxylic acid, a derivative thereof, or a combination thereof, wherein at least one heteroaryl carboxylic acid is selected from formula II, formula III or formula IV, wherein formula II, formula III and formula IV are:

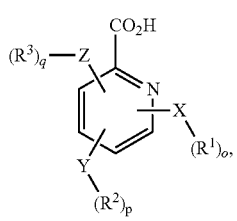

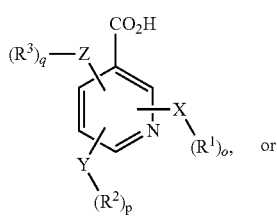

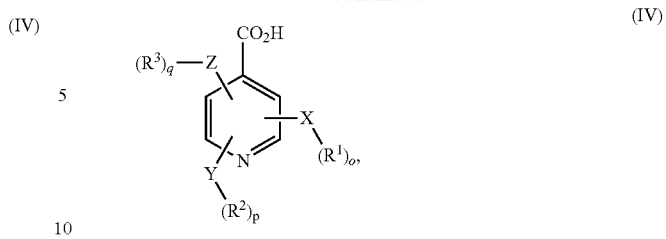

wherein

X, Y and Z are independently selected from the group consisting of H, O, S, NH and —(CH$_2$)$_x$—;

R$^1$, R$^2$ and R$^3$ are independently selected from the group consisting of H, alkyl, alkoxy, aryl, alkenyl, alkynyl, halo, haloalkyl, alkylaryl, arylalkyl, heterocycle, arylalkoxy, cycloalkyl, cycloalkenyl and cycloalkynyl;

o, p, q are independently selected from 0 or 1; and x is an integer from 1 to 10.

145. The kit of paragraph 144, wherein the kit further comprises:

(ii) instructions for use of the kit in a method for treating or preventing drug withdrawal symptoms or pain in a human or animal patient.

146. The kit of paragraph 145, wherein the patient is a pediatric patient.

147. The kit of paragraph 145, wherein the patient is an elderly patient.

148. The kit of paragraph 145, wherein the patient is a normative patient.

149. The kit of paragraph 144 or 145, wherein the individual dosages comprise at least about 0.5 mg or higher of at least one conjugate.

150. The kit of paragraph 144 or 145, wherein the individual dosages comprise at least about 2.5 mg or higher of at least one conjugate.

151. The kit of paragraph 144 or 145, wherein the individual dosages comprise at least about 5.0 mg or higher of at least one conjugate.

152. The kit of paragraph 144 or 145, wherein the individual dosages comprise at least about 10 mg or higher of at least one conjugate.

153. The kit of paragraph 144 or 145, wherein the individual dosages comprise at least about 20 mg or higher of at least one conjugate.

154. The kit of paragraph 144 or 145, wherein the individual dosages comprise at least about 50 mg or higher of at least one conjugate.

155. The kit of paragraph 144 or 145, wherein the individual dosages comprise at least about 100 mg or higher of at least one conjugate.

156. The kit of paragraph 144 or 145, wherein the kit comprises from about 1 to about 60 individual doses.

157. The kit of paragraph 144 or 145, wherein the kit comprises from about 10 to about 30 individual doses.

158. A prodrug comprising at least one conjugate of hydrocodone and at least one benzoic acid or benzoic acid derivative, a salt thereof, a or a combination thereof, the benzoic acid or benzoic acid derivative having the following formula I:

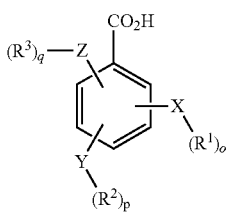

wherein,

X, Y and Z are independently selected from the group consisting of H, O, S, NH and —$(CH_2)_x$—;

$R^1$, $R^2$ and $R^3$ are independently selected from the group consisting of H, alkyl, alkoxy, aryl, alkenyl, alkynyl, halo, haloalkyl, alkylaryl, arylalkyl, heterocycle, arylalkoxy, cycloalkyl, cycloalkenyl and cycloalkynyl;

o, p, q are independently selected from 0 or 1; and x is an integer between 1 and 10.

159. A prodrug comprising at least one conjugate of hydrocodone and at least one benzoic acid, a derivative thereof, or a combination thereof.

160. A prodrug comprising a benzoate conjugate, wherein the benzoate conjugate comprises at least one hydrocodone conjugated to at least one benzoic acid or benzoic acid derivative.

161. A prodrug comprising at least one conjugate of hydrocodone and at least one heteroaryl carboxylic acid, a derivative thereof, or a combination thereof.

162. The prodrug of paragraph 161, wherein the heteroaryl carboxylic acid is selected from formula II, formula III or formula IV, wherein formula II, formula III and formula IV are:

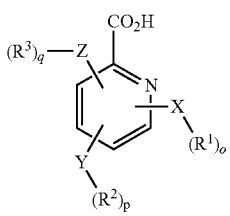

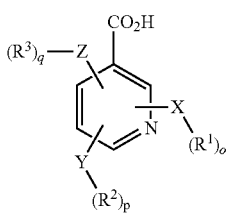

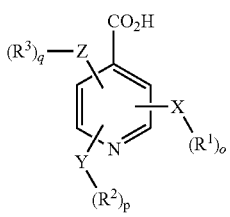

wherein

X, Y and Z are independently selected from the group consisting of H, O, S, NH and —$(CH_2)_x$—;

$R^1$, $R^2$ and $R^3$ are independently selected from the group consisting of H, alkyl, alkoxy, aryl, alkenyl, alkynyl, halo, haloalkyl, alkylaryl, arylalkyl, heterocycle, arylalkoxy, cycloalkyl, cycloalkenyl and cycloalkynyl;

o, p, q are independently selected from 0 or 1; and x is an integer from 1 to 10.

163. A prodrug comprising at least one conjugate of hydrocodone and at least one nicotinic acid, a derivative thereof, or a combination thereof.

164. The prodrug of paragraph 158, wherein the benzoic acid derivative is an aminobenzoate, a hydroxybenzoate, an aminohydroxybenzoate, a derivative thereof, or combination thereof.

165. The composition of paragraph 1 or 2, wherein at least one conjugate exhibits less variability in intranasal PK profiles when compared to unconjugated hydrocodone.

166. The composition of paragraph 1 or 2, wherein at least one conjugate exhibits less variability in the parenteral PK profiles when compared to unconjugated hydrocodone.

167. The composition of paragraph 1 or 2, wherein at least one conjugate exhibits less variability in the intravenous PK profile when compared to unconjugated hydrocodone.

The presently described technology is now described in such full, clear, concise and exact terms as to enable any person skilled in the art to which it pertains, to practice the same. It is to be understood that the foregoing describes preferred embodiments of the technology and that modifications may be made therein without departing from the spirit or scope of the invention as set forth in the appended claims.

The invention claimed is:

1. A composition comprising 13.34 mg benzoate-hydrocodone hydrochloride conjugate, wherein the conjugate has the following structure:

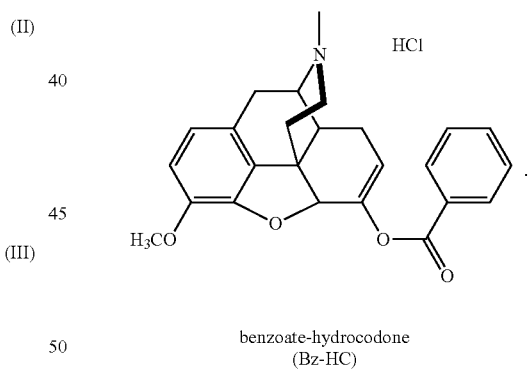

benzoate-hydrocodone
(Bz-HC)

2. The composition of claim 1, wherein the 13.34 mg benzoate-hydrocodone hydrochloride contains a molar equivalent of 9.08 mg of hydrocodone.

3. The composition of claim 1, wherein the conjugate results in the mean $C_{max}$ of hydrocodone of about 25,600 pg/mL±6,390 pg/mL when administered intranasally to a human.

4. The composition of claim 1, wherein the conjugate results in the mean $T_{max}$ of hydrocodone of about 2 hours±0.91 hours when administered intranasally to a human.

5. The composition of claim 1, wherein the conjugate results in the range of $T_{max}$ of hydrocodone from about 0.75 hours to about 4 hours when administered intranasally to a human.

6. The composition of claim 1, wherein the conjugate results in the mean $AUC_{0\text{-}0.083\ h}$ of hydrocodone of about 11.30 h×pg/mL±14.14 h×pg/mL when administered intranasally to a human.

7. The composition of claim 1, wherein the conjugate results in the mean $AUC_{0\text{-}0.25\ h}$ of hydrocodone of about 297.9 h×pg/mL±170.3 h×pg/mL when administered intranasally to a human.

8. The composition of claim 1, wherein the conjugate results in the mean $AUC_{0\text{-}0.5\ h}$ of hydrocodone of about 1,485 h×pg/mL±667.7 h×pg/mL when administered intranasally to a human.

9. The composition of claim 1, wherein the conjugate results in the mean $AUC_{0\text{-}0.75\ h}$ of hydrocodone of about 3,831 h×pg/mL±1,726 h×pg/mL when administered intranasally to a human.

10. The composition of claim 1, wherein the conjugate results in the mean $AUC_{0\text{-}1\ h}$ of hydrocodone of about 7,714 h×pg/mL±3,597 h×pg/mL when administered intranasally to a human.

11. The composition of claim 1, wherein the conjugate results in the mean $AUC_{0\text{-}1.5\ h}$ of hydrocodone of about 17,790 h×pg/mL±7,695 h×pg/mL when administered intranasally to a human.

12. The composition of claim 1, wherein the conjugate results in the mean $AUC_{0\text{-}2\ h}$ of hydrocodone of about 28,690 h×pg/mL±10,360 h×pg/mL when administered intranasally to a human.

13. The composition of claim 1, wherein the conjugate results in the mean $AUC_{0\text{-}3\ h}$ of hydrocodone of about 49,510 h×pg/mL±13,290 h×pg/mL when administered intranasally to a human.

14. The composition of claim 1, wherein the conjugate results in the mean $AUC_{0\text{-}4\ h}$ of hydrocodone about 68,360 h×pg/mL±15,540 h×pg/mL when administered intranasally to a human.

15. The composition of claim 1, wherein the conjugate results in the mean $AUC_{0\text{-}6\ h}$ of hydrocodone of about 99,100 h×pg/mL±20,450 h×pg/mL when administered intranasally to a human.

16. The composition of claim 1, wherein the conjugate results in the mean $AUC_{0\text{-}8\ h}$ of hydrocodone of about 121,100 h×pg/mL±25,710 h×pg/mL when administered intranasally to a human.

17. The composition of claim 1, wherein the conjugate results in the mean $AUC_{0\text{-}10\ h}$ of hydrocodone of about 137,200 h×pg/mL±30,610 h×pg/mL when administered intranasally to a human.

18. The composition of claim 1, wherein the conjugate results in the mean $AUC_{0\text{-}12\ h}$ of hydrocodone of about 149,000 h×pg/mL±34,890 h×pg/mL when administered intranasally to a human.

19. The composition of claim 1, wherein the conjugate results in the mean $AUC_{0\text{-}24\ h}$ of hydrocodone of about 185,500 h×pg/mL±50,470 h×pg/mL when administered intranasally to a human.

20. The composition of claim 1, wherein the conjugate results in the mean $AUC_{inf}$ of hydrocodone of about 194,700 h×pg/mL±55,690 h×pg/mL when administered intranasally to a human.

21. The composition of claim 1, wherein the conjugate results in the mean $t_{1/2}$ of hydrocodone of about 5.29 hours±0.78 hours when administered intranasally to a human.

22. The composition of claim 1 further comprising 650 mg acetaminophen.

23. The composition of claim 22, wherein the conjugate results in the mean $C_{max}$ of hydrocodone of about 34,700 pg/mL±8,690 pg/mL when administered intranasally to a human.

24. The composition of claim 22, wherein the conjugate results in the median $T_{max}$ of hydrocodone of about 1.23 hours when administered intranasally to a human.

25. The composition of claim 22, wherein the conjugate results in the range of $T_{max}$ of hydrocodone from about 0.52 hours to about 2.23 hours when administered intranasally to a human.

26. The composition of claim 22, wherein the conjugate results in the mean $AUC_{0\text{-}0.5\ h}$ of hydrocodone of about 4,767 h×pg/mL±2,313 h×pg/mL when administered intranasally to a human.

27. The composition of claim 22, wherein the conjugate results in the mean $AUC_{0\text{-}1\ h}$ of hydrocodone of about 18,640 h×pg/mL±6,222 h×pg/mL when administered intranasally to a human.

28. The composition of claim 22, wherein the conjugate results in the mean $AUC_{0\text{-}2\ h}$ of hydrocodone of about 50,120 h×pg/mL±12,060 h×pg/mL when administered intranasally to a human.

29. The composition of claim 22, wherein the conjugate results in the mean $AUC_{0\text{-}4\ h}$ of hydrocodone about 103,200 h×pg/mL±23,210 h×pg/mL when administered intranasally to a human.

30. The composition of claim 22, wherein the conjugate results in the mean $AUC_{0\text{-}8\ h}$ of hydrocodone of about 173,300 h×pg/mL±38,750 h×pg/mL when administered intranasally to a human.

31. The composition of claim 22, wherein the conjugate results in the mean $AUC_{0\text{-}24\ h}$ of hydrocodone of about 264,800 h×pg/mL±67,650 h×pg/mL when administered intranasally to a human.

32. The composition of claim 22, wherein the conjugate results in the mean $AUC_{inf}$ of hydrocodone of about 278,300 h×pg/mL±75,130 h×pg/mL when administered intranasally to a human.

33. The composition of claim 22, wherein the conjugate results in the mean $t_{1/2}$ of hydrocodone of about 5.23 hours±0.87 hours when administered intranasally to a human.

34. A composition comprising 26.68 mg benzoate-hydrocodone hydrochloride conjugate, wherein the conjugate has the following structure:

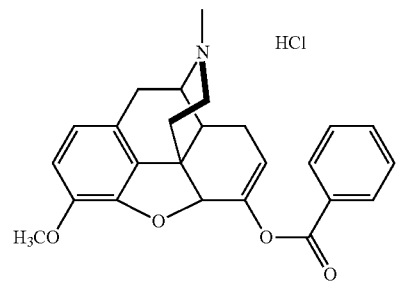

benzoate-hydrocodone
(Bz-HC)

35. The composition of claim 34 further comprising 1300 mg acetaminophen.

36. The composition of claim 35, wherein the conjugate results in the mean $C_{max}$ of hydrocodone of about 75,100 pg/mL±25,500 pg/mL when administered orally to a human.

37. The composition of claim 35, wherein the conjugate results in the mean $T_{max}$ of hydrocodone of about 1.17 hours when administered orally to a human.

38. The composition of claim 35, wherein the conjugate results in the range of $T_{max}$ of hydrocodone from about 0.6 hours to about 4.12 hours when administered orally to a human.

39. The composition of claim 35, wherein the conjugate results in the mean $AUC_{0-0.5\ h}$ of hydrocodone of about 12,530 h×pg/mL±7,213 h×pg/mL when administered orally to a human.

40. The composition of claim 35, wherein the conjugate results in the mean $AUC_{0-1\ h}$ of hydrocodone of about 42,520 h×pg/mL±20,200 h×pg/mL when administered orally to a human.

41. The composition of claim 35, wherein the conjugate results in the mean $AUC_{0-2\ h}$ of hydrocodone of about 95,850 h×pg/mL±29,510 h×pg/mL when administered orally to a human.

42. The composition of claim 35, wherein the conjugate results in the mean $AUC_{0-4\ h}$ of hydrocodone of about 172,200 h×pg/mL±39,550 h×pg/mL when administered orally to a human.

43. The composition of claim 35, wherein the conjugate results in the mean $AUC_{0-8\ h}$ of hydrocodone of about 269,000 h×pg/mL±51,840 h×pg/mL when administered orally to a human.

44. The composition of claim 35, wherein the conjugate results in the mean $AUC_{0-24\ h}$ of hydrocodone of about 382,100 h×pg/mL±81,260 h×pg/mL when administered orally to a human.

45. The composition of claim 35, wherein the conjugate results in the mean $AUC_{inf}$ of hydrocodone of about 392,800 h×pg/mL±86,300 h×pg/mL when administered orally to a human.

46. The composition of claim 35, wherein the conjugate results in the mean $t_{1/2}$ of hydrocodone of about 4.99 hours±0.79 hours when administered orally to a human.

47. A composition comprising 53.36 mg benzoate-hydrocodone hydrochloride conjugate, wherein the conjugate has the following structure:

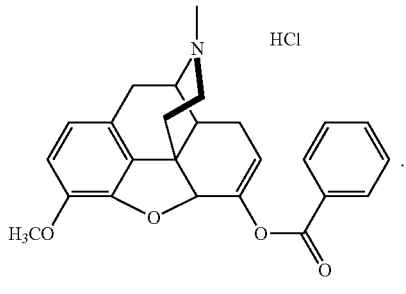

benzoate-hydrocodone
(Bz-HC)

48. The composition of claim 47 further comprising 2600 mg acetaminophen.

49. The composition of claim 48, wherein the conjugate results in the mean $C_{max}$ of hydrocodone of about 147,000 pg/mL±54,100 pg/mL when administered orally to a human.

50. The composition of claim 48, wherein the conjugate results in the mean $T_{max}$ of hydrocodone of about 1.05 hours when administered orally to a human.

51. The composition of claim 48, wherein the conjugate results in the range of $T_{max}$ of hydrocodone from about 0.6 hours to about 4.12 hours when administered orally to a human.

52. The composition of claim 48, wherein the conjugate results in the mean $AUC_{0-0.5\ h}$ of hydrocodone of about 26,900 h×pg/mL±14,770 h×pg/mL when administered orally to a human.

53. The composition of claim 48, wherein the conjugate results in the mean $AUC_{0-1\ h}$ of hydrocodone of about 88,750 h×pg/mL±42,380 h×pg/mL when administered orally to a human.

54. The composition of claim 48, wherein the conjugate results in the mean $AUC_{0-2\ h}$ of hydrocodone of about 193,400 h×pg/mL±66,470 h×pg/mL when administered orally to a human.

55. The composition of claim 48, wherein the conjugate results in the mean $AUC_{0-4\ h}$ of hydrocodone of about 353,500 h×pg/mL±97,670 h×pg/mL when administered orally to a human.

56. The composition of claim 48, wherein the conjugate results in the mean $AUC_{0-8\ h}$ of hydrocodone of about 566,900 h×pg/mL±128,200 h×pg/mL when administered orally to a human.

57. The composition of claim 48, wherein the conjugate results in the mean $AUC_{0-24\ h}$ of hydrocodone of about 811,900 h×pg/mL±175,100 h×pg/mL when administered orally to a human.

58. The composition of claim 48, wherein the conjugate results in the mean $AUC_{inf}$ of hydrocodone of about 842,100 h×pg/mL±190,800 h×pg/mL when administered orally to a human.

59. The composition of claim 48, wherein the conjugate results in the mean $t_{1/2}$ of hydrocodone of about 4.92 hours±0.95 hours when administered orally to a human.

60. A composition comprising 80.04 mg benzoate-hydrocodone conjugate, wherein the conjugate has the following structure:

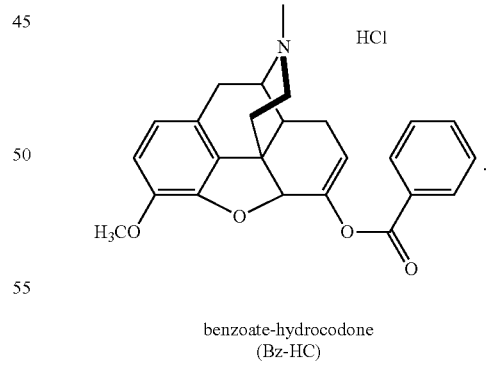

benzoate-hydrocodone
(Bz-HC)

61. The composition of claim 60 further comprising 3900 mg acetaminophen.

62. The composition of claim 61, wherein the conjugate results in the mean $C_{max}$ of hydrocodone of about 208,000 pg/mL±87,300 pg/mL when administered orally to a human.

63. The composition of claim 61, wherein the conjugate results in the mean $T_{max}$ of hydrocodone of about 1.05 hours when administered orally to a human.

64. The composition of claim 61, wherein the conjugate results in the range of $T_{max}$ of hydrocodone from about 0.6 hours to about 4.15 hours when administered orally to a human.

65. The composition of claim 61, wherein the conjugate results in the mean $AUC_{0-0.5\ h}$ of hydrocodone of about 37,140 h×pg/mL±22,750 h×pg/mL when administered orally to a human.

66. The composition of claim 61, wherein the conjugate results in the mean $AUC_{0-1\ h}$ of hydrocodone of about 121,900 h×pg/mL±65,280 h×pg/mL when administered orally to a human.

67. The composition of claim 61, wherein the conjugate results in the mean $AUC_{0-2\ h}$ of hydrocodone of about 263,500 h×pg/mL±103,300 h×pg/mL when administered orally to a human.

68. The composition of claim 61, wherein the conjugate results in the mean $AUC_{0-4\ h}$ of hydrocodone of about 487,500 h×pg/mL±154,300 h×pg/mL when administered orally to a human.

69. The composition of claim 61, wherein the conjugate results in the mean $AUC_{0-8\ h}$ of hydrocodone of about 816,300 h×pg/mL±208,800 h×pg/mL when administered orally to a human.

70. The composition of claim 61, wherein the conjugate results in the mean $AUC_{0-24\ h}$ of hydrocodone of about 1,217,00 h×pg/mL±296,800 h×pg/mL when administered orally to a human.

71. The composition of claim 61, wherein the conjugate results in the mean $AUC_{inf}$ of hydrocodone of about 1,272,000 h×pg/mL±326,500 h×pg/mL when administered orally to a human.

72. The composition of claim 61, wherein the conjugate results in the mean $t_{1/2}$ of hydrocodone of about 5 hours±1.79 hours when administered orally to a human.

73. An abuse-deterrent oral formulation comprising:
the composition of claim 1 wherein intranasal administration to a human results in mean peak hydrocodone plasma concentrations ($C_{max}$) from about 60% to about 69%, and in mean cumulative hydrocodone exposure (AUC) from about 10% to about 14% between 0 to 1 hour postdose, from about 42% to about 52% between 0 and 2 hours postdose, from about 60% to about 68% between 0 and 4 hours postdose, from about 70% to about 76% between 0 and 8 hours postdose, from about 73% to about 83% between 0 and 12 hours postdose and from about 76% to about 83% between 0 and 24 hours postdose when compared to an equimolar dose of hydrocodone bitartrate.

74. An abuse-deterrent oral formulation comprising:
the composition of claim 22 wherein intranasal administration to a human results in mean peak hydrocodone plasma concentrations ($C_{max}$) from about 96% to about 109%, and in mean cumulative hydrocodone exposure (AUC) from about 44% to about 60% between 0 to 1 hour postdose, from about 75% to about 87% between 0 and 2 hours postdose, from about 84% to about 92% between 0 and 4 hours postdose, from about 86% to about 93% between 0 and 8 hours postdose, and from about 86% to about 93% between 0 and 24 hours postdose when compared to an equimolar dose of hydrocodone bitartrate.

75. An abuse-deterrent oral formulation comprising:
a therapeutic dose of benzoate-hydrocodone hydrochloride conjugate that results in mean peak hydrocodone plasma concentrations ($C_{max}$) and mean overall hydrocodone exposure ($AUC_{last}$ and $AUC_{inf}$) after oral administration to a human from about 80% to about 125% when compared to an equimolar dose of hydrocodone bitartrate.

* * * * *